US012753426B2

(12) United States Patent
Cooperman et al.

(10) Patent No.: US 12,753,426 B2
(45) Date of Patent: Oct. 6, 2026

(54) HIGH THROUGHPUT ASSAYS FOR DETECTING TRANSLATION READTHROUGH INDUCERS

(71) Applicant: The Trustees of the University of Pennsylvania, Philadelphia, PA (US)

(72) Inventors: Barry S. Cooperman, Philadelphia, PA (US); Mikel D. Ghelfi, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 985 days.

(21) Appl. No.: 17/821,055

(22) Filed: Aug. 19, 2022

(65) Prior Publication Data

US 2023/0235374 A1 Jul. 27, 2023

Related U.S. Application Data

(60) Provisional application No. 63/234,928, filed on Aug. 19, 2021.

(51) Int. Cl.
*C12P 21/02* (2006.01)
*C12N 15/11* (2006.01)
*G01N 33/542* (2006.01)

(52) U.S. Cl.
CPC .............. *C12P 21/02* (2013.01); *C12N 15/11* (2013.01); *G01N 33/542* (2013.01)

(58) Field of Classification Search
CPC .................................................... G01N 33/542
See application file for complete search history.

(56) References Cited

PUBLICATIONS

Tobias Pusterla, BMG Labtech, Blog: "High-throughput screening (HTS)", Apr. 10, 2019. Retrieved from the Internet: < https://www.bmglabtech.com/en/blog/high-throughput-screening/ > Retrieved on Oct. 20, 2025.*
"Quest Graph™ Spectrum [Cy5 (Cyanine-5)]." AAT Bioquest, Inc., Oct. 20, 2025, Retrieved from Internet: < https://www.aatbio.com/fluorescence-excitation-emission-spectrum-graph-viewer/cy5_cyanine_5 > Retrieved on Oct. 20, 2025.*
"Quest Graph™ Spectrum [Cy3 (Cyanine-3)]." AAT Bioquest, Inc., Oct. 20, 2025, Retrieved from internet: < https://www.aatbio.com/fluorescence-excitation-emission-spectrum-graph-viewer/cy3_cyanine_3 >. Retrieved on Oct. 20, 2025.*
Barhoom et al., "Dicodon monitoring of protein synthesis (DiCoMPS) reveals levels of synthesis of a viral protein in single cells", Nucleic acids research, 2013, vol. 41, No. 18, pp. e177-e177.
Bevington et al., "Data Reduction and Error Analysis for the Physical Sciences", New York: McGraw-Hill, 2002, 338 pages.
Bhaskar et al., "Dynamics of uS19 C-Terminal Tail during the Translation Elongation Cycle in Human Ribosomes", Cell Rep, 2020, 31, 107473, 13 pages.
Buchmueller et al., "RNA-tethered phenyl azide photocrosslinking via a short-lived indiscriminant electrophile", J Am Chem Soc., Sep. 10, 2003, vol. 125 No. 36, pp. 10850-10861.
Busan et al., "Accurate detection of chemical modifications in RNA by mutational profiling (MaP) with ShapeMapper 2", RNA, 2018, vol. 24 No. 2, pp. 143-148.
Bushby, et al., "Ataluren treatment of patients with nonsense mutation dystrophinopathy", Muscle Nerve, 2014, vol. 50, pp. 477-487.
Campofelice et al., "Strategies against Nonsense: Oxadiazoles as Translational Readthrough-Inducing Drugs (TRIDs)", Int J Mol Sci, 2019, 20, 3329, pp. 1-18.
Chen et al., "Single-Molecule Fluorescence Measurements of Ribosomal Translocation Dynamics", Mol. Cell, 2011, vol. 42, pp. 367-377.
Crowley et al., "The signal sequence moves through a ribosomal tunnel into a noncytoplasmic aqueous environment at the ER membrane early in translocation", Cell, 1993, vol. 73, pp. 1101-1115.
Dobin et al., "STAR: ultrafast universal RNA-seq aligner", Bioinformatics, 2013, vol. 29, pp. 15-21.
Drake et al., "Correction of nonsense BMPR2 and SMAD9 mutations by ataluren in pulmonary arterial hypertension", Am J Respir Cell Mol Biol, 2013, vol. 49, pp. 403-409.
Flis et al., "tRNA translocation by the eukaryotic 80S ribosome and the impact of GTP hydrolysis", Cell reports, 2018, vol. 25 No. 10, pp. 2676-2688.e7.
Goldmann et al., "PTC124-mediated translational readthrough of a nonsense mutation causing Usher syndrome type 1C", Hum Gene Ther, 2011, vol. 22, pp. 537-547.
Gregory-Evans et al., "Postnatal manipulation of Pax6 dosage reverses congenital tissue malformation defects", J Clin Invest, 2014, vol. 124, pp. 111-116.
Hein et al., "A human interactome in three quantitative dimensions organized by stoichiometries and abundances", Cell, 2015, vol. 163, pp. 712-723.
https://wiki.yeastgenome.org/index.php/Modified_Nucleotides_within_RNAs_in_S._cerevisiae *Saccharomyces* Genome Database, Apr. 2014.
Jamiolkowski et al., "IRNA fluctuations observed on stalled ribosomes are suppressed during ongoing protein synthesis" Biophysical journal, 2017, vol. 113 No. 11, pp. 2326-2335.
Krawczak et al., "Human gene mutation database—a biomedical information and research resource", Hum Mutat, 2000, vol. 15, pp. 45-51.
Lawson et al., "Mechanisms that ensure speed and fidelity in eukaryotic translation termination", 2021, vol. 373, Issue 6557, pp. 876-882.
Lentini, et al., "Toward a rationale for the PTC124 (Ataluren) promoted readthrough of premature stop codons: a computational approach and GFP-reporter cell-based assay", Mol Pharm, 2014, vol. 11, pp. 653-664.
Li et al., "Muscle dysfunction and structural defects of dystrophin-null sapje mutant zebrafish larvae are rescued by ataluren treatment", FASEB J, 2014, vol. 28, pp. 1593-1599.

(Continued)

*Primary Examiner* — Suzanne M Noakes
(74) *Attorney, Agent, or Firm* — BakerHostetler

(57) ABSTRACT

Disclosed are systems and methods for high throughput screening to detect translation readthrough induced drugs (TRID). The systems use highly purified, eukaryotic cell-free protein synthesis systems that distinguish TRIDs acting directly on the protein synthesis machinery from those that act indirectly.

20 Claims, 38 Drawing Sheets

Specification includes a Sequence Listing.

(56) References Cited

PUBLICATIONS

Liu et al., "Monitoring collagen synthesis in fibroblasts using fluorescently labeled tRNA pairs", Journal of cellular physiology, 2014, vol. 229 No. 9, pp. 1121-1129.
McClary et al., "Inhibition of Eukaryotic Translation by the Anti-tumor Natural Product Agelastatin A", Cell Chem Biol, 2017, 24, 605-613, e605.
Milon et al., "Transient kinetics, fluorescence, and FRET in studies of initiation of translation in acteria", Methods Enzymol, 2007, 430, 1-30.
Mort et al., "A meta-analysis of nonsense mutations causing human genetic disease", Hum Mutat, 2008, vol. 29, pp. 1037-1047.
Ng et al., "Ataluren and aminoglycosides stimulate read-through of nonsense codons by orthogonal mechanisms", Proc Natl Acad Sci U S A, 2021, 118, e2020599118, pp. 1-10.
Ng et al., "New in Vitro Assay Measuring Direct Interaction of Nonsense Suppressors with the Eukaryotic Protein Synthesis Machinery", ACS Med Chem Lett, 2018, vol. 9, pp. 1285-1291.
Odom Jr., et al., "Distances between 3'ends of ribosomal ribonucleic acids reassembled into *Escherichia coli* ribosomes", Biochemistry, 1980, vol. 19 No. 26, pp. 5947-5954.
Peltz et al., "Ataluren as an agent for therapeutic nonsense suppression", Annu Rev Med, 2013, vol. 64, pp. 407-425.
Preis et al., "Cryoelectron microscopic structures of eukaryotic translation termination complexes containing eRF1-eRF3 or eRF1-ABCE1", Cell Rep., Jul. 10, 2014, vol. 8 No. 1, pp. 59-65.
Roy et al., "A practical guide to single-molecule FRET", Nat. Methods, 2008, vol. 5, pp. 507-516.
Roy et al., "Ataluren stimulates ribosomal selection of near-cognate tRNAs to promote nonsense suppression", Proc Natl Acad Sci U S A, 2016, vol. 113, pp. 12508-12513.
Roy et al., "Nonsense suppression by near-cognate tRNAs employs alternative base pairing at codon positions 1 and 3", Proc Natl Acad Sci U S A., Mar. 10, 2015, vol. 112 No. 10, pp. 3038-3043.
Schuller et al., "Roadblocks and resolutions in eukaryotic translation", Nat Rev Mol Cell Biol., Aug. 2018, vol. 19 No. 8, pp. 526-541.
Shao et al., "Decoding Mammalian Ribosome-mRNA States by Translational GTPase Complexes", Cell, Nov. 17, 2016, vol. 167 No. 5, pp. 1229-1240.e15.
Sharma et al, "A single N1-methyladenosine on the large ribosomal subunit rRNA impacts locally its structure and the translation of key metabolic enzymes", Sci Rep. Aug. 9, 2018, vol. 8 No. 1, 11904.
Shoemaker et al., "Kinetic analysis reveals the ordered coupling of translation termination and ribosome recycling in yeast", Proc Natl Acad Sci U S A., Dec. 20, 2011, vol. 108 No. 51, pp. E1392-1398.
Susorov et al.,"Termi-Luc: a versatile assay to monitor full-protein release from ribosomes", RNA, 2020, vol. 26 No. 12, pp. 2044-2050.
Taoka et al., "Landscape of the complete RNA chemical modifications in the human 80S ribosome", Nucleic Acids Res., Oct. 12, 2018, vol. 46 No. 18, pp. 9289-9298.
Welch et al., "PTC124 targets genetic disorders caused by nonsense mutations", Nature, 2007, vol. 447, pp. 87-91.
Woody et al., "MEMLET: An Easy-to-Use Tool for Data Fitting and Model Comparison Using Maximum-Likelihood Estimation", Biophys. J., 2016, vol. 111, pp. 273-282.
Zhang "Kinetics of initiating polypeptide elongation in an IRES-dependent system", Elife, 2016, 5, e13429, 18 pages.
Zhirnov et al., "Action spectra for UV-light induced RNA-RNA crosslinking in 16S ribosomal RNA in the ribosome", Photochem Photobiol Sci., Jun. 2003, vol. 2 No. 6, pp. 688-693.
Zinshteyn, et al., "Assaying RNA structure with LASER-Seq", Nucleic Acids Res, 2019, vol. 47, pp. 43-55.

* cited by examiner

Ataluren

[3H]p-azidoataluren

PheLys(Atto647)ValArgGln-tRNA$^{Gln}$

HIGH THROUGHPUT ASSAYS FOR DETECTING TRANSLATION READTHROUGH INDUCERS

CROSS-REFERENCE TO RELATED APPLICATIONS

The present application claims priority to and the benefit of U.S. patent application No. 63/234,928, "High Throughput Assays For Detecting Translation Readthrough Inducers" (filed Aug. 19, 2021), the entirety of which is incorporated herein by reference for any and all purposes.

GOVERNMENT RIGHTS

This invention was made with government support under grant number GM127374 awarded by the National Institutes of Health. The government has certain rights in the invention.

SEQUENCE LISTING XML

The instant application contains a Sequence Listing XML which is being submitted herewith electronically in XML format and is hereby incorporated by reference in its entirety. Said XML copy, created on Apr. 1, 2026, is named 103241006866_SequenceListing_ST26_57.xml and is 78,798 bytes in size.

TECHNICAL FIELD

The present disclosure relates to the field of high throughput assays for detecting translation readthrough induced drugs.

BACKGROUND

Premature termination codons (PTCs) arise as a consequence of nonsense mutations. Such mutations lead to the replacement of an amino acid codon in mRNA by one of three stop codons, UAA, UGA, or UAG, and result in inactive truncated protein products. Nonsense mutations constitute about 20% of transmitted or de novo germline mutations. Globally, there are about 7000 genetically transmitted disorders in humans, and about 11% of all human disease mutations are nonsense mutations. Clearly, millions of people worldwide would benefit from effective therapies directed toward PTC suppression. Clinical trials have begun to evaluate the treatment of PTC disorders with therapeutic agents called nonsense suppressors (NonSups, also referred to herein as "translation readthrough inducer(s)" (TRI), "translation readthrough inducer drugs," "translation readthrough inducing drugs," or "translation readthrough induced drugs" (TRID)). TRIDs induce the selection of near cognate tRNAs at the PTC position, and insertion of the corresponding amino acids into the nascent polypeptide, a process referred to as "readthrough," which restores the production of full length functional proteins, albeit at levels considerably reduced from wild-type. In vitro, ex vivo, and in vivo experiments and clinical trials have identified a diverse structural set of TRIDs as candidates for PTC suppression therapy. To date, only one TRID, ataluren (known commercially as Translarna™), has been approved in the EU for clinical use, but this approval is limited to treatment of patients with nonsense-mediated Duchenne muscular dystrophy (DMD).

A critical barrier to development of TRIDs with broader therapeutic windows is the paucity of information regarding the precise mechanisms by which these molecules stimulate readthrough. Almost all published work measuring TRID-induced readthrough of eukaryotic PTCs have been carried out using animals, intact cells, or crude cell extracts. In such systems, TRID can promote readthrough directly, by binding to one or more of the components of the protein synthesis machinery, or indirectly, either by inhibiting nonsense-mediated mRNA decay or by modulating processes altering the cellular activity levels of protein synthesis machinery components. This multiplicity of possible mechanisms of nonsense suppression has complicated attempts to determine the precise mechanisms of action of specific TRIDs and limited the use of rational design in identifying new, more clinically useful TRIDs.

SUMMARY

Disclosed are systems comprising a substrate and a plurality of regions on the substrate, each region comprising a cell-free ribosome-dependent protein synthesis reporter complex, wherein the cell-free ribosome-dependent protein synthesis reporter complex comprises:

- a) transfer-ribonucleic acid linked to a peptide (peptidyl-tRNA), wherein one or more amino acids of the peptide are labeled with a fluorophore or a chromophore, or a transfer-ribonucleic acid linked to a fluorophore or a chromophore (labeled-tRNA);
- b) a modified ribonucleic acid (RNA) molecule comprising an internal ribosome entry site (IRES) linked to a coding region encoding the peptide of the peptidyl-tRNA and a termination codon (Stop-IRES mRNA); and
- c) a ribosome.

Also disclosed are assays for detecting translation readthrough induced drug (TRID), the assays comprising:

- a) combining
  - i) a cell-free ribosome-dependent protein synthesis reporter complex comprising
    - ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA),
    - ib) a modified ribonucleic acid (RNA) molecule comprising an internal ribosome entry site (IRES) linked to a coding region encoding the peptide of the peptidyl-tRNA and a termination codon (Stop-IRES mRNA), and
    - ic) a ribosome;
  - ii) a drug; and
  - iii) a release factor complex; and
- b) measuring fluorescence anisotropy or measuring change in fluorescence or absorption.

In some aspects, the assay is for detecting TRIDs effective in a disease defined by a premature stop codon (PSC) mutation, the assay comprising:

- a) combining
  - i) a cell-free ribosome-dependent protein synthesis reporter complex comprising
    - ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA), ib) a modified ribonucleic acid (RNA) molecule comprising a portion of an mRNA comprising the premature stop codon (PSC) mutation, an internal ribosome entry site (IRES) linked to a coding region encoding the peptide of the peptidyl-tRNA and a termination codon (Stop-IRES mRNA), and ic) a ribosome;

ii) a drug; and iii) a release factor complex; and b) measuring fluorescence anisotropy or measuring change in fluorescence or absorption.

BRIEF DESCRIPTION OF THE DRAWINGS

FIG. 1D is a diagram of a Stop-IRES encoding FKVRQStopLM (SEQ ID NO: 57) with Lys (K), the termination product of which includes Lys (K) labeled with fluorophore. FIG. 1E is a diagram of a Stop-IRES encoding FCFFQStopLM (SEQ ID NO: 21, encoded by SEQ ID NO: 56), the termination product of which includes Cys (C) labeled with a fluorophore. FIG. 1F is a diagram showing the structure of an exemplary peptidyl-tRNA (SEQ ID NO: 24).

FIG. 2A is a graph showing the readthrough efficacy of AzAt measured by PURE-Lite readthrough assay. AzAt is shown to display similar sigmoidal response as ataluren and ataluren-like compounds (Ng et al., 2018), with the apparent EC50 of 50±10 μM. FIG. 2B illustrates AzAt photoincorporation into Stop-POST5 and the RNA fraction of Stop-POST5. FIG. 2C illustrates AzAt photoincorporation into 80S-IRES and the total RNA isolated from 80S.IRES. All of the labeling stoichiometries in FIG. 2A and FIG. 2B are normalized to the saturation labeling of Stop-POST5, which was equal to 1.2/Stop-POST5. FIG. 2D illustrates AzAt photoincorporation into eRF1 both alone and complexed with eRF3.GDPNP. The values are normalized to the saturation labeling of isolated eRF1. FIG. 2E illustrates inhibition of AzAt photoincorporation by the addition of either ataluren or GJ072. FIG. 2F is a graph showing Photoaffinity labeling of eRF3 alone or within release factor ternary complex. Both of them show near linear responses to increasing concentration of AzAt, suggesting photo-incorporation into eRF3 likely resulted from nonspecific binding of AzAt.

FIG. 3A, FIG. 3B, and FIG. 3C illustrate MA plots showing the mutation rate fold change of PAL over PRE as a function of average mutation counts of PAL and PRE for Stop-POST5 and 80S-IRES respectively. Nucleotides of interest are indicated and expanded from the boxed region in FIG. 3B and shown in FIG. 3C. FIG. 3D illustrates the reproductivity of the mutation rates of the selected 22 nucleotides. Two independent PAL LASER-seq assay were performed with the same condition. The PRE LASER-seq assay was done with or without re-photolysis, and little impact was observed with the re-photolysis condition on these 22 nucleotides. FIG. 3E illustrates the mutation rate fold change for PAL vs. PRE samples for Stop-POST5 and 80S.IRES complexes for the 22 sites most pertinent for ataluren function (as indicated on the x-axis).

FIG. 6A illustrates the location of A1195 within the 40S subunit containing bound eRF1. FIG. 6B illustrates the polar pocket of uS19 formed by Tyr123, Lys124, and Lys 100 in rabbit reticulocyte 40S subunit proximal to A1240 (A1195 in shrimp ribosomes) and eRF1 (on the right). FIG. 6C illustrates the locations of A2669, A2672, and A3093 within the 60S subunit containing bound eRF1.

FIG. 8A and FIG. 8C illustrate sample traces following eRF1/eRF3 injection. In FIG. 8A, the peptide signal disappears prior to tRNA signal; in FIG. 8C the tRNA signal disappears prior to peptide signal. FIG. 8B and FIG. 8D illustrate corresponding real-time scatter plots of the traces presented in FIG. 8A and FIG. 8C, respectively, where each dot represents one frame. FIG. 8E illustrates sample trace from a control experiment where only buffer was injected to obtain the photobleaching/spontaneous dissociation rate, which is clearly much slower than the rates seen FIG. 8A and FIG. 8C. FIG. 8F illustrates the real-time scatter plot of the trace presented in FIG. 8E.

FIG. 9E illustrates at different RFC concentrations (0.0375, 0.05 & 0.2 μM). The control shows the near constancy of observed anisotropy in the absence of added RFC or ataluren. FIG. 9F illustrates at fixed RFC concentration (0.0625 μM) and varying ataluren concentration (0, 500 & 1000 μM).

FIG. 15A-FRET diagram from proximity of Cy5-hRF1.hRF3 and Cy3-peptidyl-tRNA. FIG. 15B is a Cy5-hRF1.hRF3: Cy3-peptidyl-tRNA trace showing FRET. FIG. 15C is a graph showing ataluren inhibition of RFC binding. FIG. 15D is a graph showing Trp-TC inhibition of RFC binding.

In FIGS. 16A-16D, Cy5-Trp-TC is binding to a POST5 complex containing FKVRQ-tRNAGln (Cy3) (SEQ ID NO: 22) in P-Site and the three traces shown correspond to Cy3 donor emission (FIGS. 16A and 16C, top line); Cy5 sensitized emission (FIGS. 16A and 16C, bottom line); and FRET efficiency (E) (FIGS. 16B and 16D). FIGS. 16A and 16B show binding to cognate Trp-POST5. Changes of E at binding of the TC, accommodation into the A-site, and formation of the peptide bond are shown by arrows. FIGS. 16C and 16D show binding to near-cognate Stop-POST5. "Tests" are brief interactions in which the TC is rejected several times prior to stable binding. FIG. 16E is a diagram representation and FIGS. 16F and 16G are a smFRET recording of the initial cognate Trp-PRE6 complex containing FKVRQW-tRNATrp (Cy5) (SEQ ID NO: 23) in A-site and tRNAGln (Cy3) in the P-site following eEF2.GTP binding, translocation to the Trp-POST6 state and dissociation of tRNAGln (Cy3). FIG. 16H is a graph showing dependence of translocation rate on [eEF2] calculated from the average time between injection of eEF2.GTP and the FRET increase upon movement of the tRNAs. FIG. 16I is a graph showing duration of occupancy of E-site tRNAGln (Cy3) after translocation. For FIGS. 16H and 16I, dead-time of mixing and photobleaching rate are taken into account.

FIG. 17A is a graph showing a stable prf-fluorescence increase at different G418 concentrations [G418] due to eEF2-dependent conversion of a Stop-PRE6 complex to a Stop-POST6 complex, resulting from the increase in quantum yield of Trp-tRNA (prf). FIG. 17B is a graph showing fluorescence results in FIG. 17A as a function of [G418]. FIG. 17C is a graph showing the kinetics of Stop-PRE6 translocation, measured at 1 μM eEF2 and 2 μM G418. FIG. 17D is a graph showing the kinetics of Trp-PRE6 translocation to Trp-POST6 measured at 0.05 μM of eEF2 in the absence of G418.

DETAILED DESCRIPTION OF ILLUSTRATIVE EMBODIMENTS

Figure 1A:
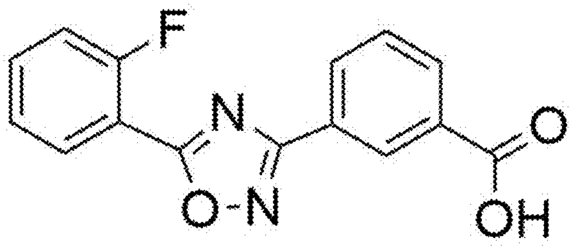
FIG. 1A, FIG. 1B, FIG. 1C, FIG. 1D, FIG. 1E, and FIG. 1F are diagrams showing structures of ataluren (FIG. 1A). [$^3$H]-AzAt (FIG. 1B), and Stop-IRES encoding FKVRQStopLM (SEQ ID NO: 20, encoded by SEQ ID NO: 55, FIG. 1C).

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints (e.g., "between 2 grams and 10 grams, and all the intermediate values includes 2 grams, 10 grams, and all intermediate values"). The endpoints of the ranges and any values disclosed herein are not limited to the precise range or value; they are sufficiently imprecise to include values approximating these ranges and/or values. All ranges are combinable.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. Further, the term "comprising" should be understood as having its open-ended meaning of "including," but the term also includes the closed meaning of the term "consisting." For example, a composition that comprises components A and B may be a composition that includes A, B, and other components, but may also be a composition made of A and B only. Any documents cited herein are incorporated by reference in their entireties for any and all purposes.

Disclosed is a highly purified, eukaryotic cell-free protein synthesis system that distinguishes TRID acting directly on the protein synthesis machinery from those that act indirectly. Directly acting TRID can stimulate readthrough at a PTC by either facilitating productive binding of near-cognate tRNA to the ribosome and/or by inhibiting eRF1/eRF3-induced peptide release (i.e., termination of protein synthesis). The disclosed assay utilizes a fluorescent peptidyl-tRNA substrate that permits high throughput measurement of the termination activities of large libraries of potential TRIDs. This assay measures the decrease in fluorescence anisotropy that results from eRF1/eRF3-induced peptide release of fluorescently-labeled peptide attached to a tRNA bound to the ribosome P-site that is adjacent to a stop codon, such as a UGA stop codon.

Also disclosed are peptidyl-tRNAs that can include one or more canonical or non-canonical amino acids. The peptidyl-tRNAs that can include a label, such as a fluorophore or a chromophore, linked to the one or more canonical or non-canonical amino acids. The link between the fluorophore or a chromophore and the one or more canonical or non-canonical amino acids can be a covalent link. The covalent links between the fluorophore or a chromophore and the one or more canonical or non-canonical amino acids can be from chemical conjugation, crosslinking, or click chemistry reactions.

A large number of diseases including cystic fibrosis, Duchenne muscular dystrophy, β-thalassemia, and many types of cancers are caused by the presence of premature stop mutations in mRNAs. Premature stop mutations can arise as a result of mutations within germline or somatic DNA, inaccurate or inefficient pre-mRNA splicing, or improper RNA editing. The disclosed system can be used to detect termination-specific TRIDs to stimulate readthrough at stop codons in specific sequence contexts. Such predictive ability could aid in determining which PSC sequence contexts found in patients with premature stop mutations in mRNAs that have the highest probability for being successfully treated by termination-specific TRIDs.

Also disclosed is a system comprising a substrate and a plurality of regions on the substrate, each region comprising a cell-free ribosome-dependent protein synthesis reporter complex. The cell-free ribosome-dependent protein synthesis reporter complex can include:

a) transfer-ribonucleic acid linked to a peptide (peptidyl-tRNA), wherein one or more amino acids of the peptide are labeled with a fluorophore or a chromophore, or a transfer-ribonucleic acid linked to a fluorophore or a chromophore (labeled-tRNA);

b) a modified ribonucleic acid (RNA) molecule comprising an internal ribosome entry site (IRES) linked to a coding region encoding the peptide of the peptidyl-tRNA and a termination codon (Stop-IRES mRNA); and c) a ribosome.

The peptidyl-tRNA in the system can comprise between one and 15 amino acids, between one and ten amino acids, between one and eight amino acids, between two and five amino acids, or one amino acid. The peptidyl-tRNA can comprise at least one canonical or non-canonical amino acid labeled with the fluorophore or the chromophore. Suitable fluorophores or suitable chromophores include those that absorb light at wavelengths between about 340 nm and 780 nm. Suitable fluorophores or suitable chromophores include those that emits light at wavelengths between about 440 nm and 810 nm.

In some embodiments, the IRES in the system is from cricket paralysis virus internal ribosome entry site (CrPV-IRES). In some embodiments, the ribosome is a eukaryotic ribosome. In some embodiments, the cell-free ribosome-dependent protein synthesis reporter complex can comprise eukaryotic elongation factors (eEF)1A and eEF2, and aminoacyl-tRNAs (aa-tRNAs). The cell-free ribosome-dependent protein synthesis reporter complex can include the peptidyl-tRNA is located at peptidyl-site (P-site) of the ribosome, forming Stop-POST complex.

A region in the plurality of regions on the substrate can comprise an isolated area selected from the group consisting of a matrix, a well, a vessel, and a chamber.

Also disclosed are assays for detecting translation read-through induced drug (TRIDs). The assays can comprise:

a) combining
   i) a cell-free ribosome-dependent protein synthesis reporter complex comprising
      ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA),
      ib) a modified ribonucleic acid (RNA) molecule comprising an internal ribosome entry site (IRES) linked to a coding region encoding the peptide of the peptidyl-tRNA and a termination codon (Stop-IRES mRNA), and
      ic) a ribosome;
   ii) a drug; and
   iii) a release factor complex; and
b) measuring fluorescence anisotropy or measuring change in fluorescence or absorption.

The peptidyl-tRNA for the assays can comprise between one and 15 amino acids, between one and ten amino acids, between one and eight amino acids, between two and five amino acids, or one amino acid. The peptidyl-tRNA for the assays can comprise at least one canonical or non-canonical amino acid labeled with the fluorophore or the chromophore. Suitable fluorophores or the chromophores for the assays include those that absorb light at wavelengths between about 340 nm and 780 nm. Suitable fluorophores or the chromophores for the assays include those that emits light at wavelengths between about 440 nm and 810 nm. The cell-free ribosome-dependent protein synthesis reporter complex for the assays can comprise cricket paralysis virus internal ribosome entry site (CrPV-IRES). The cell-free ribosome-dependent protein synthesis reporter complex for the assays can comprise is a eukaryotic ribosome. The cell-free ribosome-dependent protein synthesis reporter complex for the assays can further comprise eukaryotic elongation factors (eEF)1A and eEF2, and aminoacyl-tRNAs. The peptidyl-tRNA in the cell-free ribosome-dependent protein synthesis reporter complex for the assays can be located at peptidyl-site (P-site) of the ribosome.

In some embodiments, the assays comprise adding guanosine-5'-triphosphate (GTP).

The drug for the assays can comprise a from a library of drugs.

In some embodiments, the release factor for the assays is selected from the group consisting of eukaryotic peptide release factor (eRF)1, eRF3, and Rli1/ABCE1.

The measuring of fluorescence anisotropy for the assays can comprise measuring fluorescence from the cell-free ribosome-dependent protein synthesis reporter complex. The drug is identified as a translation readthrough induced drug when the fluorescence anisotropy is substantially reduced during a measuring period. The drug is not identified as a translation readthrough induced drug when the fluorescence anisotropy is substantially unchanged during a measuring period.

In some embodiments, the assays comprise high throughput assays. The assays can be performed with any one of the disclosed systems.

Also disclosed are assays for detecting translation read-through induced drug (TRID) effective in a disease defined by a premature stop codon (PSC) mutation, the assays comprising:

a) combining
   i) a cell-free ribosome-dependent protein synthesis reporter complex comprising
      ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA),
      ib) a modified ribonucleic acid (RNA) molecule comprising a portion of an mRNA comprising the premature stop codon (PSC) mutation, an internal ribosome entry site (IRES) linked to a coding region encoding the peptide of the peptidyl-tRNA and a termination codon (Stop-IRES mRNA), and
      ic) a ribosome;
   ii) a drug; and
   iii) a release factor complex; and
b) measuring fluorescence anisotropy or measuring change in fluorescence or absorption.

The assays can comprise a cell-free ribosome-dependent protein synthesis reporter complex where the portion of the mRNA with the premature stop codon (PSC) mutation comprises between two and 15 consecutive codons. The assays can comprise a cell-free ribosome-dependent protein synthesis reporter complex where the portion of the mRNA comprising the premature stop codon (PSC) mutation is a portion of mRNA encoding a truncated protein. The assays can comprise a cell-free ribosome-dependent protein synthesis reporter complex where the portion of the mRNA comprising the premature stop codon (PSC) mutation is a portion of mRNA encoding a truncated protein associated with a premature termination codon (PTC) disorder. The assays can comprise a cell-free ribosome-dependent protein synthesis reporter complex where the portion of the mRNA comprising the premature stop codon (PSC) mutation is a portion of mRNA encoding cystic fibrosis transmembrane conductance regulator (CFTR) protein. The labeled-tRNA can comprise a labeled aa-tRNA. The labeled-tRNA can comprise any tRNA or any aa-tRNA linked to a fluorophore or a chromophore.

EMBODIMENTS

Embodiment 1. A system comprising a substrate and a plurality of regions on the substrate, each region comprising a cell-free ribosome-dependent protein synthesis reporter complex, wherein the cell-free ribosome-dependent protein synthesis reporter complex comprises:

a) transfer-ribonucleic acid linked to a peptide (peptidyl-tRNA), wherein one or more amino acids of the peptide are labeled with a fluorophore or a chromophore, or a transfer-ribonucleic acid linked to a fluorophore or a chromophore (labeled-tRNA);
b) a modified ribonucleic acid (RNA) molecule comprising an internal ribosome entry site (IRES) linked to a coding region encoding the peptide of the peptidyl-tRNA and a termination codon (Stop-IRES mRNA); and
c) a ribosome.

Embodiment 2. The system of embodiment 1, wherein the peptidyl-tRNA comprises between one and 15 amino acids.

Embodiment 3. The system of embodiment 1 or 2, wherein the peptidyl-tRNA comprises between one and ten amino acids.

Embodiment 4. The system of any one of embodiments 1-3, wherein the peptidyl-tRNA comprises between one and eight amino acids.

Embodiment 5. The system of any one of embodiments 1-4, wherein the peptidyl-tRNA comprises between two and five amino acids.

Embodiment 6. The system of any one of embodiments 1-5, wherein the peptidyl-tRNA comprises at least one canonical or non-canonical amino acid labeled with the fluorophore or the chromophore.

Embodiment 7. The system of any one of embodiments 1-6, wherein the fluorophore or the chromophore absorbs light at wavelengths between about 340 nm and 780 nm.

Embodiment 8. The system of any one of embodiments 1-7, wherein the fluorophore or the chromophore emits light at wavelengths between about 440 nm and 810 nm.

Embodiment 9. The system of any one of embodiments 1-8, wherein the IRES is from cricket paralysis virus internal ribosome entry site (CrPV-IRES).

Embodiment 10. The system of any one of embodiments 1-9, wherein the ribosome is a eukaryotic ribosome.

Embodiment 11. The system of any one of embodiments 1-10, wherein the cell-free ribosome-dependent protein synthesis reporter complex further comprises eukaryotic elongation factors (eEF)1A and eEF2, and aminoacyl-tRNAs.

Embodiment 12. The system of any one of embodiments 1-11, wherein the peptidyl-tRNA is located at peptidyl-site (P-site) of the ribosome, forming Stop-POST complex.

Embodiment 13. The system of any one of the preceding embodiments, wherein the region comprises an isolated area selected from the group consisting of a matrix, a well, a vessel, and a chamber.

Embodiment 14. An assay for detecting translation readthrough induced drug (TRID), the assay comprising:

a) combining
   i) a cell-free ribosome-dependent protein synthesis reporter complex comprising
      ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA),
      ib) a modified ribonucleic acid (RNA) molecule comprising an internal ribosome entry site (IRES) linked to a coding region encoding the peptide of the peptidyl-tRNA and a termination codon (Stop-IRES mRNA), and
      ic) a ribosome;
   ii) a drug; and
   iii) a release factor complex; and
b) measuring fluorescence anisotropy or measuring change in fluorescence or absorption.

Embodiment 15. The assay of embodiment 14, wherein the peptidyl-tRNA comprises between one and 15 amino acids.

Embodiment 16. The assay of embodiment 14 or 15, wherein the peptidyl-tRNA comprises between one and ten amino acids.

Embodiment 17. The assay of any one of embodiments 14-16, wherein the peptidyl-tRNA comprises between one and eight amino acids.

Embodiment 18. The assay of any one of embodiments 14-17, wherein the peptidyl-tRNA comprises between two and five amino acids.

Embodiment 19. The assay of any one of embodiments 14-18, wherein the peptidyl-tRNA comprises at least one canonical or non-canonical amino acid labeled with the fluorophore or the chromophore.

Embodiment 20. The assay of any one of embodiments 14-19, wherein the fluorophore or the chromophore absorbs light at wavelengths between about 340 nm and 780 nm.

Embodiment 21. The assay of any one of embodiments 14-20, wherein the fluorophore or the chromophore emits light at wavelengths between about 440 nm and 810 nm.

Embodiment 22. The assay of any one of embodiments 14-21, wherein the IRES is from cricket paralysis virus internal ribosome entry site (CrPV-IRES).

Embodiment 23. The assay of any one of embodiments 14-22, wherein the ribosome is a eukaryotic ribosome.

Embodiment 24. The assay of any one of embodiments 14-23, wherein the cell-free ribosome-dependent protein synthesis reporter complex further comprises eukaryotic elongation factors (eEF)1A and eEF2, and optionally, aminoacyl-tRNAs.

Embodiment 25. The assay of any one of embodiments 14-24, wherein the peptidyl-tRNA is located at peptidyl-site (P-site) of the ribosome.

Embodiment 26. The assay of any one of embodiments 14-25 comprising adding guanosine-5'-triphosphate (GTP).

Embodiment 27. The assay of any one of embodiments 14-26, wherein the drug is from a library of drugs.

Embodiment 28. The assay of any one of embodiments 14-27, wherein the release factor is selected from the group consisting of eukaryotic peptide release factor (eRF)1, eRF3, and Rli1/ABCE1.

Embodiment 29. The assay of any one of embodiments 14-28, wherein measuring fluorescence anisotropy or measuring change in fluorescence or absorption comprises measuring fluorescence from the cell-free ribosome-dependent protein synthesis reporter complex.

Embodiment 30. The assay of any one of embodiments 14-29, wherein the drug is translation readthrough induced drug when the fluorescence anisotropy is substantially reduced during a measuring period.

Embodiment 31. The assay of any one of embodiments 14-29, wherein the drug is not a translation readthrough induced drug when the fluorescence anisotropy is substantially unchanged during a measuring period.

Embodiment 32. The assay of any one of embodiments 14-31 comprising a high throughput assay.

Embodiment 33. The assay of any one of embodiments 14-32 performed with a system of any one of embodiments 1-14.

Embodiment 34. An assay for detecting translation readthrough induced drug (TRID) effective in a disease defined by a premature stop codon (PSC) mutation, the assay comprising:

a) combining
   i) a cell-free ribosome-dependent protein synthesis reporter complex comprising
      ia) a transfer-ribonucleic acid linked to a peptide (peptidyl-tRNA) labeled at one or more amino acids of the peptide with a fluorophore or a chromophore, or a transfer-ribonucleic acid linked to a fluorophore or a chromophore (labeled-tRNA),
      ib) a modified ribonucleic acid (RNA) molecule comprising a portion of an mRNA comprising the premature stop codon (PSC) mutation, an internal ribosome entry site (IRES) linked to a coding region encoding the peptide of the peptidyl-tRNA and a termination codon (Stop-IRES mRNA), and ic) a ribosome;

ii) a drug; and iii) a release factor complex; and b) measuring fluorescence anisotropy or measuring change in fluorescence or absorption.

Embodiment 35. The assay of embodiment 34, wherein the portion of the mRNA comprising the premature stop codon (PSC) mutation comprises between two and fifteen consecutive codons.

Embodiment 36. The assay of embodiment 34 or 35, wherein the portion of the mRNA comprising the premature stop codon (PSC) mutation is a portion of mRNA encoding a truncated protein.

Embodiment 37. The assay of any one of embodiments 34-36, wherein the portion of the mRNA comprising the premature stop codon (PSC) mutation is a portion of mRNA encoding a truncated protein associated with a premature termination codon (PTC) disorder.

Embodiment 38. The assay of any one of embodiments 34-37, wherein the portion of the mRNA comprising the premature stop codon (PSC) mutation is a portion of mRNA encoding cystic fibrosis transmembrane conductance regulator (CFTR) protein.

Embodiment 39. A high throughput assay for detecting translation readthrough induced drug (TRID) effective in a disease defined by a premature stop codon (PSC) mutation, the assay comprising:

a) combining i) a cell-free ribosome-dependent protein synthesis reporter complex comprising ia) a transfer-ribonucleic acid linked to a fluorophore or a chromophore (labeled-tRNA), ib) a modified ribonucleic acid (RNA) molecule comprising a portion of an mRNA comprising the premature stop codon (PSC) mutation, an internal ribosome entry site (IRES) linked to a coding region encoding the peptide of the peptidyl-tRNA and a termination codon (Stop-IRES mRNA), and ic) a ribosome;

ii) a drug; and iii) a release factor complex; and b) measuring change in fluorescence or absorption, wherein the portion of the mRNA comprising the premature stop codon (PSC) mutation is a portion of mRNA encoding a truncated protein associated with a premature termination codon (PTC) disorder selected from the group consisting of cystic fibrosis, Duchenne muscular dystrophy, β-thalassemia, and cancer.

EXAMPLES

Presented are results from experiments performed with a $^{3}$H-labeled photolabile congener of ataluren, which identify three sites of ataluren binding within the PURE-LITE system. The system named PURE-LITE differentiates from the more complete PURE systems that have been developed for bacterial (Preis et al., Cell Rep. 2014 Jul. 10; 8 (1): 59-65) and eukaryotic protein synthesis (Shao et al., Cell. 2016 Nov. 17; 167 (5): 1229-1240.e15). PURE-LITE employs only the following purified components: eukaryotic 80S ribosomes programmed with variants of the cricket paralysis virus (CrPV) internal ribosome entry site (IRES) mRNA (FIG. 1C, FIG. 1D, and FIG. 1E), which can synthesize polypeptides in the complete absence of protein initiation factors.

Two of these sites are within rRNA, proximal to the decoding center (DC) and the peptidyl transfer center (PTC) of the ribosome, respectively, and one is within eRF1. Also presented are single molecule and ensemble fluorescence assays used to determine that RFC binding to a pretermination complex resulted in comparatively rapid hydrolysis of peptidyl-tRNA, followed by a much slower release of peptide and tRNA from the ribosome. Therefore, ataluren is an apparent competitive inhibitor of productive RFC binding to a pretermination complex, acting exclusively at or before the hydrolysis step. Using this assay system, the results showed that ataluren binding to the two rRNA sites is directly responsible for ataluren inhibition of termination activity. The assay screens small molecules to identify other TRIDs with higher affinity for pretermination complexes than ataluren and focus on areas of the RFC binding site on the ribosome proximal to the DC and PTC which do not overlap with the near-cognate ternary complex (TC) binding site.

Materials and Methods for Examples 1~4

Materials

[$^{3}$H]-AzAt was prepared by catalytic tritiation (Vitrax, Placentia, CA) of 3-[5-(4-azidophenyl)-1,2,4-oxadiazol-3-yl]-6-iodo benzoic acid (6-iodo-AzAt), provided by PTC Therapeutics. The chemical purity of the tritiated product was verified by its comigration with authentic AzAt on RP-HPLC analysis. Both AzAt, and 6-iodo-AzAt were supplied by PTC Therapeutics. Atto647-N-hydroxysuccinimide ester (Atto647-NHS) was obtained from Sigma.

ATTO 647-ε-lysine $tRNA^{Lys}$ formation. Atto647-ε-lysine $tRNA^{Lys}$ was prepared by reacting Atto647-NHS with [$^{3}$H] Lys-$tRNA^{Lys}$ (*S. cerevisiae*) following a procedure based on that used for the preparation of NBD-&-[$^{3}$H] Lys-$tRNA^{Lys}$ (30). Briefly, Atto647 NHS ester dissolved in DMSO (38.5 mM, 10 μl) was added quickly to a 50 mM $K^{+}$ phosphate buffer, pH 11 (20 μl) and DMSO (50 μl) solution followed directly by [$^{3}$H] Lys-$tRNA^{Lys}$ (20 nmol, 165 μM, 120 μl) dissolved in water, reaching a final concentration of 0.1 mM tRNA and 2.0 mM dye at a final pH of 10.8. A color change from dark blue to dark teal was observed. The mixture was stirred in a thermomixer for 4 min at 25° C., quenched with 4 M acetic acid (17 μl), which restores the original blue color, and directly ethanol precipitated (20% potassium acetate pH 5 (2.7 ml), cold EtOH (17 ml) at −80° C. for 1 h). Ethanol precipitation was repeated twice to remove any residual Atto647-NHS, and the resulting aqueous solution was stored and stored as an aqueous solution containing diethyl pyrocarbonate (0.1%) in small aliquots at −80° C. The stoichiometry of [$^{3}$H]-Lys charging was typically 0.35±0.05/$tRNA^{Lys}$. The stoichiometry of Atto647 labeling, measured by UV absorption (€647:120000 mol$^{-1}$ cm$^{-1}$), was 10% higher, i.e., 0.40±0.05/$tRNA^{Lys}$ Ribosome complexes. 80S-S.IRES and Stop-POST5 complexes used in photoaffinity labeling and fluorescence anisotropy experiments were either prepared from shrimp (*Artemia salina*) cysts 40S and 60S subunits, Stop-IRES, aminoacyl-tRNAs (Phe-$tRNA^{Phe}$, Lys-$tRNA^{Lys}$, Val-$tRNA^{Val}$, Arg-$tRNA^{Arg}$, Gln-$tRNA^{Gln}$), yeast elongation factors (eEF1A and eEF2), and GTP (photoaffinity labeling and fluorescence anisotropy experiments), as previously described (Zhang et al., Elife. 5: e13429 (2016)), or via a high KCl treatment of 80S ribosomes (fluorescence anisotropy experiments). In the latter case, crude 80S ribosomes were dissolved in Buffer 4 (40 mM Tris HCl, pH 7.5, 80 mM $NH_4Cl$, 5 mM Mg (Ac) 2, 100 mM KOAc, and 3 mM β-mercaptoethanol) and pelleted by microultracentrifugation for 1 h at 110 k rpm 4° C. The washed 80S ribosomes (2 μM) were combined with Stop-IRES (4 μM) in Buffer 4 supplemented with added 0.4 M KCl and incubated at 37° C. for 30 min. The resulting 80S.Stop-IRES complex was ultracentrifuged through a 1.1 M sucrose solution in Buffer 4 (1.65× of reaction volume) for 1 h at 110 k rpm at 4° C., and the pellet was dissolved in Buffer 4 and stored in small aliquots at −80° C. This preparation of 80S.Stop-IRES complex was used to make Stop-POST5 complex by a process essentially identical to that used for converting 80S.Stop-IRES made from 40S and 60S subunits to Stop-POST5 complex (Zhang et al., Elife. 5: e13429 (2016)).

80S.IRES concentrations were estimated by A260 measurement, while the concentration of Stop-POST5 was estimated from both the A260 measurement and the stoichiometry of radioactively labeled pentapeptide per 80S ribosome. Typically, 40±5% of the 80S ribosome harbors the pentapeptide. For Atto(pep)-Stop-POST5 and Atto(pep)-Cy-Stop-POST5 preparation, Atto647-ε-lysine-$tRNA^{Lys}$ replaced lysine-$tRNA^{Lys}$. Also, for Atto(pep)-Cy-Stop-POST5 and Atto(rbsm)-Cy-Stop-POST5 preparation, Gln-$tRNA^{Gln}$ (Cy3) replaced Gln-$tRNA^{Gln}$. Finally, for Atto(rbsm)-Cy(tRNA)-Stop-POST5 and Atto(pep)-Cy(ribsm)-Stop-POST5 preparation, ribosomes labeled on r-protein Lys residues to an average stoichiometry of 0.82 Atto647/ribosome and 0.95 Cy3/ribosome, respectively, replaced unlabeled ribosomes. Such labeled ribosomes were prepared using a previously published method for *E. coli* 70S ribosome labeling with minor modification (Milon et al., Methods Enzymol, 430:1-30 (2007)). In brief, labeling was performed in LB buffer (40 mM HEPES, pH 7.5, 80 mM $NH_4Cl$, 5 mM Mg (Ac) 2, 100 mM KOAc). A sample of crude 80S shrimp ribosomes, was layered on top of 1.1M sucrose in LB, then spun at 110,000 rpm for 90 min. The pellet was washed three times with LB and then dissolved again in LB. For the labeling reaction, a 2-fold molar excess of atto647N-NHS ester (atto-tech, dissolved in DMSO) and a 4-fold molar excess of Cy3-NHS ester (Lumiprobe, dissolved in DMSO) was incubated with 5 μM 80S ribosome in LB at 37° C. for 30 mins with stirring. After the reaction, the reaction mixture was layered on the top of 1.1M sucrose in Buffer 4, then spun at 110,000 rpm for 90 min. The labeled ribosome pellet was dissolved in Buffer 4. A final spin at 10,000 rpm for 2 min removes residual contaminants. The labeling efficiency was calculated by using the molar extinction coefficients of 80S ribosome at 260 nm of atto647N-NHS ester at 647 nm and of Cy3-NHS ester at 555 nm.

For the single-molecule experiments, Stop-POST5, prepared from subunits, was covalently attached to biotin at the 3' of the mRNA by periodate oxidation of RNA at its 3' end and reaction of the oxidized product with biotin hydrazide, as described (Odom Jr. et al., *Biochemistry,* 19 (26), 5947-5954 (1980)), with the following modifications. The oxidation of mRNA was performed in a solution containing mRNA at a concentration of 10-50 $A_{260}$/ml, 100 mM sodium acetate (pH 5.2), and 90 mM sodium m-periodate (prepared fresh). After a 2-hr incubation at room temperature, the periodate was precipitated by adding KCl to a final concentration of 200 mM and incubating for 5 minutes on ice. The precipitate was removed by centrifugation for 5 minutes at 10000 g, 2° C. and passage of the supernatant through a Sephadex G-25 column (Nap-5, Pharmacia). EZ-Link hydrazide Biotin (ThermoFisher, inc.) was then added to a final concentration of 2 mM from a 50 mM stock in DMSO (prepared fresh). The biotinylation reaction was carried out for 2 hours at room temperature, after which the whole mixture was applied to a Sephadex G-25 column (PD-10, Pharmacia), the high molecular weight fractions were precipitated by ethanol addition, and the resulting pellet was dissolved in DEPC treated $H_2O$. The concentration of biotinylated mRNA was determined by A260.

Yeast eEF1A and eEF2 preparations were adapted from the eEF2 preparation method described previously (Ng et al., *ACS Med Chem Lett,* 9, 1285-1291 (2018); Ng et al., *Proc Natl Acad Sci USA,* 118: e2020599118 (2021), incorporated by reference herein in its entirety; and Zhang et al., *Elife.* 5: e13429 (2016)). Full-length eRF1 and amino acid residues (166-685) of the eRF3 open reading frame sequences were inserted into the pET-15b (Novagen) plasmid obtained from the laboratory of Allan Jacobson (University of Massachusetts Medical School). eRF1 and eRF3 plasmids were transformed into BL21 (DE3) CodonPlus (Agilent) strain in the presence of ampicillin. eRF1 and eRF3 were isolated from cell lysate as described earlier (Ng et al., *ACS Med Chem Lett,* 9, 1285-1291 (2018); Ng et al., *Proc Natl Acad Sci USA,* 118: e2020599118 (2021); and Zhang et al., *Elife.* 5: e13429 (2016)).

TRIDs. Ataluren sodium salt and GJ072 were obtained as gifts from PTC Therapeutics.

tRNAs. Yeast $tRNA^{Phe}$ was purchased from Sigma-Aldrich. Other isoacceptor tRNAs were prepared from bulk tRNA (Roche) from either *E. coli* ($tRNA^{Val}$, $RNA^{Lys}$, $tRNA^{Gln}$), or yeast ($tRNA^{Arg}$), via hybridization to immobilized complementary oligo DNAs as described previously (Barhoom et al., *Nucleic acids research,* 41 (18), pp. e177-e177 (2013); Liu et al., *Journal of cellular physiology,* 229 (9), pp. 1121-1129 (2014)). *E. coli* and yeast tRNAs were charged with their cognate amino acids as described (Ng et al., *ACS Med Chem Lett,* 9, 1285-1291 (2018); Ng et al., *Proc Natl Acad Sci USA,* 118: e2020599118 (2021), incorporated by reference herein in its entirety; and Zhang et al., *Elife.* 5: e13429 (2016)).

Methods

Photoaffinity labeling with [$^3$H]-AzAt. Samples in Buffer 4, typically 20 μL, were incubated in the dark (20 min for Stop-POST5 and 80S-IRES complexes, 2 min for release factors) with various concentrations of [$^3$H]-AzAt at 37° C., transferred to a UV-transparent cuvette which was covered with parafilm to prevent evaporation, and irradiated in a Rayonet photochemical reactor equipped with 300 nm UV lamps for 5 min at room temperature. This was followed by quenching with 2 mM DTT at 37° C. for 5 min under ambient light. The irradiation time gave complete photolysis of the phenyl azide moiety in AzAt. Photolysis was also complete at 5 min in the presence of 1 mM ataluren, ruling out internal filtering effects.

Stop-POST5 and 80S-IRES complexes. 1 μM solutions of either Stop-POST5 or 80S-S.IRES, determined by A260, were photolabeled by [$^3$H]-AzAt. The sample was then either directly purified by ultracentrifugation through a sucrose cushion to determine the photoincorporation stoichiometry in the complex, or subjected to phenol/chloroform extraction to determine the photoincorporation stoichiometry in the total RNA. To determine the photoincorporation background arising from incomplete removal of noncovalently bound photolyzed AzAt, AzAt was prephotolysed for 5 min before adding to the complex, followed by the 20 min incubation in dark at 37° C. and subsequent sucrose cushion purification or RNA extraction as described above. This background level, which never exceeded 17±3% of what was observed for the photoincorporation experiment, was subtracted from the observed values in the reported results.

Photoaffinity labeling of release factors. Solutions containing eRF1 (10 μM), eRF3 (20 μM) and 1 mM GMPPMP were pre-incubated at 37° C. for 2 min to form the ternary complex prior to photolabeling with [$^{3}$H]-AzAt. After quenching, reaction mixtures were loaded onto a 4-15% mini protean SDS-PAGE gel for protein separation and isolation. Gel slices containing eRF1 or eRF3, as shown by Coomassie Blue R250 staining, were crushed and the radioactivity was extracted in extraction buffer (50 mM Tris-HCl, 150 mM NaCl, and 0.1 mM EDTA; pH 7.5) by vigorously shaking at 70° C. for 30 min. The data fitting was performed using the software Prism. Labeling results of eRF1 alone and within the eRF1.eRF3.GDPNP complex were fit with a one-site binding model and a two-site binding model, respectively.

RNA-Seq procedures employed closely follow those published (Zinshteyn et al., *Nucleic Acids Res,* 47, 43-55 (2019); McClary et al., *Cell Chem Biol,* 24, 605-613 e605 (2017)) except as noted.

Library preparation. RNA-seq libraries were prepared for PAL, PRE, UV, and NUL samples, as defined in Results, of Stop-POST5 and 80S.IRES complexes, using published procedures (Zinshteyn et al., *Nucleic Acids Res,* 47, 43-55 (2019); McClary et al., *Cell Chem Biol,* 24, 605-613 e605 (2017)) with the slight modifications that a 12% 0.13 M Tris/45 mM Borate/2.5 mM EDTA (pH 7.6))-Urea PAGE gel replaced a 10% PAGE gel and the selected RNA fragment size was 40-70 bp rather than 60-70 bp. In brief, RNA was extracted and randomly fragmentated by $ZnCl_2$ (Sigma). After separation on the TBE-Urea PAGE gel, RNA fragments, visualized by ethidium bromide staining (used for all RNA gels) were sliced and extracted from the gel by crushing the gel and vigorously shaking (1400 rpm) at 70° C. in 400 μL of water for 15 min. The 3' ends were dephosphorylated by T4 Polynucleotide Kinase (New England Biolab). The miRNA cloning linker 2 (5'App/CACTCGGGCACCAAGGA/3'ddC (SEQ ID NO: 11), Integrated DNA Technologies) was used as the universal 3' linker and pre-adenylated using the 5' DNA Adenylation Kit (New England Biolab) with the provided protocol. Reverse transcription, self-circularization, and PCR amplification were performed essentially the same as previously described (McClary et al., Cell Chem Biol, 24, 605-613 e605 (2017)). Library sequencing was performed on Illumina NextSeq with single-end mode for up to 75 bp read length.

Data processing. Sequencing reads were processed by Cutadapt 2.10 (cutadapt.readthedocs.io/en/stable/) to remove 3' end linkers and then inputted into Shapemapper2 (Busan et al., RNA, 24 (2): 143-148 (2018)) to count the mutations and effective sequencing reads, using the STAR Aligner mode (Dobin et al., STAR: ultrafast universal RNA-seq aligner. *Bioinformatics.* 29:15-21 (2013)). The mutation rate of each nucleotide was calculated by dividing the number of the reads containing the mutations by the total number of reads, outputted as N.

For the PAL sample, the mutation rate fold change was calculated by dividing the mutation rate of the PAL sample by the mutation rate of the PRE sample. The average mutation count was calculated by averaging the number of mutations of the PAL and PRE samples. MA plots (FIG. 3A, FIG. 3B, FIG. 3C and FIG. 3D) were charted by plotting the mutation rate fold change of each nucleotide as a function of the average mutation count of each nucleotide. To determine possibly significant sites of AzAt labeling, the dataset was first screened for points that meet the criteria of a mutation rate fold change ≥1.5 and an average mutation count ≥100. Points meeting these criteria were further screened with Z-factor>0 and p-value<0.05 to determine statistical significance. The Z-factor (z) was calculated using the following equation $$z = 1 - \frac{1.96 \times (\sigma PAL + \sigma PRE)}{|\Delta N|}$$

wherein σ, the standard error of the mutation rate for a nucleotide is the square root of the mutation rate (M) divided by the read depth (C) and further normalized by the average mutation rate (A): σ=(M/C)/A and ΔN is the difference in the normalized mutation rate (N=M/A) between the PAL and PRE samples.

To determine the impact of UV treatment, the mutation rate fold change was calculated by dividing the mutation rate of the UV sample by the mutation rate of the NUL sample. The delta mutation rate (UV-NUL) was also calculated as an extra layer of filtering. Nucleotides having >10 UV/NUL, >0.01 (UV-NUL), and >100 average mutation counts were selected, and identified by sequence homology within the yeast rRNA sequence (Table 4). Native rRNA modifications within the Stop-POST5 (NUL) and 80S-IRES (NUL) samples having >0.2 average mutation rate were similarly identified within the yeast rRNA sequence (Table 3).

RNaseH Fragment Assay. Total RNA was prepared from the $^{3}$H-AzAt photoaffinity labeled ribosome by phenol-chloroform extraction. RNA:DNA duplexes were formed by incubating total RNA (0.2 μM) with an oligonucleotide pair (1 μM of each, sequences shown Table 1), flanking a specific RNA region, in 22.8 μL of water at 95° C. for 2 min, followed by annealing at 50° C. for 30 s and quenching on ice. Six units (1.2 μL) of RNase H (NEB) and 6 μl of 5× RNase H Reaction Buffer were next added to the RNA:DNA duplex and incubated at 37° C. for 1 hour, followed by phenol-chloroform extraction of RNA. The digested RNA was separated on 12% TBE-Urea PAGE gel, and the target band along with the adjacent upper and bottom gels were sliced by a 2 mm gel cutter. The gel slices were crushed and the $^{3}$H labeled rRNA fragment was extracted in water by vigorously shaking at 70° C. for 30 min, or by overnight extraction in elution buffer (0.3M sodium acetate, 0.25% SDS, 1 mM EDTA). The slurry was removed by centrifugation and the eluted $^{3}$H labeled rRNA in the supernatant was quantified. The stoichiometry of AzAt photoincorporation was calculated based on a gel recovery yield of 20±2%, determined using an authentic sample of [$^{3}$H]-Gln-tRNA$^{Gln}$.

TABLE 1

RNAse H oligonucleotide sequences for Fragments I-IV

| RNAse H Fragment | Oligo DNA sequences 5'-3' | SEQ ID NO: | Complementary to shrimp rRNA sequences |
|---|---|---|---|
| I | TCAATTCCTTTAA | 12 | 18S 1147-1159 |
| | GAGGTTTCCCGTGTTG | 13 | 18S 1204-1219 |
| II | CTCTTGCTTAAAACT | 14 | 26S 3064-3078 |
| | CTTGGCCGCCAC | 15 | 26S 3113-3124 |

TABLE 1-continued

RNAse H oligonucleotide sequences for Fragments I-IV

| RNAse H Fragment | Oligo DNA sequences 5'-3' | SEQ ID NO: | Complementary to shrimp rRNA sequences |
|---|---|---|---|
| III | GGCCCGTTCCCC | 16 | 26S 2636-2647 |
| | CTCCACAATACCG | 17 | 26S 2696-2708 |
| IV | CCGACCTCCATGG | 18 | 26S 1405-1417 |
| | GCCTCCCATTTTA | 19 | 26S 1467-1479 |

Plate Reader Anisotropy Assay

Plate reader assays were run in a Tecan F200® 96-well plate reader (Greiner® black, non-binding, chimney flat) equipped with 640 nm excitation and 700 nm polarization filters using 96-well plates. Atto(pep)-Stop-POST5 in Buffer 4 (0.1 μM, 80 μl) containing GTP (1 mM) was added to plate wells±ataluren at 25° C. eRF1 and eRF3 aliquots stored at −80° C. were thawed for 15 s at 37° C. and added directly to a premade ice-cold GTP (1 mM)±ataluren solution in Buffer 4. The resulting release factor solution was incubated at 25° C. for 1 min, and then added quickly in 80 μL portions to the Atto(pep)-Stop-POST5 containing wells with a multichannel pipette to the Atto(pep)-Stop-Post5 wells. The final concentrations were: eRF1, 0.025-0.4 μM; eRF3, 0.8 μM; Atto(pep)-Stop-Post5, 0.05 μM. Fluorescence anisotropy decay graphs were fit with GraphPad Prism, using the one phase decay model to obtain peptide dissociation rates.

Single Molecule Experiments

Preparation of PEG-passivated slides. PEG-passivated slides were prepared according to previously published procedures with minor modifications (Roy et al., *Nat. Methods,* 5, 507-516 (2008)). In brief, slides and coverslips were sonicated at 40° C. in the order of acetone (10 min), methanol (10 mins), 200 mM KOH (20 min), and ethanol (10 min). Cleaned slides and coverslips were treated in a fume hood with 1 ml 3-aminopropyltriethoxysilane, 5 ml acetic acid, in 94 ml methanol at room temperature overnight, sealed with parafilm, and then incubated with polyethylene glycol (PEG, Laysan Bio, Inc., containing 20% (w/w) mPEG succinimidyl valerate, MW 2000 and 1% biotin-PEG-SC, MW 2000) in 0.1 M sodium bicarbonate (pH 8.3) for 4 h. Slides and coverslips were then washed with Milli-Q water, dried by clean $N_2$, placed in 50 ml Falcon tubes, vacuum-sealed under $N_2$ in food saver bags, and stored at −20° C.

Flow chamber construction. The flow chambers for fast injection of reaction mixtures were made as described previously (Jamiolkowski et al., *Biophysical journal,* 113 (11), 2326-2335 (2017)). The sample flow chambers (8 μL) were formed on slides with holes drilled using a 1.25 mm diamond-tipped drill bit. Polyethylene tubing with 0.97 mm outer diameter (Warner Instruments) was inserted into each hole, sealed with 5 min epoxy and trimmed flush. Double-sided tape laid between the tubes served as spacers and separated the flow chambers. The coverslips were then sealed in place via the double-sided tape and epoxy at their edges.

Immobilization of ribosome Stop-POST 5 complexes. PEGylated flow chambers were incubated in 0.5 mg/ml streptavidin for 5 mins and washed with Buffer 4. Biotinylated Stop-POST5 containing FK (atto647) VRQ-tRNA$^{Gln}$ (Cy3) (SEQ ID NO: 24) in the P-site, was formed at room temperature by incubating Stop-POST4, eEF1A, GTP, and Gln-(Cy3) tRNA$^{Gln}$ for 5 mins and then injected into the streptavidin-coated slide chamber. After a 5 min incubation, excess unbound ribosome was flowed out. Then eRF1/eRF3±TRIDs was injected dynamically at 3 sec while recording. The injection dead time was subtracted for each particle.

Single-molecule fluorescence imaging. All sm-TIRF studies were carried out at 24° C. All dilutions, complex formation, and single-molecule imaging were carried out in Buffer 4 with an added enzymatic oxygen scavenging system of 2 mM protocatechuic acid (PCA), 50 nM protocatechunate 3,4 dioxygenase (PCD, Sigma Aldrich), 1 mM cyclooctatetraene (COT, Sigma Aldrich), 1 mM 4-nitrobenzyl alcohol (NBA, Sigma Aldrich), and 1.5 mM 6-hydroxy-2,5,7,8-tetramethyl-chromane-2-carboxylic acid (Trolox, Sigma-Aldrich) (Flis et al., *Cell reports,* 25 (10), 2676-2688 (2018).

Image stacks were recorded at 100 ms frame rate on a custom-built objective-type total internal reflection fluorescence (TIRF) microscope based on a commercial inverted microscope (Eclipse Ti-E, Nikon) and capable of performing alternating-laser excitation (ALEX) between 532 nm and 640 nm laser beams using an acousto-optic tunable filter (AOTF, Chen et al., 2011). For the time-lapse experiment, timing of the movies, programmed into NIS-Elements (Nikon) microscope software, were recorded by illuminating the sample for 50-20 frames at 10 frames per s with 15 s or 24 s intervening dark intervals. Video recording was started and then eRF1/eRF3±TRIDs was injected from a triggered syringe pump at 3 sec while recording. The injection dead time was subtracted for each particle. Triggering of the shutters, AOTF, and pump was synchronized using LabView scripts driven from the camera exposure signal.

Data analysis. Collected movies were analyzed by a custom-made software program developed as an ImageJ plugin (Chen et al., *Mol. Cell,* 42, 367-377 (2011)), and further analyzed using Python. Distributions of peptide and tRNA dissociation times were fit to eq (5), using maximum likelihood estimation (Bevington and Robinson. Data Reduction and Error Analysis for the Physical Sciences. New York: McGraw-Hill, (2002); Woody et al., *Biophys. J.* 111, 273-282 (2016)), where P is the probability density.

$$P = k_1 e^{-k_1 t} \quad (5)$$

Data and fitted curves were plotted as cumulative probability densities.

Example 1. Photoaffinity Labeling (PAL) Experiments Identify Functionally Significant RNA Sites AzAt mimics ataluren in stimulating readthrough of a premature stop codon (FIG. 2) and in inhibiting eRF1/eRF3-catalyzed termination at a premature stop codon (Ng et al., *Proc Natl Acad Sci USA,* 118: e2020599118 (2021), incorporated by reference herein in its entirety), showing a significantly lower EC50 than ataluren in both assays. Photochemical experiments on aryl azides have demonstrated that photolysis of a phenyl azide rapidly forms (in ≤20 ns) either a ketenimine or azepinone intermediate, that reacts with nucleophiles in approximately 100 μs, and is quenched by an amine-containing buffer (Buchmueller et al., *J Am Chem Soc.* September 10; 125 (36): 10850-61 (2003)). Such quenching minimizes photoincoporation into a biological target resulting from azide photolysis occurring in solution. PAL experiments with [$^3$H]-AzAt were carried out in order to identify the binding sites of ataluren within the protein synthesis apparatus of the PURE-LITE system. Separately, AzAt-PAL experiments were performed on two targets, the Stop-POST5 complex and the eRF1.eRF3.GDPNP ternary complex.

Photoincorporation into Stop-POST5 as a function of AzAt concentration (FIG. 2B) resulted in a sigmoidal curve. Fitting the curve to eq (1), where PI is equal to the measured AzAt photoincorporation, yielded a $K_A$ equal to 120±60 UM and a Hill n of 3±1.

$$PI = \frac{PI_{max}[AzAt]^n}{(K_A^n + [AzAt]^n)} \tag{1}$$

More than 80% of the photoincorporation was found in the RNA components of Stop-POST5, comprising six RNA species (26S rRNA, 18S rRNA, 5.8S rRNA, 5S rRNA mRNA, and tRNA). As determined by urea-PAGE analysis >90% of the RNA photoincorporation is found within the 18S and 26S rRNA, with the remainder distributed among the smaller RNAs (Table 2).

such photoincorporation was due to either a very weak site binding or to reaction with AzAt photolyzed in solution before binding since it increased in a strictly linearly fashion up to an AzAt concentration of 500 μM. Photoincorporation into eRF3 was strongly inhibited within the ternary complex (FIG. 2F), perhaps due to surface residues in isolated eRF3 becoming buried within the ternary complex.

Identifying Functionally Significant RNA Sites Photolabeled by AzAt

A combination of LASER-Seq and an RNAse H fragment assay was employed to identify functionally significant nucleotides photolabeled by AzAt. Each of these nucleotides were found within the large rRNAs, as described below. Results obtained at other nucleotides, including all of the smaller RNAs, were not functionally significant, as demonstrated in Example 3.

Using RNA-seq mutational profiling to identify nucleotides photolabeled via nitrene formation. The dominance of AzAt photoincorporation into the RNA fraction of both Stop-POST5 and 80S.IRES complexes indicated the use of LASER-seq (Zinshteyn et al., *Nucleic Acids Res*, 47, 43-55 (2019)) would be useful to identify the sites of AzAt

TABLE 2

Photoincorporation yields (mole %) into Small RNAs within Stop-POST5 complex

| Experiment | Competing Ligand[a] | CrPV-IRES nts1-155 | CrPV-IRES nts156-221 | CrPV-IRES nts222-278 | CrPV-IRES All | 5.8S rRNA | 5S rRNA | $tRNA^{Gln}$ |
|---|---|---|---|---|---|---|---|---|
| PAL, | — | 7.6 ± 1.5 | 3.2 ± 0.8 | 0.02 ± 0.03 | 7.3 ± 0.5 | 0.89 ± 0.10 | 1.62 ± 0.11 | 2.3 ± 0.2 |
| 300 μM | eRF1/eRF3/ | 4.6 ± 1.4 | 2.9 ± 0.6 | 0.08 ± 0.11 | 5.4 ± 0.6 | 0.80 ± 0.02 | 1.3 ± 0.2 | 2.2 ± 0.2 |
| AzAt | GDPNP | | | | | | | |
| PAL, | — | 0.56 ± 0.04 | 0.23 ± 0.08 | 0.06 ± 0.04 | 0.85 ± 0.14 | 0.25 ± 0.01 | 0.19 ± 0.01 | 0.30 ± 0.04 |
| 30 μM | Ataluren | 0.40 ± 0.13 | 0.17 ± 0.03 | 0.07 ± 0.06 | 0.76 ± 0.05 | 0.19 ± 0.01 | 0.15 ± 0.01 | 0.22 ± 0.03 |
| AzAt | GJ072 | 0.51 ± 0.03 | 0.22 ± 0.05 | 0.09 ± 0.05 | 0.59 ± 0.14 | 0.19 ± 0.07 | 0.15 ± 0.01 | 0.25 ± 0.03 |
| PRE, | — | 0.02 ± 0.01 | 0.05 ± 0.04 | 0.03 ± 0.01 | 0.02 ± 0.01 | 0.02 ± 0.01 | 0.02 ± 0.01 | 0.41 ± 0.09 |
| 300 μM | | | | | | | | |
| AzAt | | | | | | | | |

Figure 2A:
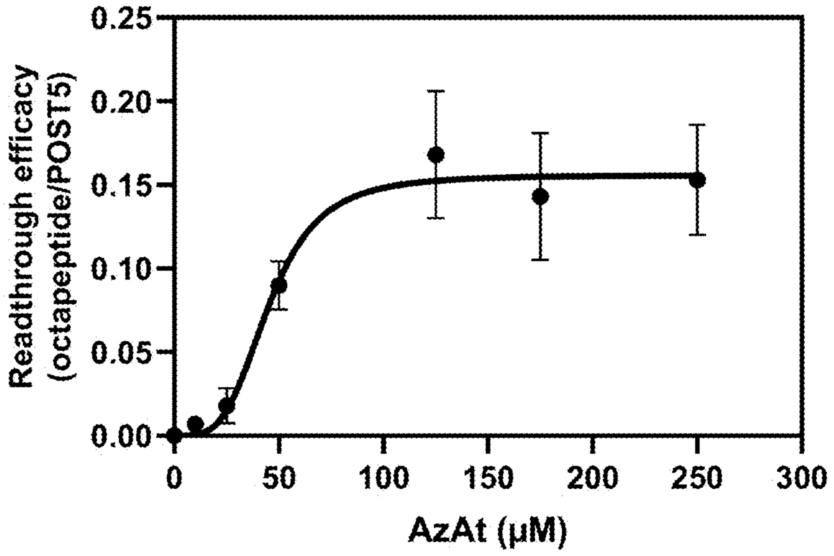
FIG. 2A, FIG. 2B, FIG. 2C, FIG. 2D, FIG. 2E, and FIG. 2F are graphs showing AzAt Photoaffinity Labeling and binding.
Figure 2B:
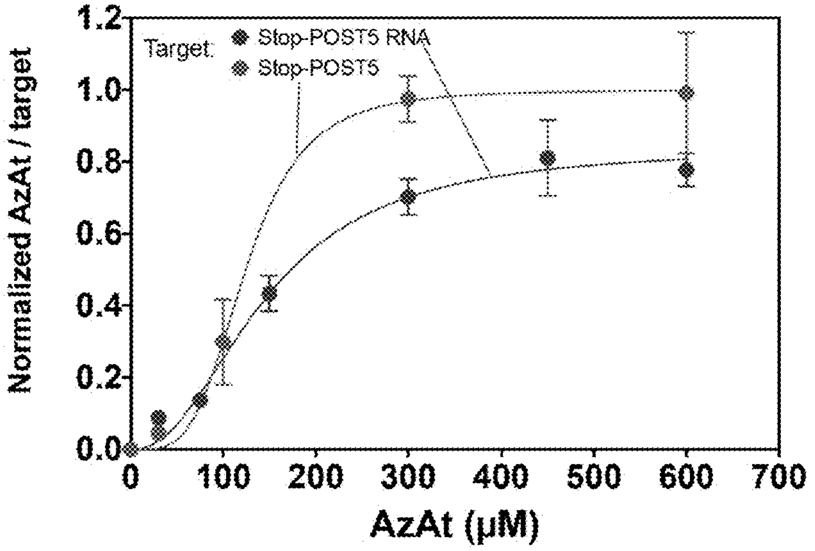
Figure 2C:
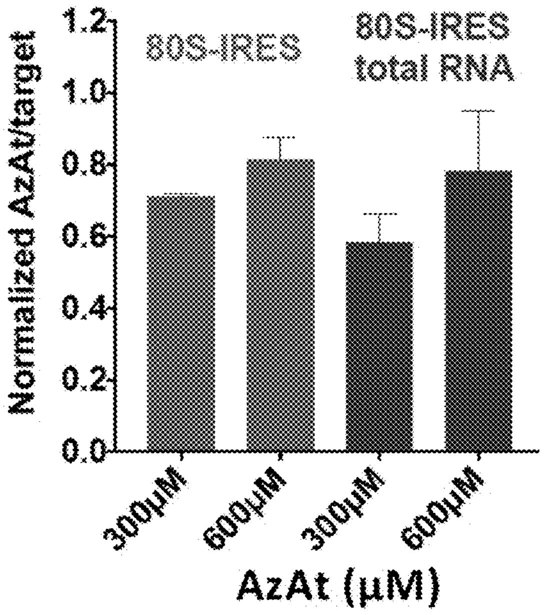

[a]Added concentrations: eRF1, 2 μM; eRF3, 4 μM; Ataluren, 500 μM; GJ072, 150 μM; GDPNP, 1 mM The preparation of Stop-POST5 had a stoichiometry of 0.40=0.05 PheLysValArgGln-$tRNA^{Gln}$ (SEQ ID NO: 25)/ribosome, with the remainder of the ribosome population consisting of an 80S.IRES complex. In a separate photoincorporation experiment it was determined that AzAt photoincorporation into the 80S.IRES complex itself proceeded with a 25% lower stoichiometry vs. the photoincorporation into Stop-POST5 (FIG. 2C).

Figure 2D:
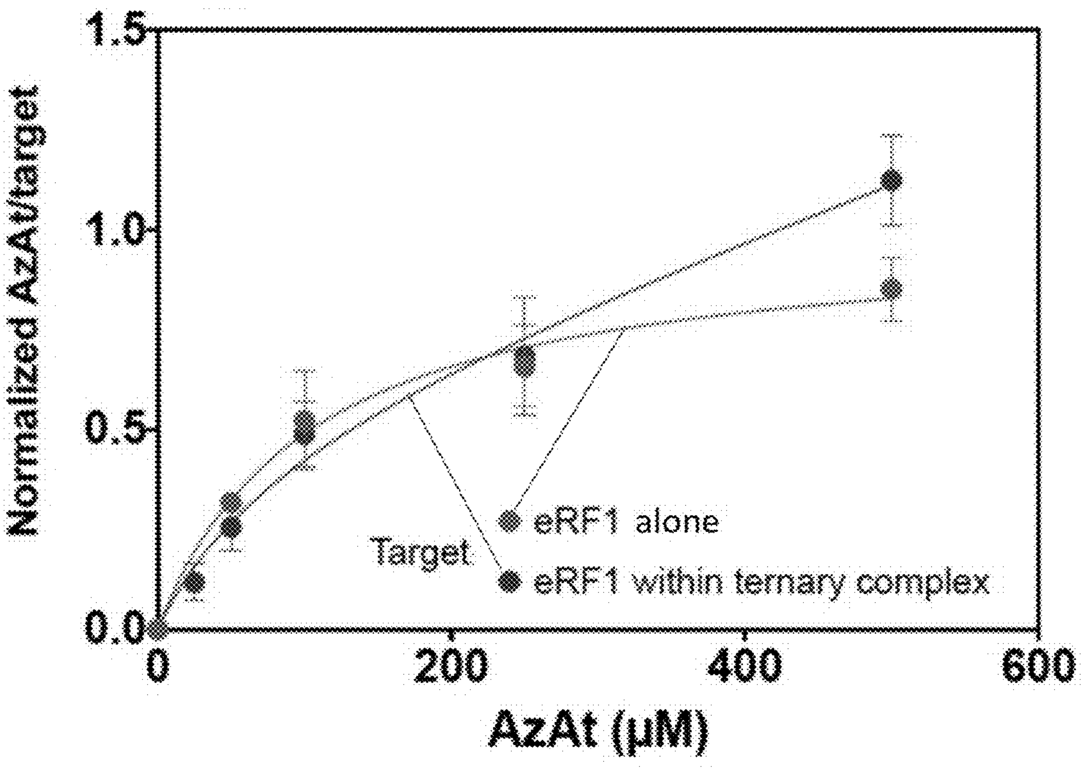
Figure 2E:
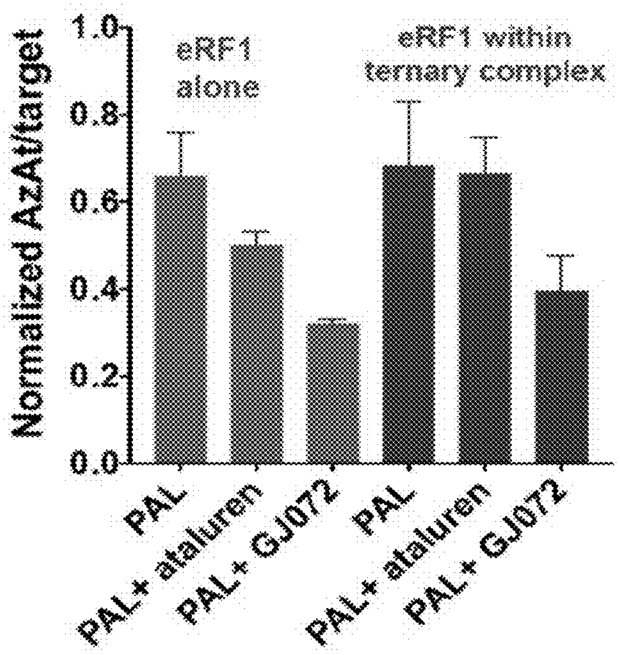
Figure 2F:
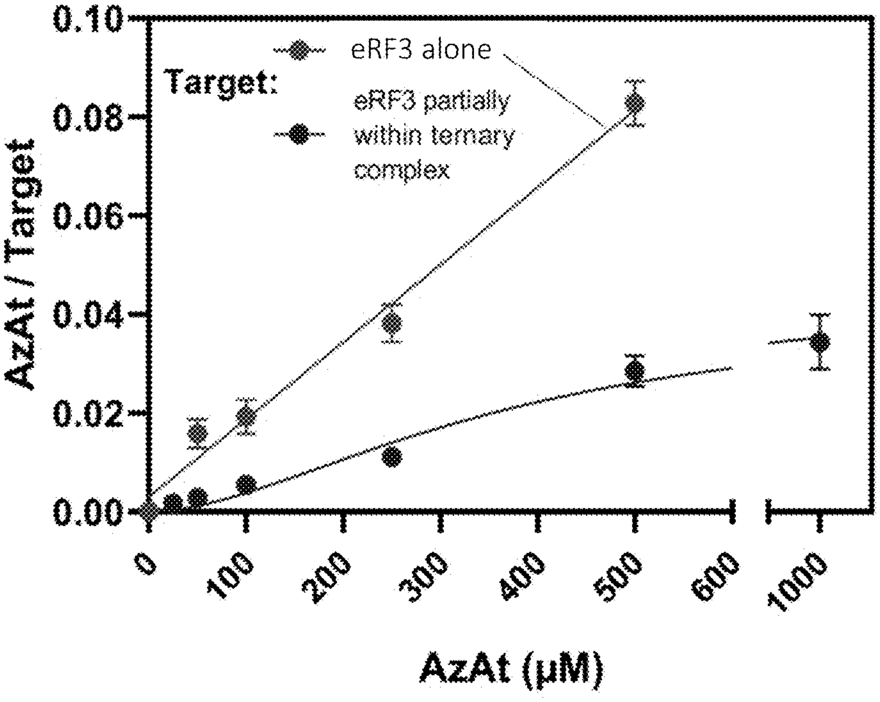
Figure 2G:
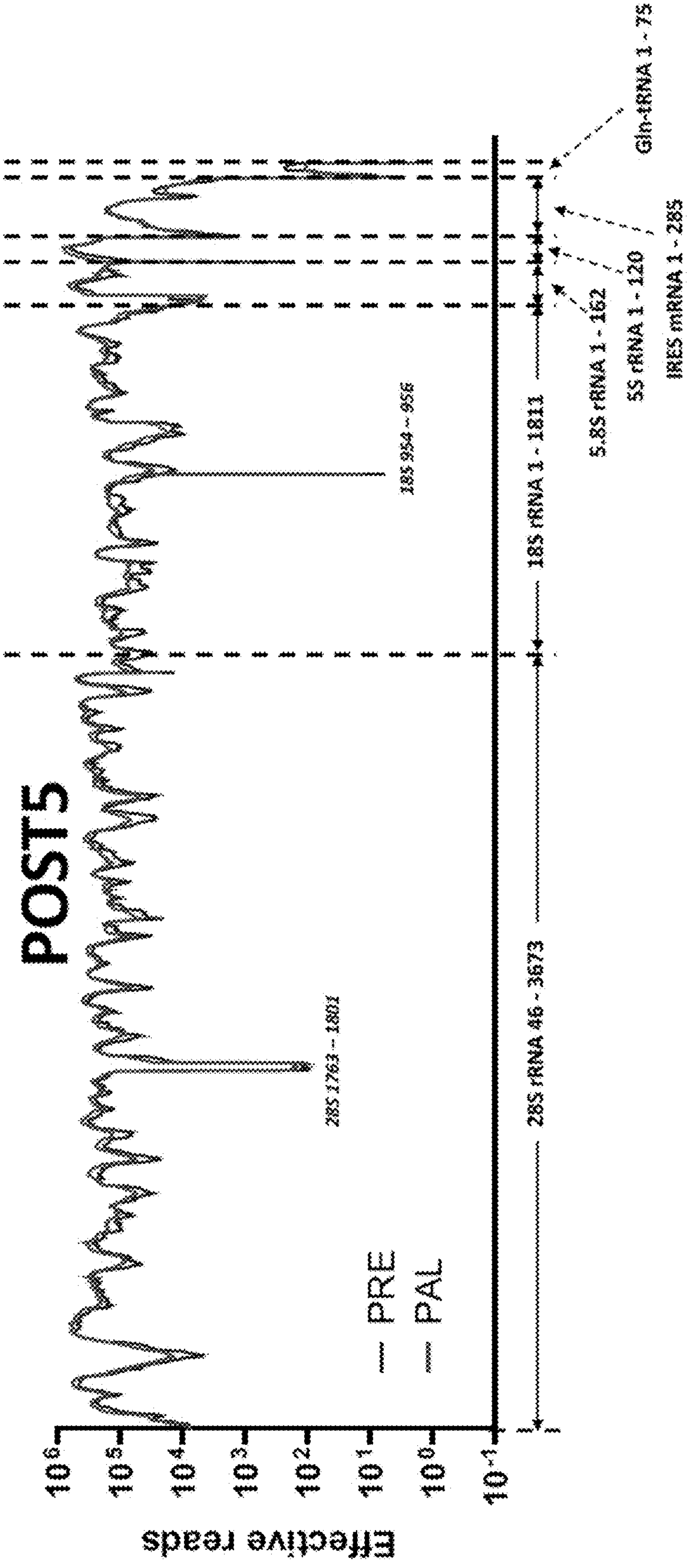
FIG. 2G and FIG. 2H are graphs showing the RNA-seq reads coverage as the effective reads per nucleotide. PRE: treated with 300 μM prephotolysed AzAt; PAL: treated with 300 μM AzAt. 26S-IRNA nucleotides 1-45 were unable to be mapped due to the lack of sequence information. Regions that are not sufficiently covered by sequencing are annotated (26S 1763-1801, 18S 954-956). The Gln-tRNA was not covered by the RNA-seq due to its short length sequence.
Figure 2H:
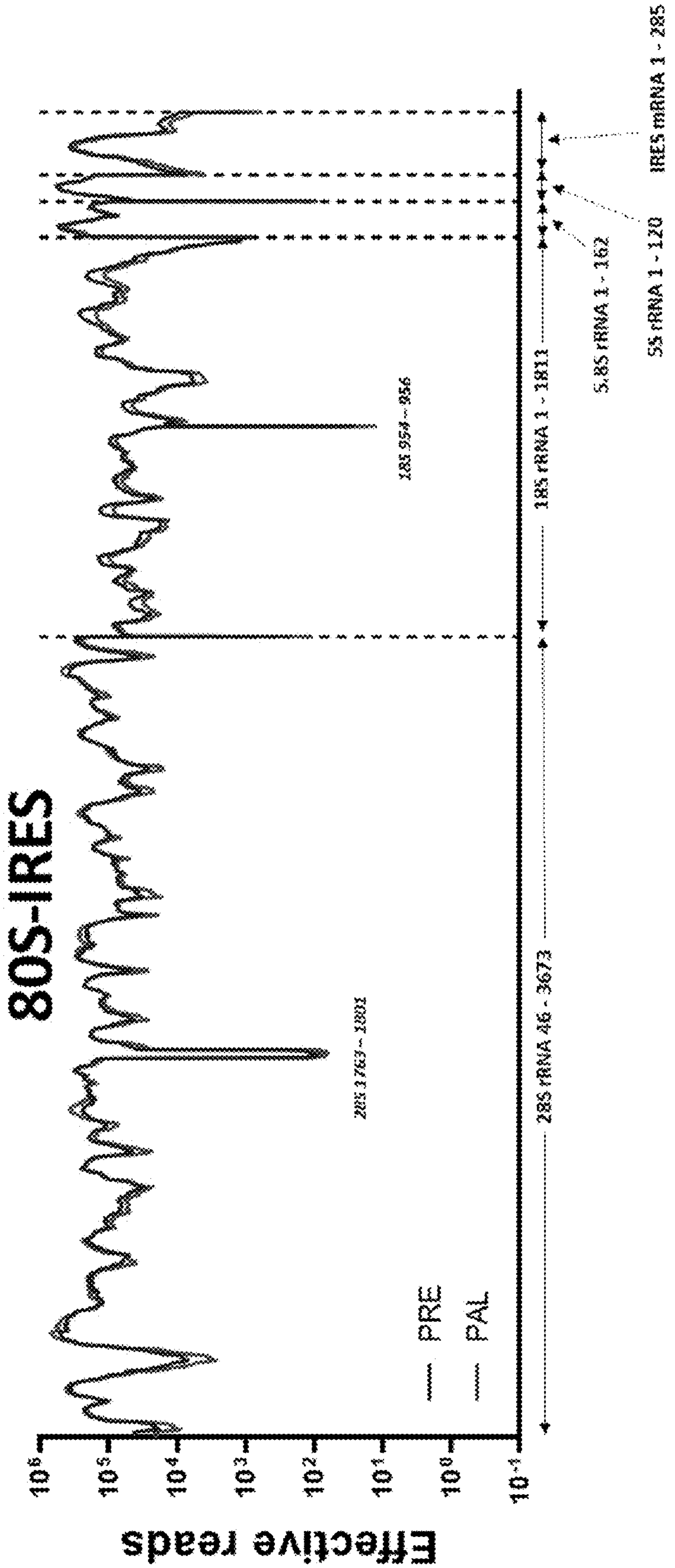

AzAt photoincorporation into either eRF1 or eRF3.GDPNP alone, or into the eRF1.eRF3.GDPNP ternary complex was also measured (FIG. 2D). Photoincorporation into isolated eRF1 as a function of AzAt concentration resulted in a simple hyperbolic saturation curve with a $K_d$ of 110±20 μM. The corresponding experiment performed on eRF1 within the eRF1.eRF3.GDPNP ternary complex showed biphasic behavior, consistent with a tight binding site and a much weaker site. The tight site photoincorporation proceeded with a $K_d$ value of 90±20 μM, indistinguishable from that found with isolated eRF1. Significantly, both ataluren and GJ072, an ataluren-like TRID (Ng et al., *ACS Med Chem Lett,* 9, 1285-1291 (2018); Ng et al., *Proc Natl Acad Sci USA,* 118: e2020599118 (2021), incorporated by reference herein in its entirety), substantially inhibited AzAt photoincorporation into isolated eRF1, although the inhibition was less marked within the ternary complex (FIG. 2E). AzAt also photoincorporated into isolated eRF3. However, photoincorporation into RNA. In this method, modified nucleotides show up as point mutations introduced during reverse transcription.

For each complex LASER-Seq was carried out on four types of samples, denoted PAL, PRE, UV, and NUL. PAL samples were prepared by photoaffinity labeling of complexes with 300 μM AzAt, a concentration close to saturating for photoincorporation (FIG. 2C). PRE samples were prepared using separately prephotolyzed AzAt that was re-irradiated in the presence of complexes. UV and NUL samples were prepared in the absence of AzAt by either subjecting complexes to uv irradiation (UV) or just analyzing complexes directly (NUL).

LASER-Seq reads coverages were virtually identical for all samples (FIGS. 2G and 2H) with, in each case, over 97% of the nucleotides giving at least 10,000 reads. Notable exceptions were $tRNA^{Gln}$, 26S rRNA 1763-1801 and 18S rRNA 954-956 which gave very low reads and were excluded from downstream analysis. Very high mutation rates (28%-100%) were found in 10 nucleotides in all samples (Table 3). Three of these nucleotides have previously been reported to be modified at the conserved sites in *S. cerevisiae* (25S-2870, $m^5C$: 18S-1191, $m^1acp^3\Psi$ (18): 25S-A645; $m^1A$, (19)) two of which were also reported in human rRNA (28S-A1314, Am: 18S-U1248, $m^1acp^3\Psi$ (20)). There were also seven additional modified nucleotides. In addition, relatively high mutation rates (1.8%-9.9%) were found in 14 nucleotides in the PAL, PRE, and UV samples (Table 4), which likely include sites of uv-induced crosslinking (Zhirnov et al., *Photochem Photobiol Sci*. June; 2 (6): 688-93 (2003)), and were not seen in the NUL samples.

$$FI(\text{Stop}-\text{POST5})_{corrtd} = 2.5\{FI(\text{Stop}-\text{POST5})_{measured} - 0.6FI(80S\cdot IRES)_{measured}\} \quad (2)$$

TABLE 3

Native chemical modification on shrimp cyst rRNA detected by RNA-seq

| Shrimp rRNA numbering | Yeast rRNA numbering | Human rRNA numbering | Average mutation rate in untreated samples | Reported modification in yeast rRNA[a] | Reported modification in human rRNA |
|---|---|---|---|---|---|
| 18S-C953 | Insertion between 18S-939 and 18S-940 | 18S-A998 | 1.00 | None | None |
| 18S-G1734 | 18S-U1723 | 18S-G1792 | 0.99 | None | None |
| 5.8S-G120 | 5.8S-U127 | 5.8S-G115 | 0.96 | None | None |
| 18S-G231 | 18S-U229 | 18S-U250 | 0.95 | None | None |
| 26S-C3156 | 25S-C2870 | 28S-C4432 | 0.95 | m5C | None |
| 26S-A764 | 25S-A645 | 28S-A1314 | 0.94 | m1A | Am |
| 18S-U1706 | 18S-U1710 | 18S-C1766 | 0.86 | None | None |
| 18S-U1203 | 18S-U1191 | 18S-U1248 | 0.80 | m1acp3Ψ | m1acp3Ψ |
| 26S-U3239 | 25S-U2953 | 28S-U4515 | 0.58 | None | None |
| 26S-G1801 | 25S-G1576 | 28S-U2480 | 0.28 | None | None |

[a]m5C: 5-methylcytidine; Am: 2' -O-methyladenosine; m1acp3Ψ: 1-methyl-3-(3-amino-3-carboxypropyl)pseudouridine

TABLE 4 rRNA nucleotides susceptible to UV irradiation

| Shrimp rRNA numbering | Yeast rRNA numbering | Mutation rate fold change (UV/NULL) | Delta mutation rate (UV-NULL) |
|---|---|---|---|
| 26S-415 | 25S-394 | 26.4 | 0.043 |
| 26S-420 | 25S-399 | 22.8 | 0.018 |
| 26S-836 | 25S-714 | 20.7 | 0.036 |
| 26S-1833 | 25S-1602 | 16.7 | 0.027 |
| 26S-422 | 25S-401 | 14.6 | 0.019 |
| 26S-3008 | 25S-2723 | 13.9 | 0.092 |
| 26S-459 | 25S-429 | 13.5 | 0.060 |
| 26S-3092 | 25S-2807 | 13.1 | 0.018 |
| 26S-2458 | 25S-2190 | 12.9 | 0.043 |
| 18S-120 | 18S-121 | 12.7 | 0.060 |
| 18S-454 | 18S-449 | 12.5 | 0.032 |
| 26S-391 | 25S-370 | 11.7 | 0.033 |
| 28S-1688 | 25S-1495 | 10.7 | 0.027 |
| 28S-3010 | 25S-2725 | 10.1 | 0.054 |

The sites of modification arising exclusively via nitrene formation on irradiation of AzAt was first identified by the mutation rate fold change of PAL vs. PRE samples, a procedure which corrects for mutation rates arising from noncovalent binding, or covalent photoincorporation of prephotolyzed AzAt, or uv-induced mutations not related to AzAt (Table 4). The results obtained for the ≥6,006 nucleotides present in these two complexes are presented in FIG. 3A, FIG. 3B, FIG. 3C and FIG. 3D. In examining these data sets to identify potentially interesting sites of AzAt labeling of Stop-POST5 complex and 80S.IRES complex, constraints were imposed that the fold-increase (FI) was ≥1.5, that there ≥100 reads for each mutated site, and that the results were statistically significant (Z-factor >0 and p-value <0.05). These constraints narrowed the number of potentially interesting sites to the 22 identified in FIG. 3E. In this Figure, the FIs for 80S.IRES complex were measured directly, but the FIs shown for the Stop-POST5 complex are values calculated using eq (2), which corrects for the fraction of 80.IRES complex (0.60±0.05) present in the Stop-POST5 preparation.

Strikingly, nucleotide 18S-A1195 of 18S rRNA had by far the highest fold-increase (~9-fold) in both complexes, showing that it arises from a site present in both complexes. Also noteworthy are several nucleotides, including 26S-A3093, 26S-A2752, 26S-A3557, IRES-U177 and 18S-A699 having FI values which are strongly enhanced in the Stop-POST5 complex vs. the 80S.IRES complex. The large number of nucleotides of potential interest identified in FIG. 3E raised the question of which are most likely pertinent for understanding ataluren inhibition of release factor activity.

Figure 4:
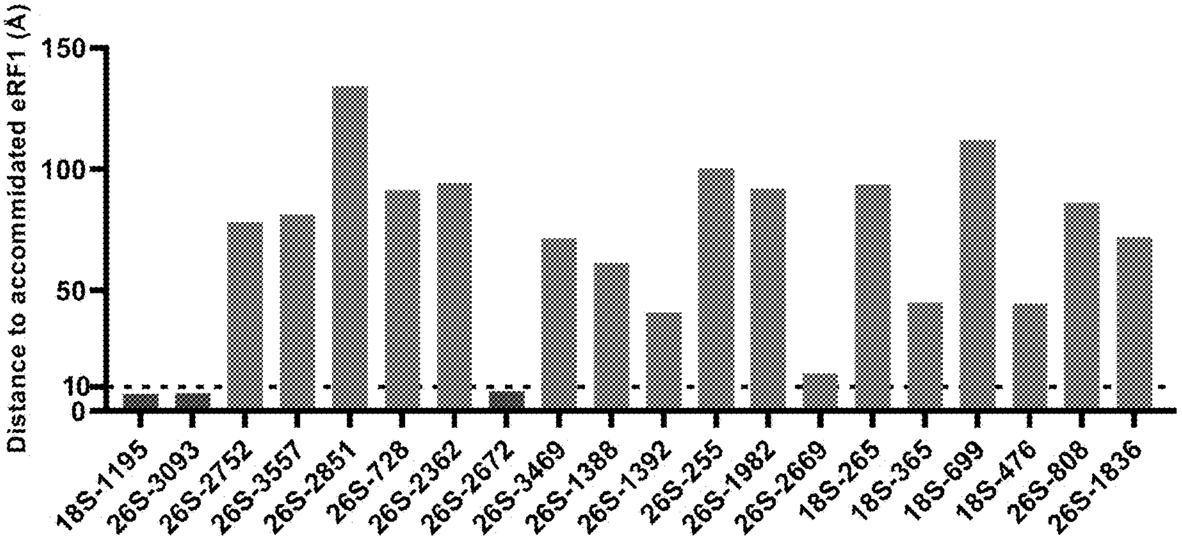
FIG. 4 is a graph showing Measured distance between the selected nucleotides and the fully accommodated eRF1 (pdb: 5LZU). Nucleotides that fall within 10 angstrom distance are shown as bars below the dotted line.
Figure 5A:
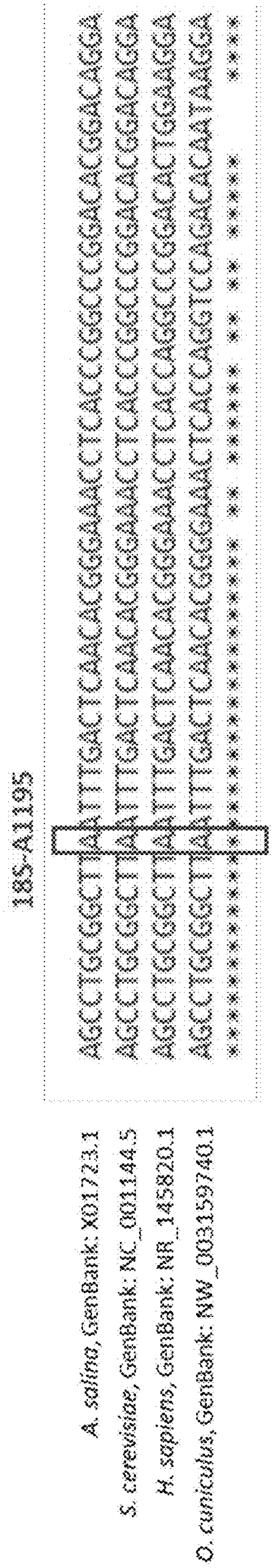
FIG. 5A, FIG. 5B, and FIG. 5C show conserved nucleotides in sequence alignments between regions from Genbank numbers X01723.1 (SEQ ID NO: 1), NC_001144.5 (SEQ ID NO: 2), NR_145820.1 (SEQ ID NO: 3), NW_003159740.1 (SEQ ID NO: 4) in FIG. 5A, between regions from Genbank numbers AY210805.1 (SEQ ID NO: 5), NC_001144.5 (SEQ ID NO: 6), and NR_146154.1 (SEQ ID NO: 7) in FIG. 5B, and between regions from Genbank numbers AY210805.1 (SEQ ID NO: 8), NC_001144.5 (SEQ ID NO: 9), and NR_146154.1 (SEQ ID NO: 10) in FIG. 5C. Conservation analysis shows that the four nucleotides of interest are all located at highly conserved regions of rRNA. Star symbols indicate identical sequences from different species.
Figure 5B:
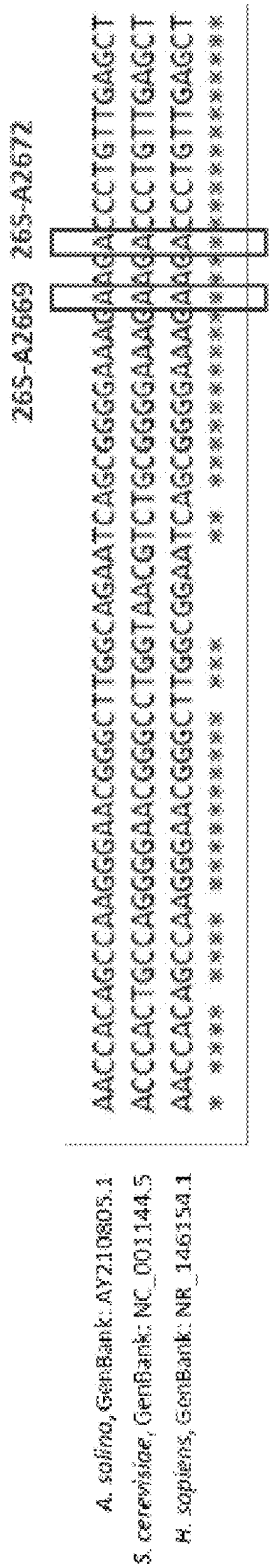
Figure 5C:
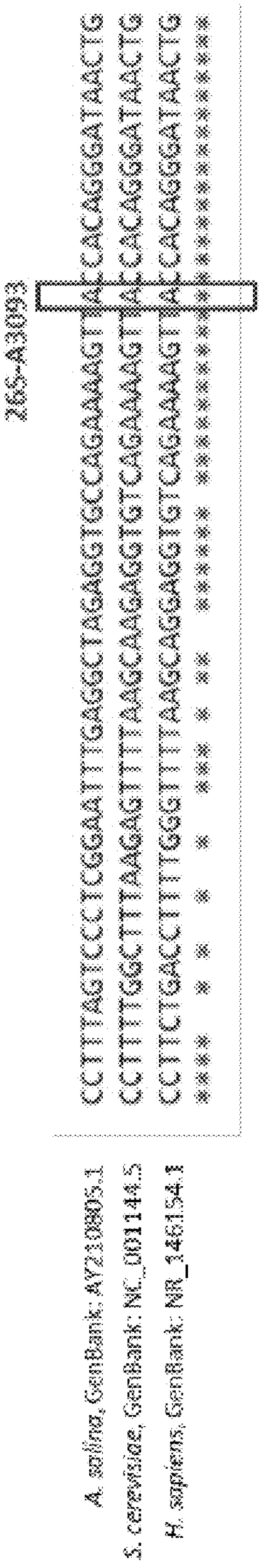
Figure 6A:
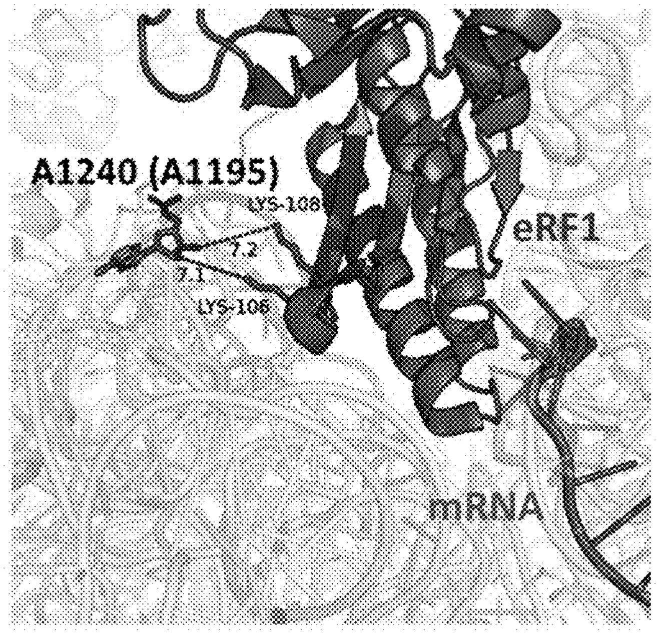
FIG. 6A, FIG. 6B, and FIG. 6C are diagrams showing the location of nucleotides of interest.
Figure 6B:
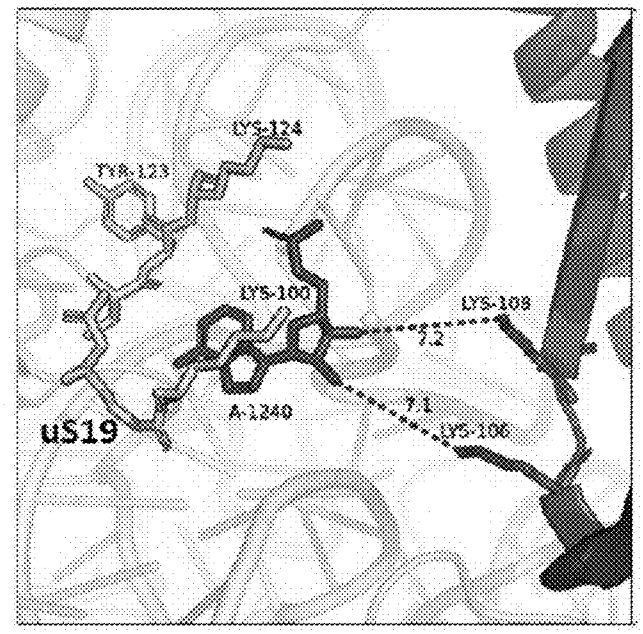
Figure 6C:
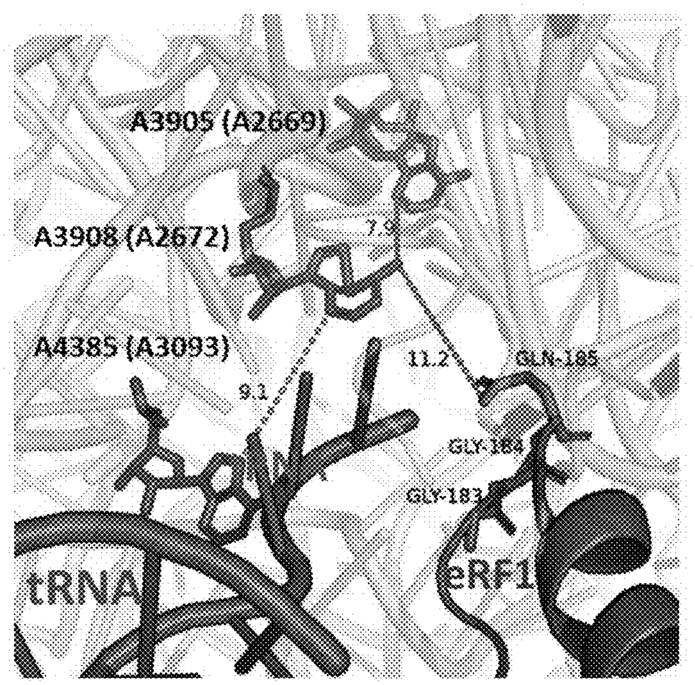

To address this question, the structure of the fully accommodated eRF1 bound to a termination complex of the rabbit ribosome (PDB: 5LZU) as a reference was used to identify nucleotides labeled by AzAt which are proximal (within 10 Å) of eRF1. The large majority of the nucleotides in FIG. 3E fell outside this limit (FIG. 4) and were located at peripheral and flexible loop regions with low evolutionary conservation among eukaryotic species, suggesting that they represent non-specific or functionally irrelevant photoincorporations of AzAt. However, three labeled nucleotides, 18S-A1195, 28S-A3093 and 28S-A2672, indicated with asterisks in FIG. 3E, were proximal to eRF1 and fell within highly conserved and functional regions of rRNA (FIG. 5A, FIG. 5B, and FIG. 5C). 18S-A1195 is proximal to the segment of eRF1 that binds to the termination codon during translation termination (FIG. 6A), is part of the conserved helix 31 loop region, and forms a polar pocket with Tyr123, Lys124, and Lys100 of r-protein uS19 (FIG. 6B), a component of the decoding center that is functionally involved in multiple states of translation elongation (Bhaskar et al., *Cell Rep*, 31, 107473 (2020)). As shown in FIG. 6C, 28S-A3093 and 28S-A2672 are clustered at the peptidyl transferase center (PTC), in the vicinity of the catalytically important GGQ motif of eRF1, and extending towards the peptide exit tunnel. Also labeled in FIG. 6C is 28S-A2669 (indicated with an x in FIG. 3E) which, while just outside the 10 Å eRF1 distance limit (FIG. 4), lies within the PTC and is proximal to 28S-A3093 and 28S-A2672.

Testing the functional pertinence of AzAt photolabeling of 18S-A1195, 28S-A3093, 28S-A2672, and 28S-2669. An RNAse H fragment assay was employed to determine whether the potential functionally significant sites identified by LASER-seq correspond to ataluren binding sites relevant for termination activity. In this assay, oligonucleotide hybridization, RNase H digestion and polyacrylamide gel electrophoresis (PAGE) were used to determine the stoichiometry of [$^3$H]-AzAt photoincorporation into the three IRNA fragments that together include the four nucleotides of interest: Fragment I, 18S-A1195; Fragment II, 26S-A3093; Fragment III, 26S-A2669 and 26S-A2672 (Table 5). The separate addition of four potential competitors of AzAt binding (eRF1 alone, the stably bound eRF1.eRF3.GDPNP complex, ataluren, and the ataluren-like TRID GJ072) was used to test how these affected such photoincorporation. These experiments, the results of which are summarized in Table 5, were performed at two different AzAt concentrations. eRF1 and eRF1.eRF3.GDPNP effects were measured using 300 μM AzAt, paralleling the LASER-Seq PAL experiments. In contrast, 30 μM AzAt was used to measure ataluren and GJ072 effects, because of the expectation that inhibition would be incomplete at high AzAt concentration, based on the relative EC50 values of ataluren >AzAt ~GJ072 as termination inhibitors (Ng et al., *Proc Natl Acad Sci USA,* 118: e2020599118 (2021)) and the limited solubility of GJ072 in aqueous medium.

Both eRF1 alone and eRF1.eRF3.GDPNP strongly inhibited AzAt photoincorporation into Fragments I, II, and III derived from the Stop-POST5 complex, with the effects on Fragments I and III being particularly pronounced. In contrast, for the 80S.IRES complex, added eRF1.eRF3.GDPNP showed essentially no inhibition of AzAt photoincorporation into Fragments II and III and only partial inhibition of photoincorporation into Fragment I. These results reflected the expected weaker binding of release factors to the ribosome in the absence of a stop codon at the A-site, and they also show that such weaker binding is not accompanied by a conformational change that results in eRF1 interaction with the PTC.

Photoincorporation into Fragment I derived from Stop-POST5 complex was also strongly inhibited by ataluren and GJ072. Taken together, the results in Table 5, along with the placement of 18S A1195 shown in FIG. 6C, provide strong evidence that 18S A1195 was labeled from a functionally important ataluren binding site that was blocked by eRF1 or eRF1.eRF3.GDPNP binding. However, photoincorporation into Fragment III, reflecting A2669/A2672 photolabeling, was only weakly inhibited by ataluren and GJ072, and photoincorporation into Fragment II, reflecting A3093 photolabeling, was actually stimulated. These results could indicate that photolabeling of the PTC sites does not proceed from a true ataluren binding site, but an alternative interpretation is that the results arise from two opposite effects: a direct competition by ataluren and GJ072 with AzAt at the PTC and an allosteric stimulation of AzAt binding at the PTC by ataluren or GJ072 binding elsewhere within the ribosome.

Figure 7A:
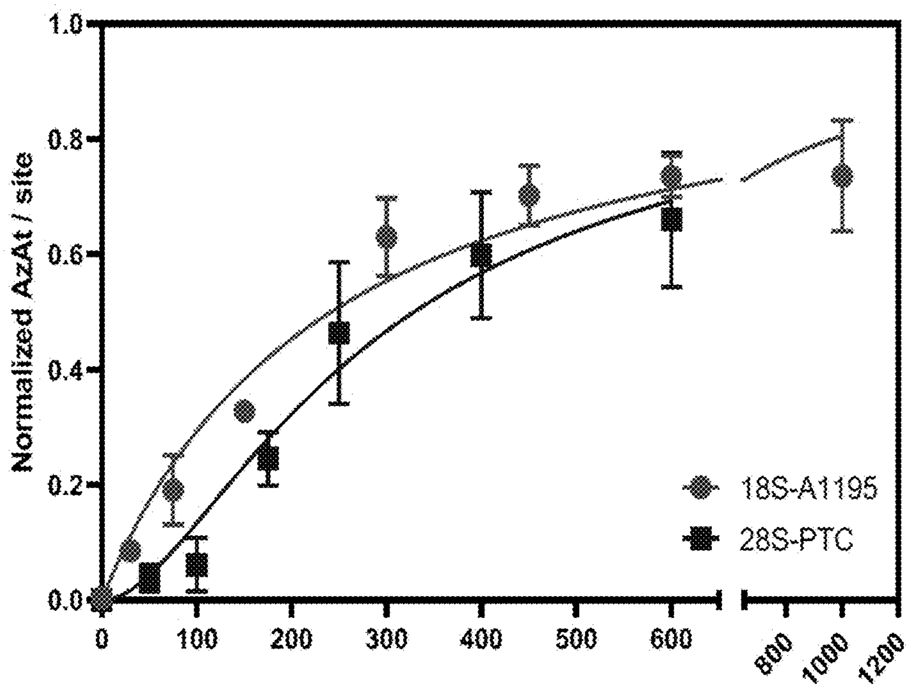
FIG. 7A is a graph showing saturation curves for photoincorporation into 18S-A1195, as measured by photoincorporation into Fragment I vs. the sum of the photoincorporations into 26S A2669, A2672, and A3093, as measured by photoincorporation into Fragments II and III.
Figure 7B:
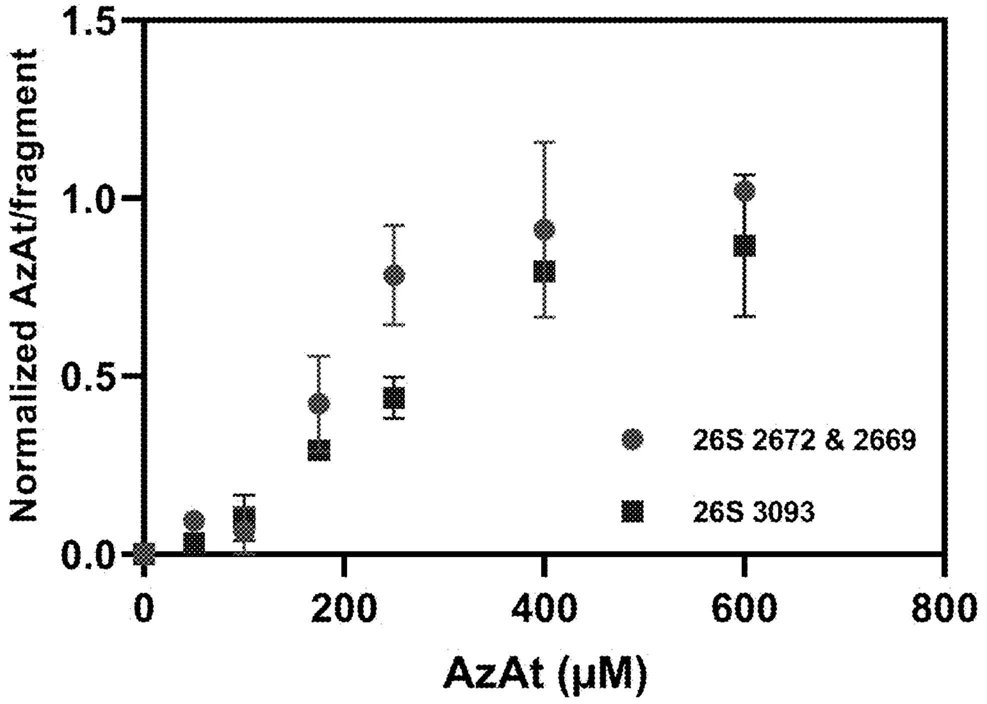
FIG. 7B is a graph showing concentration-dependent of AzAt photoincorporation into Fragment II (including 26S 3093) and III (including 26S-A2672 and 26S-A2669). The saturating values were 0.8% for both Fragment II and Fragment III. The S-shaped concentration dependence is evident for both fragments.

To resolve this question, the AzAt concentration dependence of photoincorporation into these PTC sites (Fragments II and III) and into A1195 (Fragment I) was determined. It was found that photoincorporation into Fragment 1 can be fit to a simple hyperbolic binding isotherm with an apparent $K_D$ of 240±10 μM (FIG. 7A), but that photoincorporation into Fragments II and III both show clear evidence of cooperativity, with shapes that are quite similar to one another (FIG. 7B). This latter result, and the mutual proximities of 26S-A3093, 28S-A2672, and 28S-2669 (FIG. 2H), showed that photoincorporation into these three nucleotides occurred from a single binding site within the PTC. Accordingly, in FIG. 7A the normalized values of the combined saturation curve for Fragments II and III were compared with the normalized values for the saturation curve of Fragment I, showing the clear difference in the shape of the curves. Fitting the saturation curve for Fragments II and III to eq (1) yielded a $K_A$ equal to 200±40 μM and a Hill n of 3.3±0.2.

TABLE 5

Photoincorporation yields (mole %).
Photoincorporation yields (mole %) into RNAse H Fragments

| | | | Mutated site(s)/RNAse Fragment | | |
|---|---|---|---|---|---|
| Target | Experiment | Competing Ligand[a] | 18S A1195/ I: 18S 1151-1206 | 26S-A3093/ II: 26S 3069-3113 | 26S-A2669;A2672/ III: 26S 2638-2702 |
| Stop-POST5 | PAL, | — | 1.55 ± 0.20 | 0.40 ± 0.01 | 1.07 ± 0.14 |
| | 300 μM AzAt | eRF1 | 0.19 ± 0.07 | 0.18 ± 0.01 | 0.20 ± 0.01 |
| | | eRF1/eRF3/GDPNP | 0.07 ± 0.03 | 0.18 ± 0.10 | 0.19 ± 0.02 |
| | PAL, | — | 0.26 ± 0.03 | 0.03 ± 0.01 | 0.13 ± 0.04 |
| | 30 μM AzAt | Ataluren, 500 μM | 0.06 ± 0.01 | 0.06 ± 0.01 | 0.10 ± 0.04 |
| | | GJ072, 150 μM | 0.10 ± 0.01 | 0.07 ± 0.01 | 0.07 ± 0.01 |
| | PRE, 300 μM AzAt | — | 0.012 ± 0.003 | 0.04 ± 0.01 | 0.03 ± 0.02 |
| 80S-IRES | PAL, | — | 1.03 ± 0.33 | 0.50 ± 0.09 | 1.01 ± 0.12 |
| | 300 μM AzAt | eRF1/eRF3/GDPNP | 0.56 ± 0.06 | 0.55 ± 0.12 | 0.94 ± 0.23 |

[a]Added concentrations: eRF1, 2 μM; eRF3, 4 μM; GDPNP, 1 mM

Example 2 Ataluren is an Apparent Competitive Inhibitor of RFC-Dependent Termination of Polypeptide Synthesis Two different fluorescent assays were used to quantify ataluren inhibition of termination. As described in Table 6, smTIRF assays employed three doubly-labeled forms of the Stop-POST5 complex:

Atto(pep)-Cy(tRNA)-Stop-POST5,
Atto(rbsm)-Cy(tRNA)-Stop-POST5, and
Atto(pep)-Cy(rbsm)-Stop-POST5.

Ensemble fluorescence anisotropy studies employed the singly-labeled form, Atto(pep)-Stop-POST5.

In Atto(pep)-Stop-POST5, Atto(pep)-Cy(tRNA)-Stop-POST5, and Atto(pep)-Cy(rbsm)-Stop-POST5, the lysine epsilon amino group in the pentapeptide is derivatized with atto-647.

In Atto(pep)-Cy(tRNA)-Stop-POST5 and Atto(rbsm)-Cy (tRNA)-Stop-POST5, a dihydrouridine residue of $tRNA^{Gln}$ is derivatized with Cy3.

In Atto(rbsm)-Cy(tRNA)-Stop-POST5, the ribosome is labeled with atto-647. In Atto(pep)-Cy(rbsm)-Stop-POST5, the ribosome is labeled with Cy3.

TABLE 6

Sites of fluorophore incorporation. FKVRQ is SEQ ID NO: 20 or 57. Sites of fluorophore incorporation within fluorescent Stop-POST5 complexes

| Stop-POST5 | Lys within FKVRQ | $tRNA^{Gln}$ | Ribosome |
|---|---|---|---|
| Atto(pep) | Atto647 | unlabeled | unlabeled |
| Atto(pep)-Cy-(tRNA) | Atto647 | Cy3 | unlabeled |
| Atto(rbsm)-Cy-(tRNA) | unlabeled | Cy3 | Atto647N |
| Atto(pep)-Cy(rbsm) | Atto647 | unlabeled | Cy3 |

smTIRF results using Atto(pep)-Cy-Stop-POST5 attached to surface-immobilized ribosomes. Although the distance between the two fluorophores is not close enough to produce FRET, fluorescent pairs could be identified by co-localization on the slide under alternating 532 nm and 640 nm total internal reflection fluorescence (TIRF) illumination. This permits near-simultaneous monitoring of the dynamics of peptide and P-site tRNA release from the Stop-POST5 complex following RFC binding.

To reduce photobleaching of each fluorophore, time-lapse movies were recorded with bursts of 20 or 50 frames at 100 ms frame intervals interleaved by 20 s intervals with the lasers shuttered. Total recording time for each trial was 20 min.

Figures 8A, 8C, 8E:
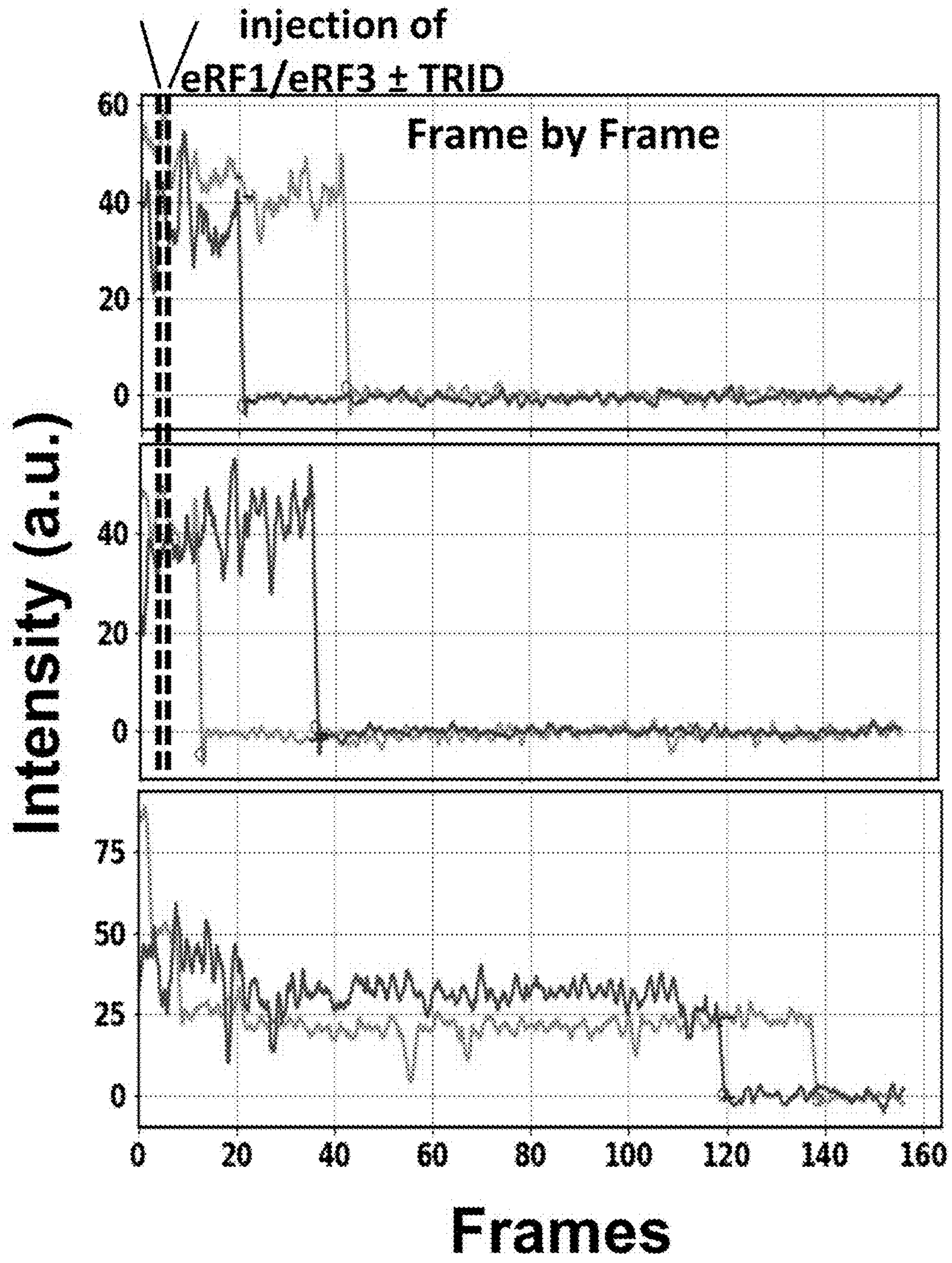
FIG. 8A, FIG. 8B, FIG. 8C, FIG. 8D, FIG. 8E, and FIG. 8F are graphs showing typical traces of the dissociation of atto-647 labeled peptide and Cy3-labeled tRNA following eRF1/eRF3±ataluren injection. In the time-lapse experiment the sample was briefly illuminated between fixed time intervals.
Figures 8B, 8D, 8F:
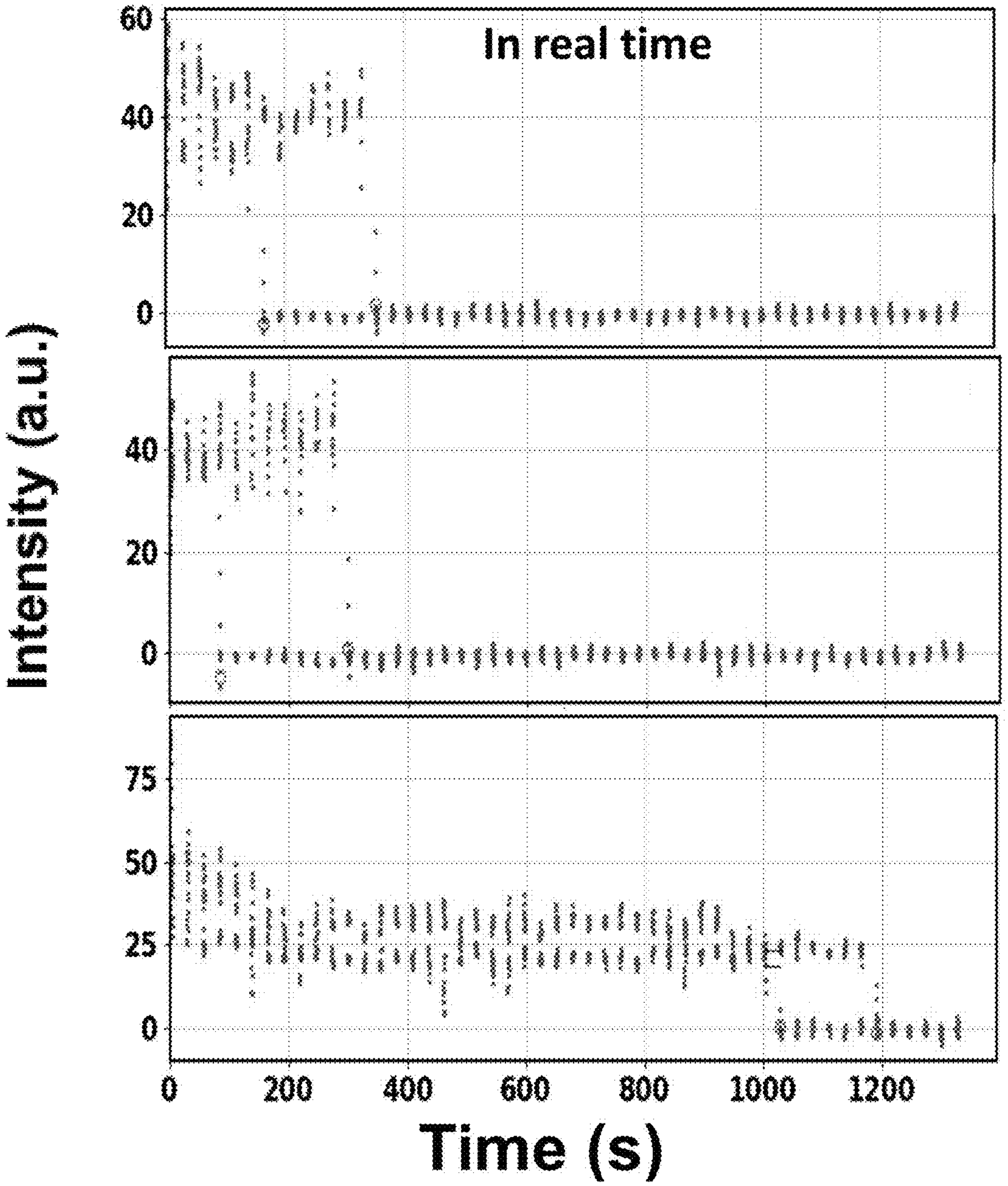

FIG. 8A and FIG. 8C show typical frame by frame recordings indicating a loss of signal for both labeled peptide and labeled tRNA after the addition of the RFC to Atto(pep)-Cy(tRNA)-Stop-POST5. The corresponding results plotted in actual time are shown in FIG. 8B and FIG. 8D. Either peptide (a) or tRNA (b) can dissociate first, in approximately equal proportions. Photobleaching of Cy3-labeled tRNA and Atto647-labeled peptide in the absence of eRF1/eRF3 was much slower (FIG. 8E and FIG. 8F). Under the time lapse illumination employed, mean lifetimes for Atto647-peptide and Cy3-tRNA at 0.32 μM eRF1 and 2 μM eRF3 were each 2.45 min. By comparison, in the absence of RFC, the mean lifetimes under time-lapse illumination before Atto647 and Cy3 disappearance were 6.8 min and 4.9 min, respectively, which were mainly due to photobleaching. Since the single-step decrease of fluorescence intensity is due either to photobleaching or to dissociation of peptide or tRNA from the ribosome, the RFC-dependent rate constant for peptide or tRNA dissociation, $k_{RF}$, was calculated as equal to $1/\langle T_{obs}\rangle - 1/\langle T_{pb}\rangle$, where $\langle T_{obs}\rangle$ is the mean observed lifetime and $\langle T_{pb}\rangle$ is the mean time until signal loss in the absence of RFs.

Figure 9A:
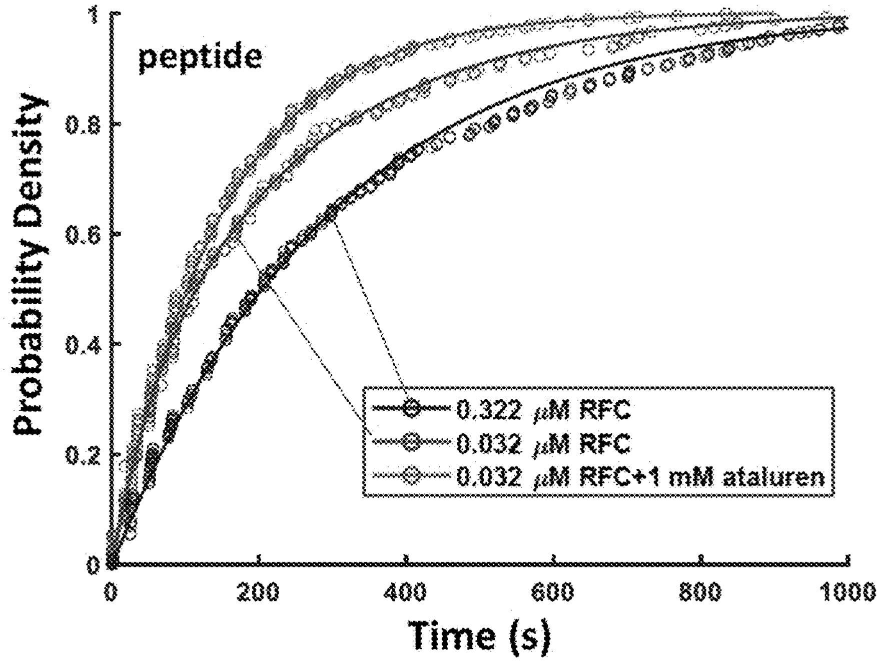
FIG. 9A and FIG. 9B illustrate cumulative distributions of peptide (FIG. 9A) and tRNA (FIG. 9B) dissociation times at two RFC concentrations, one also with 1 mM ataluren.
Figure 9B:
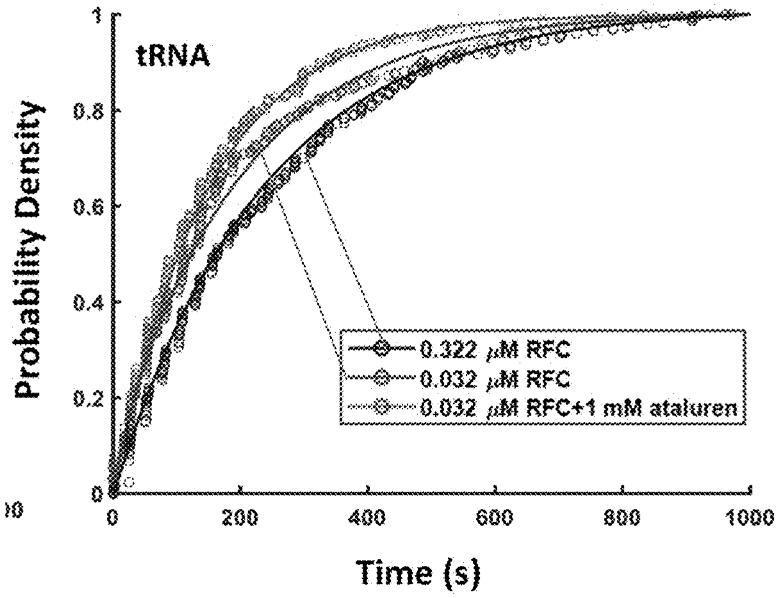
Figure 9C:
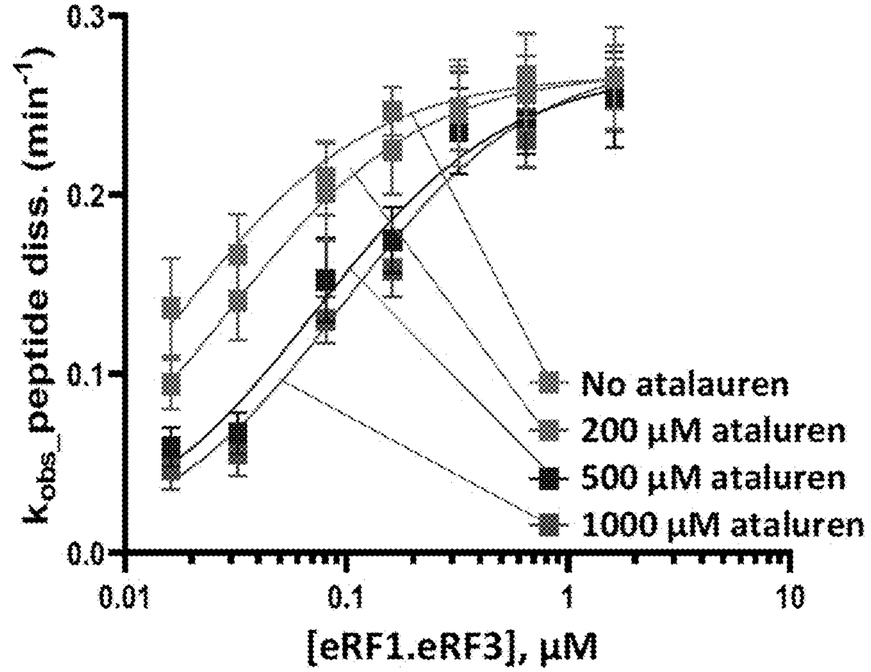
FIG. 9C and FIG. 9D illustrate rates of dissociation of peptide (FIG. 9C) and RNA (FIG. 9D) as a function of the logarithm of RFC concentration at different ataluren concentrations.
Figure 9D:
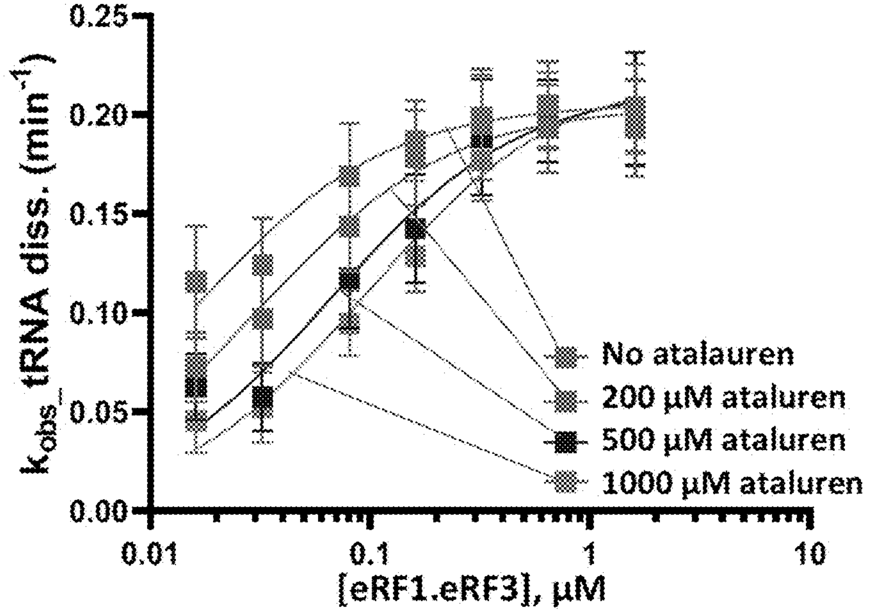

The $k_{RF}$ values for peptide and tRNA dissociation as a function of both RFC and ataluren concentrations was determined. FIG. 9A and FIG. 9B show examples of cumulative distributions of peptide and tRNA dissociation times at 320 nM, 32 nM RFC and 32 nM RFC plus 1 mM ataluren. Fitting these results to single exponentials and subtracting the photobleaching rate gave average $k_{RF}$ values. In the absence of ataluren, values of $k_{RF}$ as a function of RFC concentration fit well to the Michaelis-Menten equation, yielding values of $V_{max}$=~0.27±0.02 $min^{-1}$ peptide and 0.20±0.02 $min^{-1}$ for peptide and tRNA dissociation, respectively, and an EC50=~0.02 μM for each (FIG. 9C and FIG. 9D, red curves). Separate control experiments performed with Atto(rbsm)-Cy(tRNA)-Stop-POST5 and Atto(pep)-Cy (rbsm)-Stop-POST5 at a saturating concentration of RFC (0.65 μM eRF1, 1.3 μM eRF3) gave rate constants, 0.20±0.03 $min^{-1}$, and 0.26±0.03 $min^{-1}$, indistinguishable from those measured for Atto(pep)-Cy(tRNA)-Stop-POST5, showing that labeled peptide did not inhibit tRNA dissociation and labeled tRNA did not inhibit peptide dissociation. Addition of ataluren at concentrations of 200, 500, and 1000 μM (FIG. 9C and FIG. 9D) raised EC50 values, reaching ~0.1 μM at 1000 μM, whereas $V_{max}$ values at high RFC concentration are little affected, a strong indication that ataluren acts as an apparent competitive inhibitor of RFC.

Figure 9E:
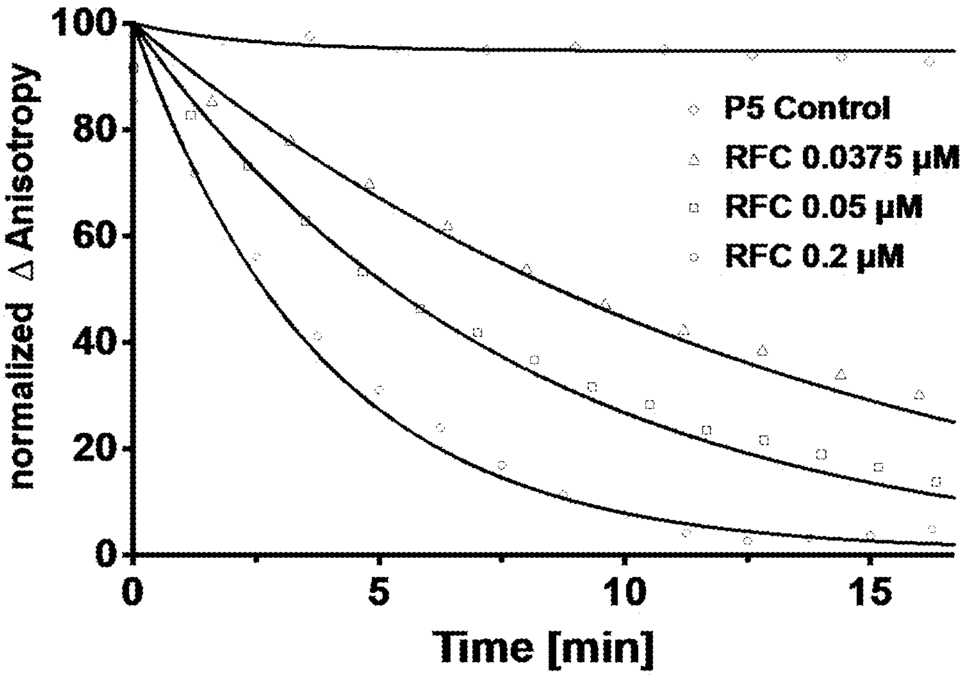
FIG. 9E and FIG. 9F illustrate the normalized plots of ensemble experiments showing single exponential fits (solid lines) of decimated smoothed raw data (points) of atto647 pentapeptide release reaction measured by fluorescence anisotropy decay as a function of time at 25° C.
Figure 9F:
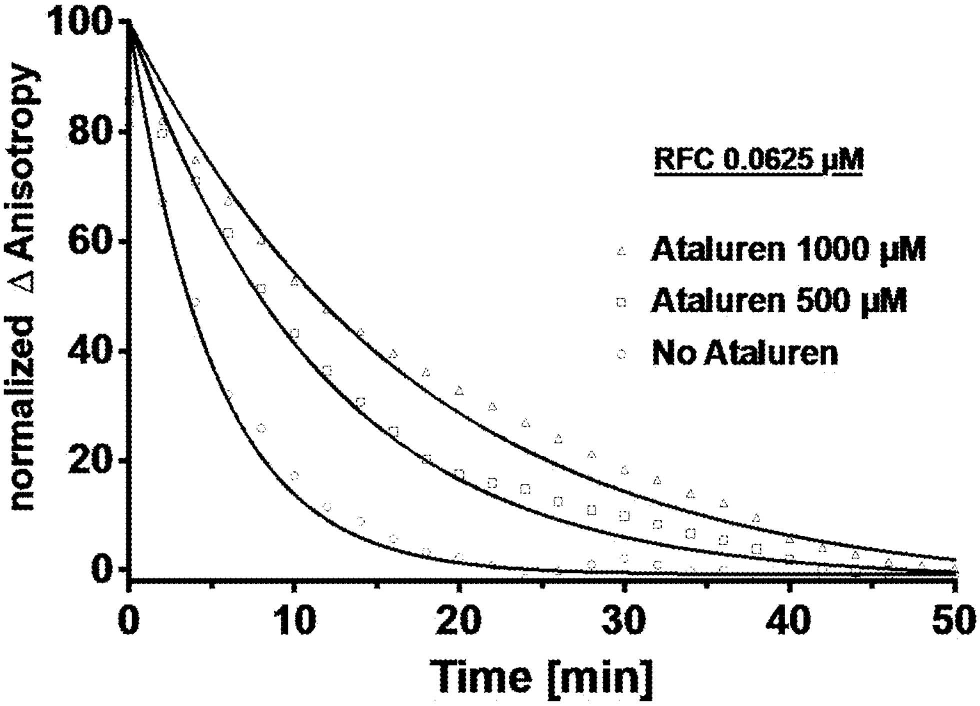
Figure 9G:
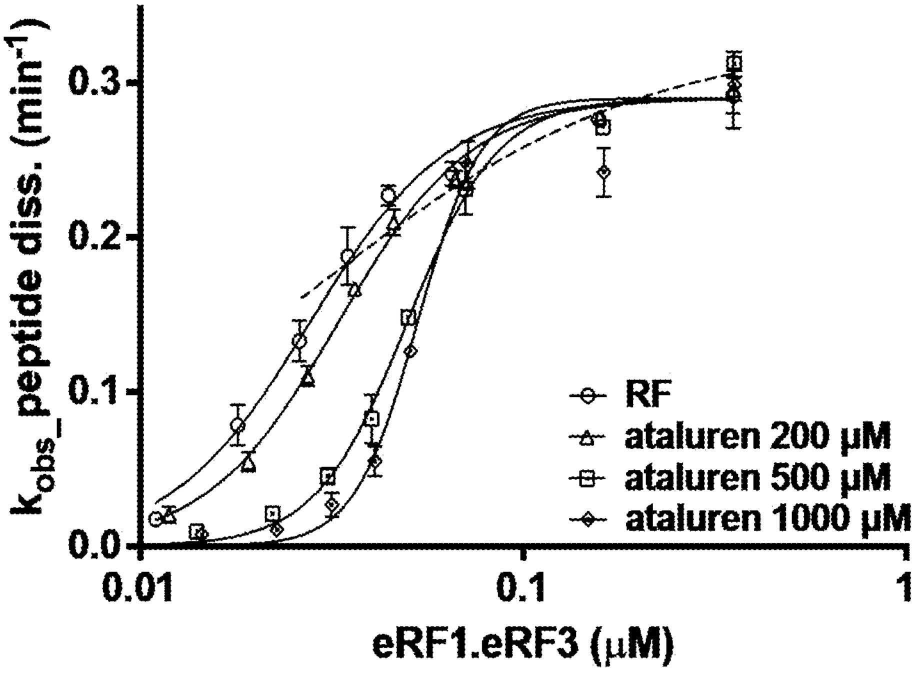
FIG. 9G illustrates the rates of dissociation of atto647 pentapeptide in ensemble experiments as a function of free RFC concentration at varying ataluren concentrations.

Ensemble fluorescence anisotropy results using Atto (pep)-Stop-POST5. The fluorescence anisotropy of the pentapeptidyl moiety of Atto(pep)-Stop-POST5 was quite high (0.22), and decreased following addition of RFC, providing a convenient measure of the rate of pentapeptide release from the ribosome. Sample results showed the time dependence of anisotropy decrease as a function of RFC concentration (FIG. 9E), and, at fixed RFC, of ataluren concentration (FIG. 4F, FIG. 9F). Each such time dependency could be fit to a single exponential, giving the collected rate constants presented in FIG. 9G, in which the rate dependence as a function of RFC concentration was measured at 0, 200, 500, and 1,000 UM ataluren. In the absence of ataluren, EC50 (0.029±0.002 UM) and $V_{max}$ (0.31±0.02) values were obtained for pentapeptide release similar to those measured by smTIRF. In addition, as with the smTIRF results, $V_{max}$ values were unaffected by added ataluren but EC50 values increased, reaching ~0.06 μM at 1000 μM.

Figure 9H:
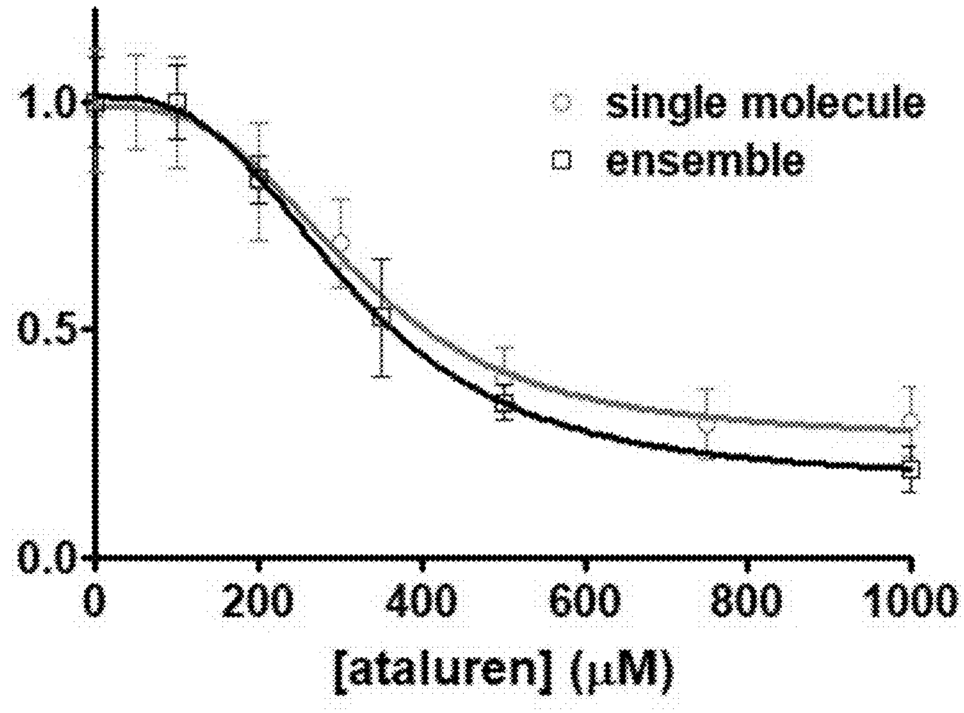
FIG. 9H illustrates ataluren inhibition of normalized rates of dissociation of atto647 pentapeptide as measured by single molecule and plate reader assays. The concentration of eRF1 was 32 nM in both assays. The concentration of eRF3 was 0.2 μM and 0.8 μM in the single molecule and ensemble assays, respectively.

Ataluren inhibition of RFC activity is cooperative. The observed dissociation rate constants for pentapeptide release, measured by both smTIRF and fluorescence anisotropy, showed very similar sigmoidal dependences on added ataluren concentration (FIG. 9H), giving a Hill n value of 3.0±0.6 and a $K_A$ of 250±20 μM. Similar results were obtained for tRNA release measured by smTIRF (Hill n=2.7±0.4, $K_A$=180±10 μM).

Additional control experiments. For both sm-TIRF and ensemble fluorescence anisotropy experiments addition of ataluren before RFC or simultaneously with RFC gave equivalent results, consistent with the notion that ataluren binds more rapidly to Stop-POST5 complex than does the RFC. In addition, very similar results were obtained in the fluorescence anisotropy experiments with POST5 complexes prepared by combination of isolated 40S and 60S subunits or from 80S ribosomes salt-treated as described in Materials and Methods.

a Kinetic Scheme for Termination

Ataluren has no direct effects on the rates of peptide and tRNA release, processes which proceed much more slowly than tRNA-peptide bond cleavage. Cleavage of the tRNA-peptide ester linkage by the RFC has been reported to proceed on yeast ribosomes with rate constants of 5-10 $min^{-1}$ at 30° C., determined using a thin layer electrophoresis assay (Shoemaker et al., *Proc Natl Acad Sci USA*. December 20; 108 (51): E1392-8 (2011); Lawson et al., bioRxiv. (2021)), much larger than the rates of complete release of the two products, ~0.3 $min^{-1}$, observed here (FIG. 9C, FIG. 9D, FIG. 9G, and FIG. 9H). These results thus support a kinetic scheme for termination in which a relatively rapid RFC-dependent cleavage of peptidyl tRNA step leading to complex C2, proceeding with a rate constant of 10 $min^{-1}$ is followed by a much slower peptide release step from complex C2 which proceeds with a rate constant of 0.3 $min^{-1}$ at saturating RFC concentration. In this scheme, ataluren binding to multiple sites within the Stop-POST5 complex competitively inhibits RFC binding. For simplicity n molecules of ataluren are shown binding in a single step.

Figure 9I:
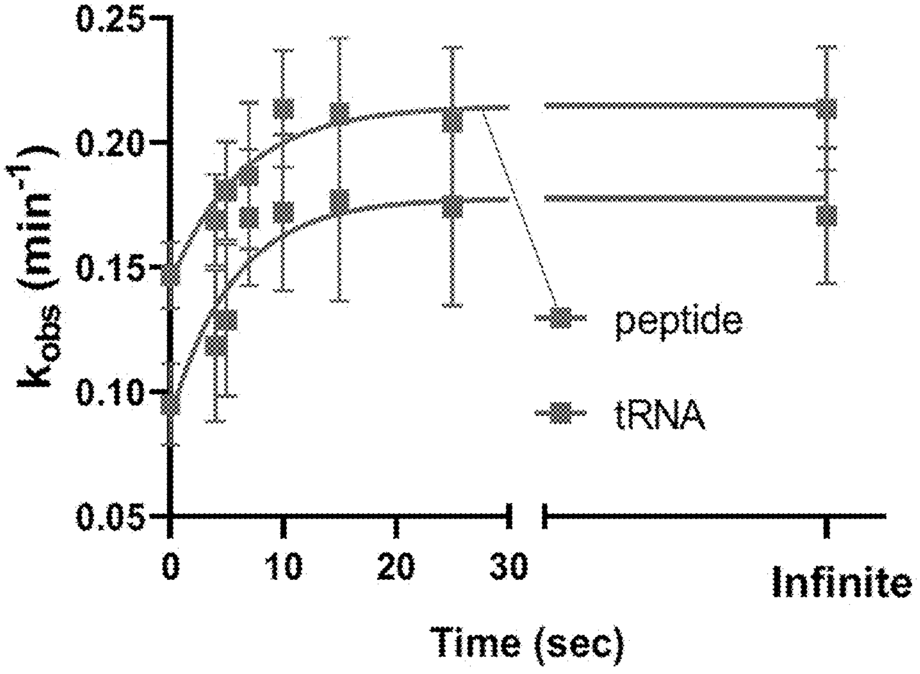
FIG. 9I illustrates ataluren inhibition of peptide and tRNA release when added at different times (4-25 s) following RFC addition to Stop-POST5. [RFC], 0.08 μM; [Ataluren], 1 mM. The values at zero-time correspond to simultaneous addition of ataluren and RFC.

If ataluren inhibits the tRNA-peptide bond cleavage solely by competition with RFC, then the time course of tRNA-peptide hydrolysis might be tracked by adding ataluren at fixed times after RFC addition. Using two syringe pumps triggered at pre-programmed times after camera recording started, Stop-POST5 was treated first with 0.081 μM RFC. Subsequently, 1000 μM ataluren was added to the flow chamber at times varying from 4-25 s. $k_{RF}$ values for peptide and tRNA dissociation are plotted vs. the interval between RFC and ataluren addition in FIG. 9I. Zero time in this plot indicates simultaneous addition of RFC and ataluren. Infinity indicates no addition of ataluren. The rate constants for elimination of ataluren's inhibitory effect after RFC addition were 10.8±3.6 $min^{-1}$ and 9.6±2.6 $min^{-1}$ for tRNA and peptide respectively, measured at 24° C. These values were much larger than the rate constants for the product release steps and were compatible with the reported rate constants for peptidyl-cleavage on yeast ribosomes mentioned above.

Figure 10A:
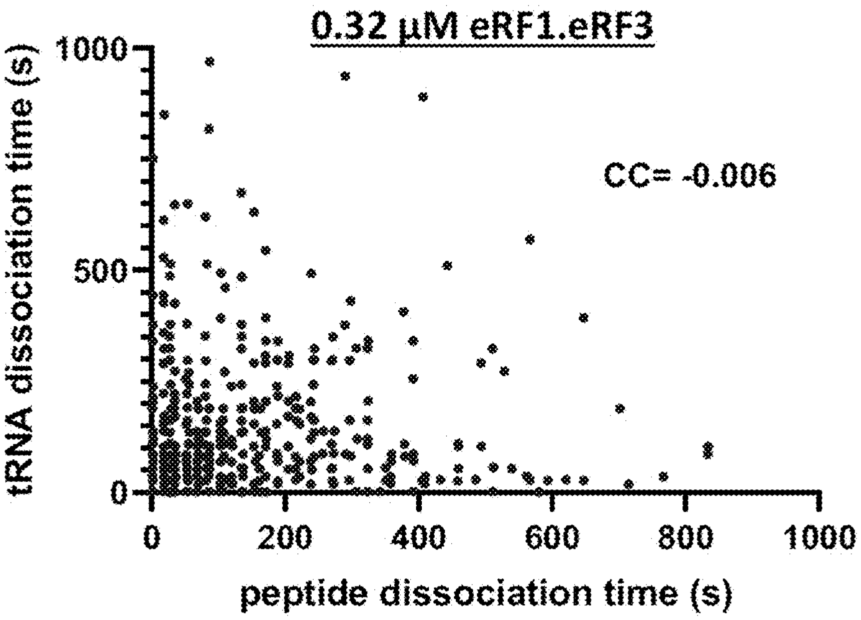
FIG. 10A, FIG. 10B, and FIG. 10C are graphs showing lack of correlation of peptide and tRNA dissociation times at 0.32 μM RFC (FIG. 10A), 0.032 μM RFC (FIG. 10B), and 0.032 μM RFC and 1 mM ataluren (FIG. 10C). CC refers to the correlation coefficient.
Figure 10B:
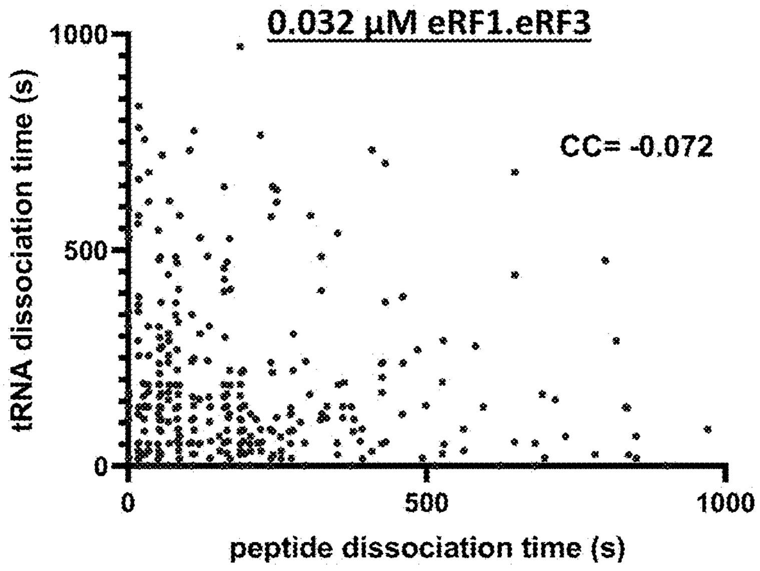
Figure 10C:
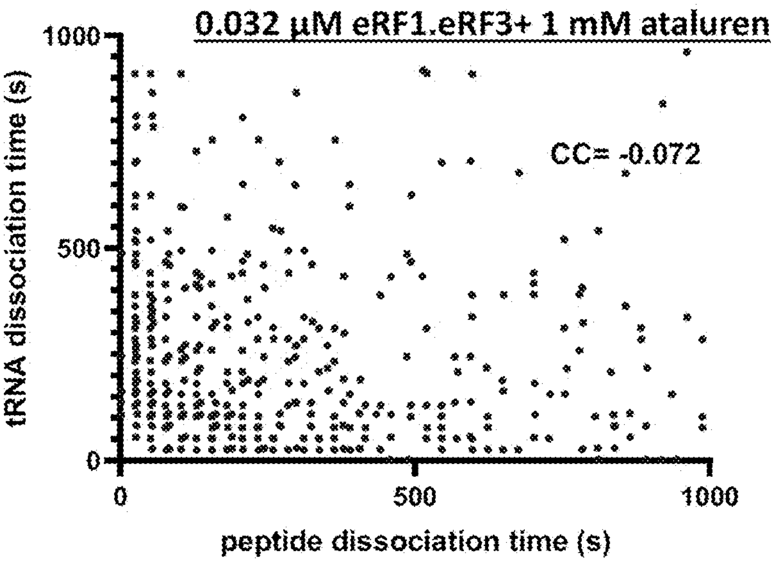

Peptide and tRNA release proceed independently of one another. Whether tRNA and peptide release were linked or independent of one another was tested by calculating the correlation coefficient between peptide and tRNA release times measured in the single molecule experiments for each ribosome. By correlating these times, it was possible to determine whether release of peptide accelerated or retarded tRNA release and, conversely, whether release of tRNA altered the rate of peptide release. FIG. 10A, FIG. 10B, and FIG. 10C show scatter plots of individual tRNA lifetimes vs. the corresponding peptide lifetimes for each particle, as well as correlation coefficients (CC) for the peptide and tRNA lifetimes, calculated using eq. (3)

$$CC = \frac{n\sum t_i p_i - \sum t_i \sum p_i}{\sqrt{n\sum t_i^2 - \left(\sum t_i\right)^2}\sqrt{n\sum p_i^2 - \left(\sum p_i\right)^2}} \quad (3)$$

where $t_i$ and $p_i$ are individual tRNA and peptide lifetimes after RFC addition, respectively, and the summations are conducted over n individual events. CC would equal 1 if the two products always dissociated together, be >1 if dissociation of one accelerated dissociation of the other, and be <0 if dissociation of one slowed dissociation of the other. CC was found to be small (−0.17<CC<+0.06) at all RFC concentrations tested (Table 7), indicating little or no effective coupling between the two dissociation processes. Added ataluren did not change the CC value (FIG. 10C), consistent with its effect being limited to inhibition of tRNA-peptide bond cleavage.

The single molecule recordings could also be segregated according to whether the peptide or the tRNA was released first, as in FIG. 8A and FIG. 8C. When this was done only a slight slowing of tRNA dissociation was generally found when it is preceded by peptide dissociation and vice versa, as summarized in Table 7.

TABLE 7

Product release rate constants and CC values.
Photoincorporation yields (%) into RNAse H Fragment IV: 26S 1413-1476

| Target | Experiment | Competing Ligand[a] | yields (%) |
|---|---|---|---|
| Stop-POST5 | PAL, | — | 0.29 ± 0.03 |
| | 300 μM AzAt | eF1/eRF3/GDPNP | 0.20 ± 0.01 |
| | PAL, | — | 0.020 ± 0.003 |
| | 30 μM AzAt | Ataluren | 0.034 ± 0.006 |
| | | GJ072 | 0.019 ± 0.004 |
| 80S.IRES | PAL, | — | 0.29 ± 0.11 |
| | 300 μM AzAt | eRF1/eRF3/GDPNP | 0.30 ± 0.03 |

[a]Added concentrations: eRF1, 2 μM; eRF3, 4 μM; Ataluren, 500 μM; GJ072, 150 μM; GDPNP, 1 mM

Example 3. Other Sites Photolabeled by AzAt

Figure 11:
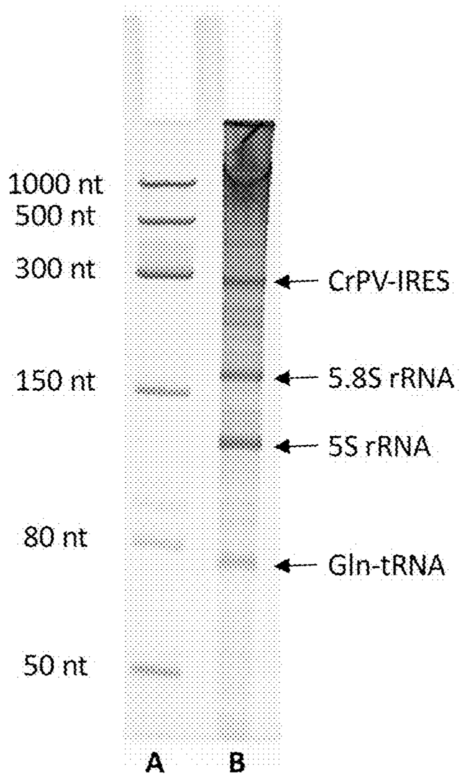
FIG. 11 illustrates 8% Urea-PAGE resolution of small RNAs. Lane A shows Ladder; Lane B shows the total RNA of Stop-POST5 extracted by phenol-chloroform, and 3 μg of the total RNA was loaded to 8% Urea-PAGE denaturing gel. The bands of each small RNA were sliced and the radioactivity was extracted for measurement with results reported in Table 2.

Small RNAs. AzAt photoincorporation into the 4 small RNAs (CrPV-IRES, 5.8S rRNA, 5S rRNA, and tRNA) contained within POST5 was examined by one-dimensional (1D) urea-PAGE analysis, by RNA-Seq, and by RNAse H fragment assay (FIG. 11). The results of 1D PAGE analysis are presented in Table 8.

TABLE 8

Photoincorporation yields (%) into RNAse H Fragment IV: 26S 1413-1476
Product release rate constants and CC Values

| [RFC], μM | peptide release rate constants ($min^{-1}$) Overall | peptide release rate constants ($min^{-1}$) As 2nd product | tRNA release rate constants ($min^{-1}$) Overall | tRNA release rate constants ($min^{-1}$) As 2nd product | CC |
|---|---|---|---|---|---|
| 1.61 | 0.26 ± 0.02 | 0.25 ± 0.03 | 0.20 ± 0.02 | 0.15 ± 0.02 | −0.018 |
| 0.65 | 0.27 ± 0.03 | 0.23 ± 0.04 | 0.21 ± 0.03 | 0.23 ± 0.04 | −0.040 |
| 0.32 | 0.26 ± 0.02 | 0.24 ± 0.03 | 0.20 ± 0.02 | 0.17 ± 0.03 | −0.006 |
| 0.166 | 0.24 ± 0.01 | 0.19 ± 0.02 | 0.18 ± 0.02 | 0.14 ± 0.03 | 0.064 |
| 0.080 | 0.21 ± 0.02 | 0.15 ± 0.02 | 0.17 ± 0.03 | 0.12 ± 0.02 | −0.166 |
| 0.032 | 0.16 ± 0.02 | 0.15 ± 0.02 | 0.12 ± 0.02 | 0.063 ± 0.021 | −0.072 |
| 0.016 | 0.13 ± 0.02 | 0.12 ± 0.03 | 0.10 ± 0.02 | 0.086 ± 0.023 | −0.065 |

The highest labeling at either 30 μM or 300 μM AzAt was found in CrPV-IRES. Labeling CrPV-IRES at 300 μM AzAt showed partial but significant reduction on addition of eRF1.eRF3.GDPNP. In contrast, addition of eRF1.eRF3.GDPNP did not significantly reduce labeling of the other small RNAs. Added ataluren or GJ072 resulted in generally small reductions in the labeling of small RNAs, none of which are clearly significant. However, within the small RNAs, Laser-Seq analysis did identify three nucleotides in the CrPV-IRES with ≥1.4-fold mutation rate changes: IRES-A142 (1.4-fold), IRES-U177 (2.4-fold) and IRES-G186 (2.0-fold), corresponding to nucleotides A6151, U6186, and G6195 in CrPV RNA numbering, respectively.

Figure 12:
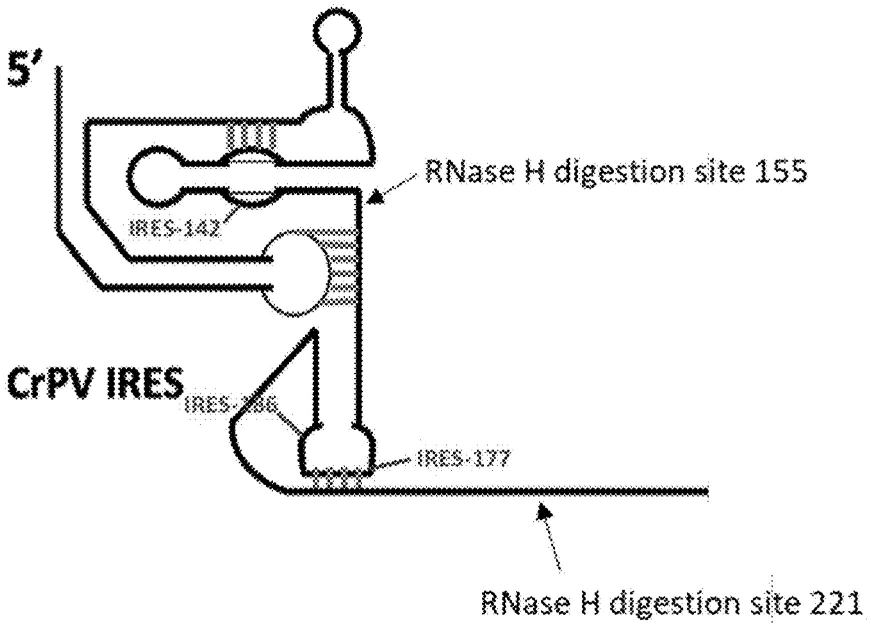
FIG. 12 is a diagram showing the photolabeled sites and RNase H digestion sites in CrPv-IRES-mRNA.
Figure 13:
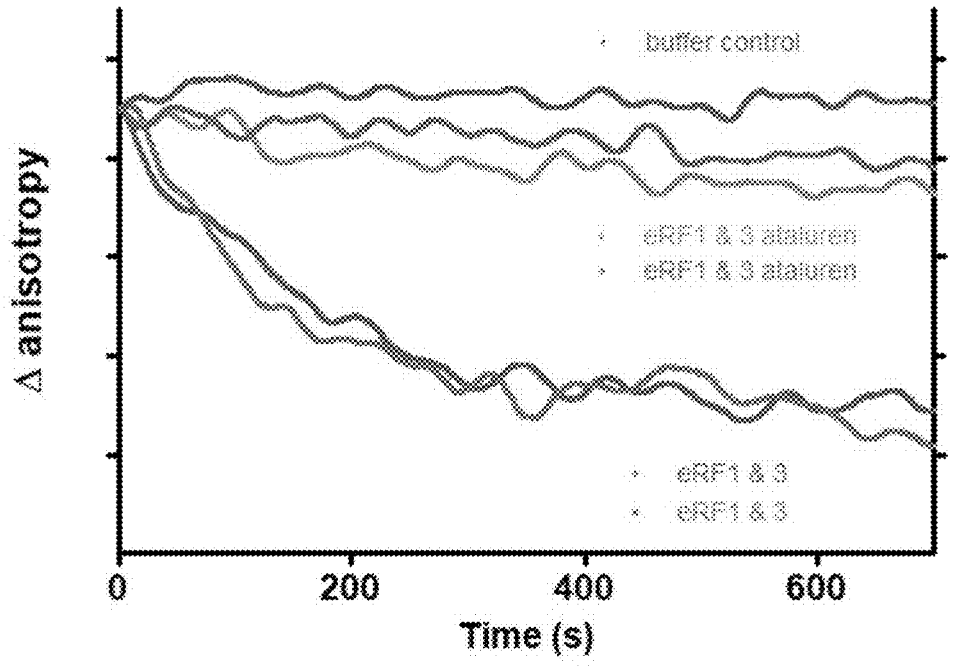
FIG. 13 is a graph showing change in fluorescence anisotropy upon peptide release in real time, and inhibition of peptide release by ataluren.

As indicated in FIG. 12, IRES-A142 is located in the bulge region of stem loop V, and IRES-U177 and IRES-G186 are clustered at the stem loop region of the CrPV-IRES pseudo-knot PKI, which mimics the anti-codon stem loop of the initiator tRNA during translation initiation.

The RNAse H fragment assay was employed to test the response of the labeling of CrPV-IRES fragments 1-155, containing A-142, and 156-221, containing U177 and G186, to the addition of either eRF1.eRF3.GDPNP, ataluren, or GJ072, which gave results summarized in Table 8. Only minor decreases were observed on addition eRF1.eRF3.GDPNP, and no clearly significant changes were observed on addition of either ataluren or GJ072.

26S A1437/A1438. 26S-A1437 and 26S-A1438 are located at the apical loop of the H44 of 28S rRNA, near the GTPase association center, have 1.4-fold and 1.3-fold mutation rate changes by Laser-Seq analysis, and are each within 10 Å of ribosome-bound eRF1. RNAse H was used to generate the 26S fragment 1413-1476 (Fragment IV) which contains both A1437 and A1438 and determined the effects of either eRF1.eRF3.GDPNP, ataluren, or GJ072 on AzAt photoincorporation. The results, presented in Table 8, showed that AzAt photolabels Fragment IV equally well in both POST5 and 80S.IRES, but in neither case does addition of eRF1.eRF3.GDPNP result in major reduction, and neither ataluren nor GJ072 reduce labeling at all.

It was concluded that neither CrPV-IRES nor 26S A1437/1438 photolabeling by AzAt were likely to occur from a functionally important ataluren binding site.

Example 4—Diversity in Peptidyl-tRNA Reporters for Aniosotropy Assays

Cricket Paralysis Virus IRES-linked mRNAs were used to by-pass cap-dependent translation initiation, dispensing with the need for initiation factors (Ng et al., *ACS Med Chem Lett,* 9, 1285-1291 (2018); and Zhang et al., *Elife.* 5: e13429 (2016)). To measure the fluorescence anisotropy change, Lysine or Cysteine, or non-canonical amino acids in the Stop-POST complex can be labeled with fluorophores.

Fluorometer measurements of POST5 complex Stop IRES-Lys* included the following treatment methods and components:

POST5 complex was treated with ternary complexes of release factor 1 and 3 and GTP. Lys was labeled with the fluorescent label Atto647. Conditions for the assay were as follows: at 25° C., Buffer condition included 0.1 μM POST 5. Release factor 1 and 3 (eRF1 & 3) POST 5 condition included 0.1 μM POST5; eRF1 at 0.1 μM; eRF3 at 0.2 μM; and GTP at 2 mM. Release factor 1 and 3 (eRF1 & 3) POST 5 and ataluren condition included 0.1 μM POST5; eRF1 at 0.1 μM; eRF3 at 0.2 μM; GTP at 2.0 mM; and Ataluren at 500 mM.

Peptide release resulted in a significant anisotropy change and ataluren inhibited peptide release. Fluorescence anisotropy change was observed upon peptide release in real time and release was inhibited by ataluren. This peptide labeled Stop-IRES allows fast drug screens of any premature termination codon disease related sequences.

Identification of Ataluren Binding Sites

It was demonstrated that ataluren stimulation of nonsense codon readthrough resulted exclusively from its inhibition of RFC-dependent termination of polypeptide synthesis and did so via apparent binding to multiple, probably at least three, sites of the protein synthesis apparatus (Ng et al., *Proc Natl Acad Sci USA,* 118: e2020599118 (2021), incorporated by reference herein in its entirety). Here, using both single molecule and ensemble measurements of release factor activity, it is demonstrated that ataluren binding to these sites competitively inhibits RFC catalysis of termination and use of a photoaffinity labeling approach (PAL) identified two of these ataluren sites within rRNA.

Figure 1B:
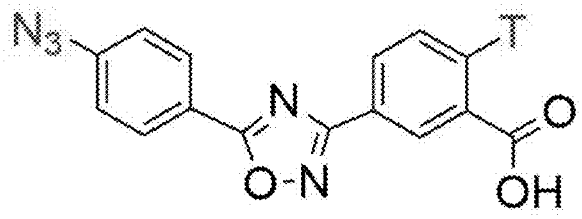
Figure 1C:
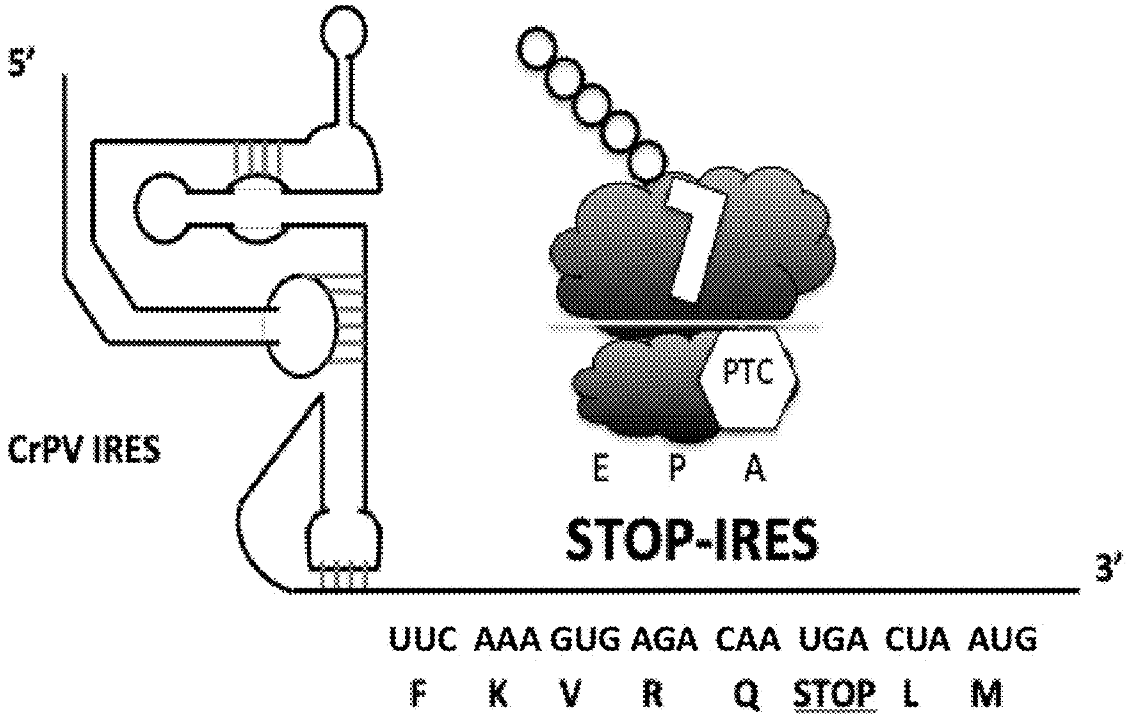
Figure 1D:
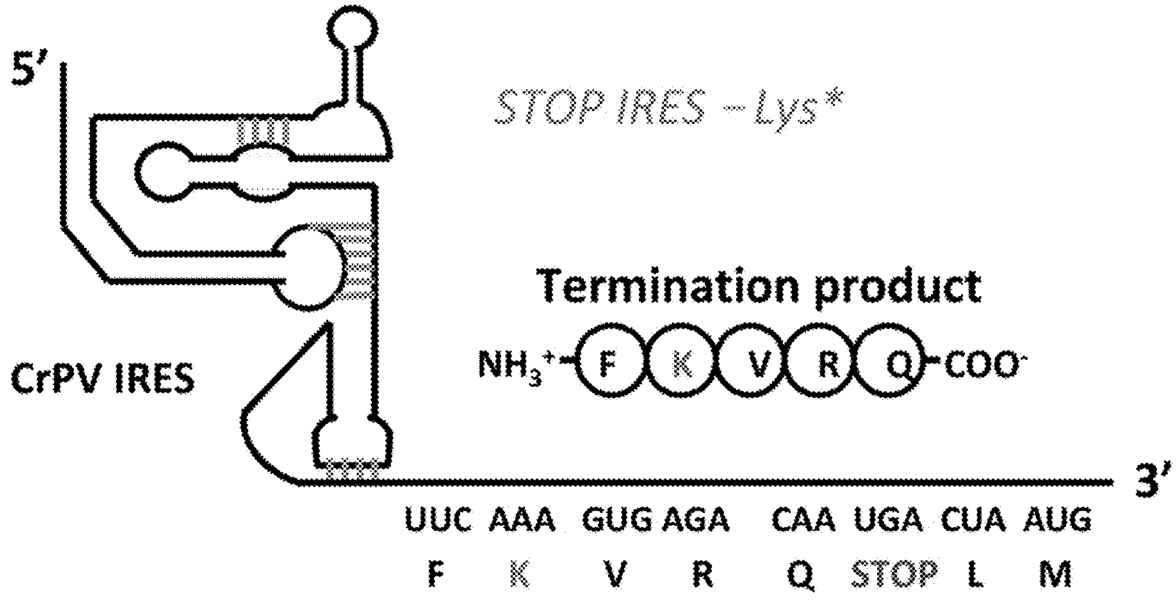
Figure 1E:
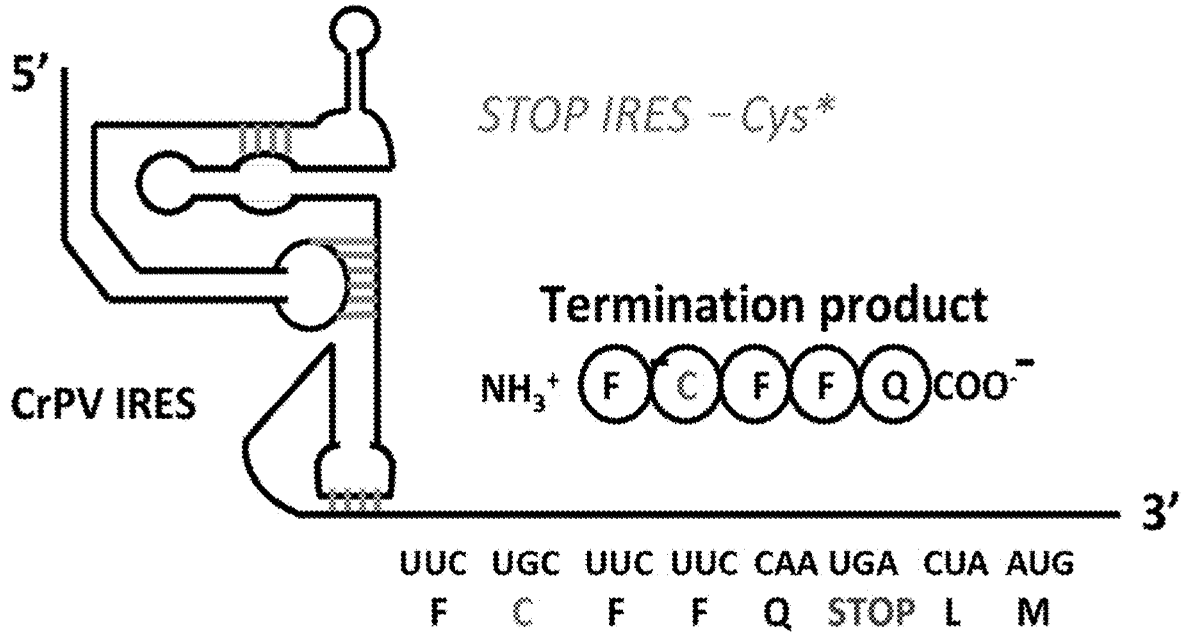
Figure 1F:
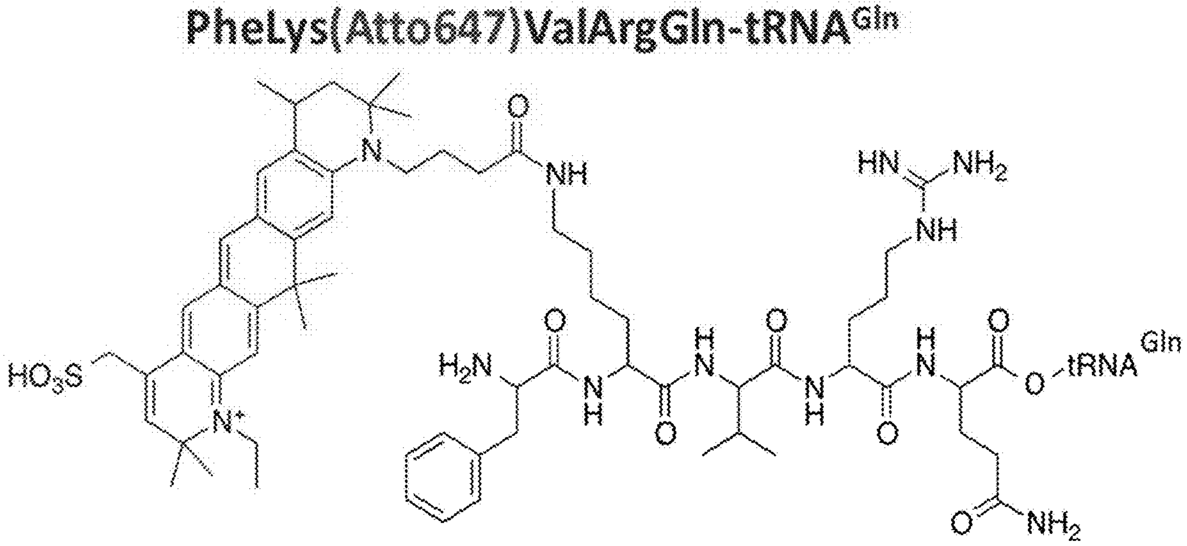
Figure 3A:
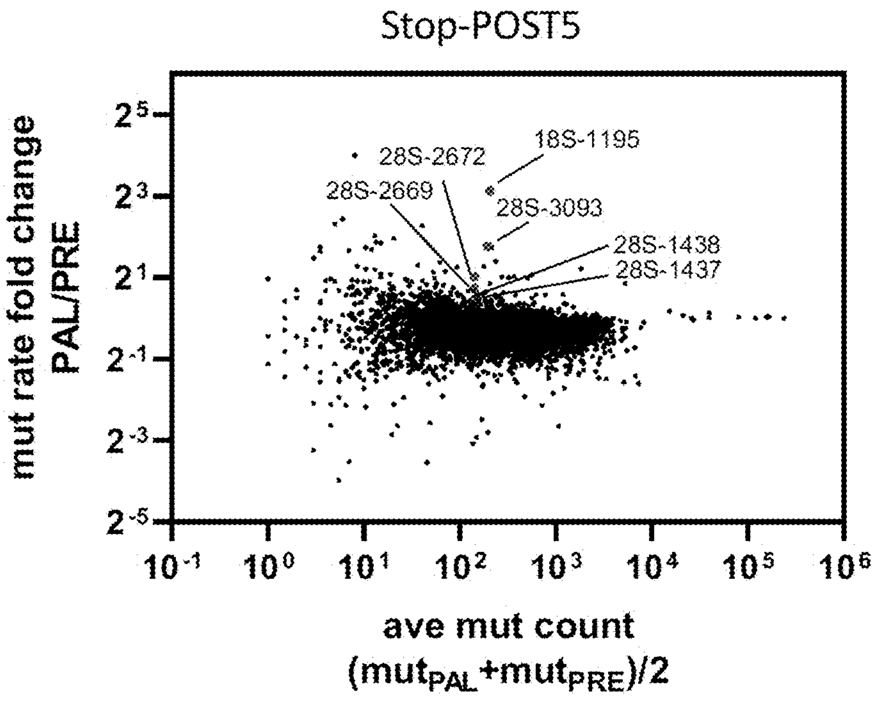
FIG. 3A, FIG. 3B, FIG. 3C, FIG. 3D, and FIG. 3E are graphs illustrating LASER-seq assay to identify putative AzAt photo-incorporation sites.
Figure 3B:
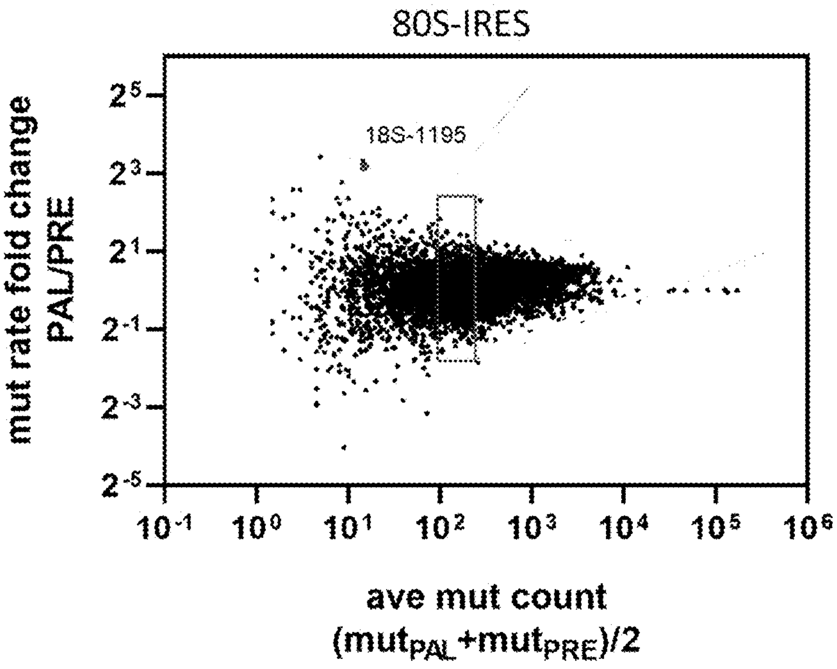
Figure 3C:
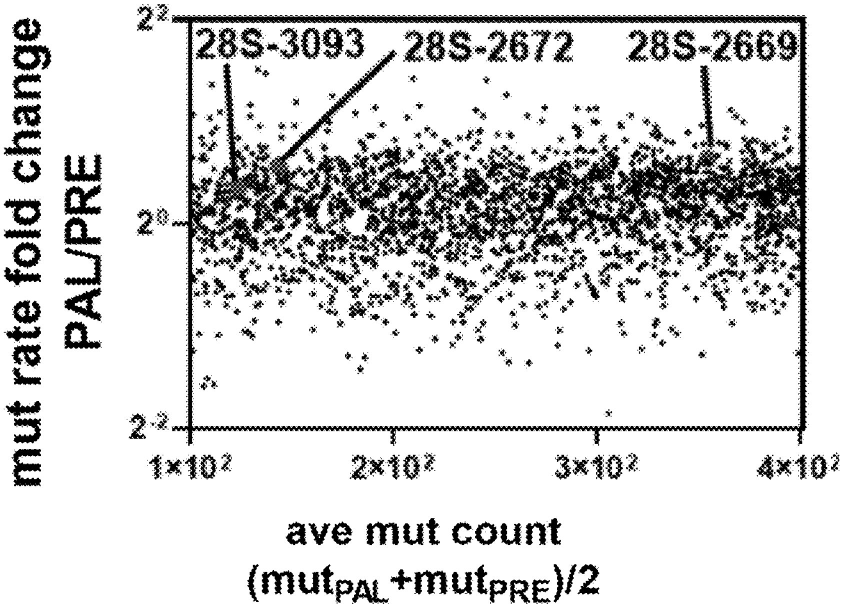
Figure 3D:
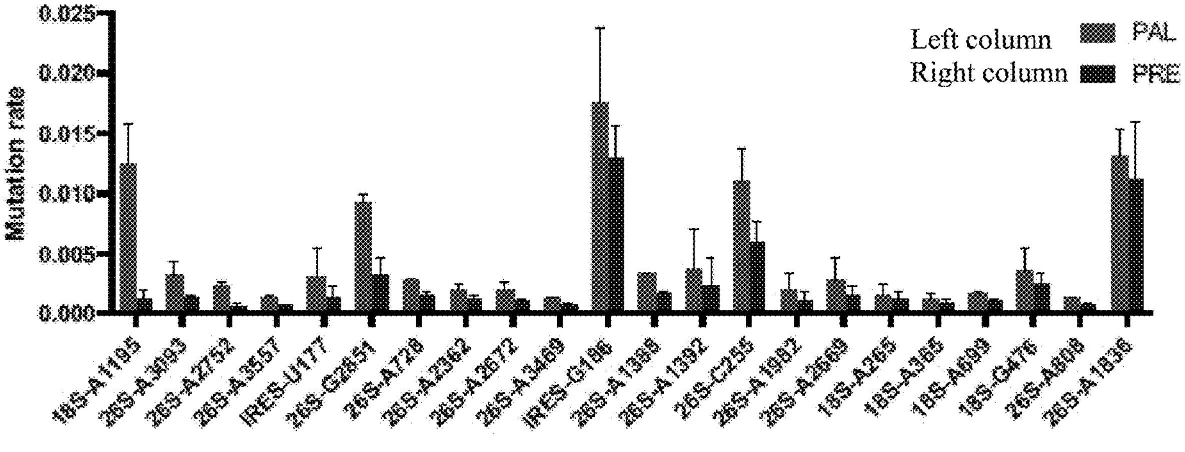
Figure 3E:
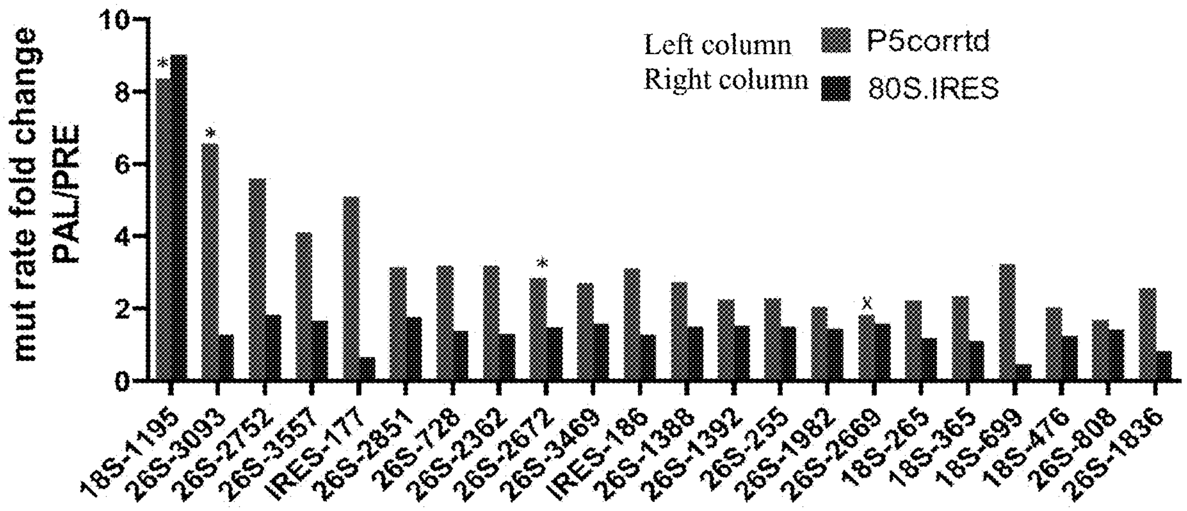

One of these sites, identified by AzAt photoincorporation into 18S-A1195, is proximal to the ribosome decoding center (FIG. 6A) while the second lies within the PTC (FIG. 6C). AzAt is a close structural and functional analogue of ataluren (FIGS. 1A and 1B). Thus, as expected, ataluren strongly inhibits AzAt photoincorporation into 18S-A1195 of Stop-POST5 (Table 5), which proceeds via a simple binding isotherm (FIG. 3E). In contrast, AzAt photoincorporation into the three nucleotides located within the PTC, 26S-A2669, 26S-A2672, and 26S-A3093, shows a sigmoidal dependence. Such dependence is indicative of an AzAt-dependent conformational change resulting from AzAt binding elsewhere in the POST5 complex, which is required for efficient photoincorporation into the PTC (FIG. 3E). Importantly, AzAt photoincorporation into each of these sites is strongly inhibited by added eRF1.eRF3.GDPNP (Table 5), a result providing a structural rationale for the observed competitive inhibition by ataluren of RFC termination activity.

The apparent Hill n of ~3 for AzAt photolabeling of the PTC in Stop-POST5 (FIG. 3E) is similar to the Hill n values found for ataluren inhibition of termination (FIG. 9H) and for ataluren stimulation of readthrough (Ng et al., *ACS Med Chem Lett,* 9, 1285-1291 (2018)). This similarity shows that ataluren binding to both the 18S-A1195 site and the PTC is directly responsible for the competitive inhibition by ataluren of RFC termination activity. It also suggests that at least one additional ataluren binding site in Stop-POST5 is involved in the putative conformational change required for full competitive inhibition of termination activity and full AzAt photoincorporation into the PTC. A low yield of AzAt photoincorporation into such a site would have prevented its identification in the PAL experiments. In addition to the 18S-A1195 site and the PTC, AzAt photo incorporates into an ataluren binding site within eRF1 (FIG. 2D and FIG. 2E). Such binding, which clearly does not affect $V_{max}$ values for peptide and tRNA departure from the ribosome (FIG. 9C, FIG. 9D, and FIG. 9G), could weaken RFC binding to the ribosome.

a Kinetic Scheme for Termination

Figure 14A:
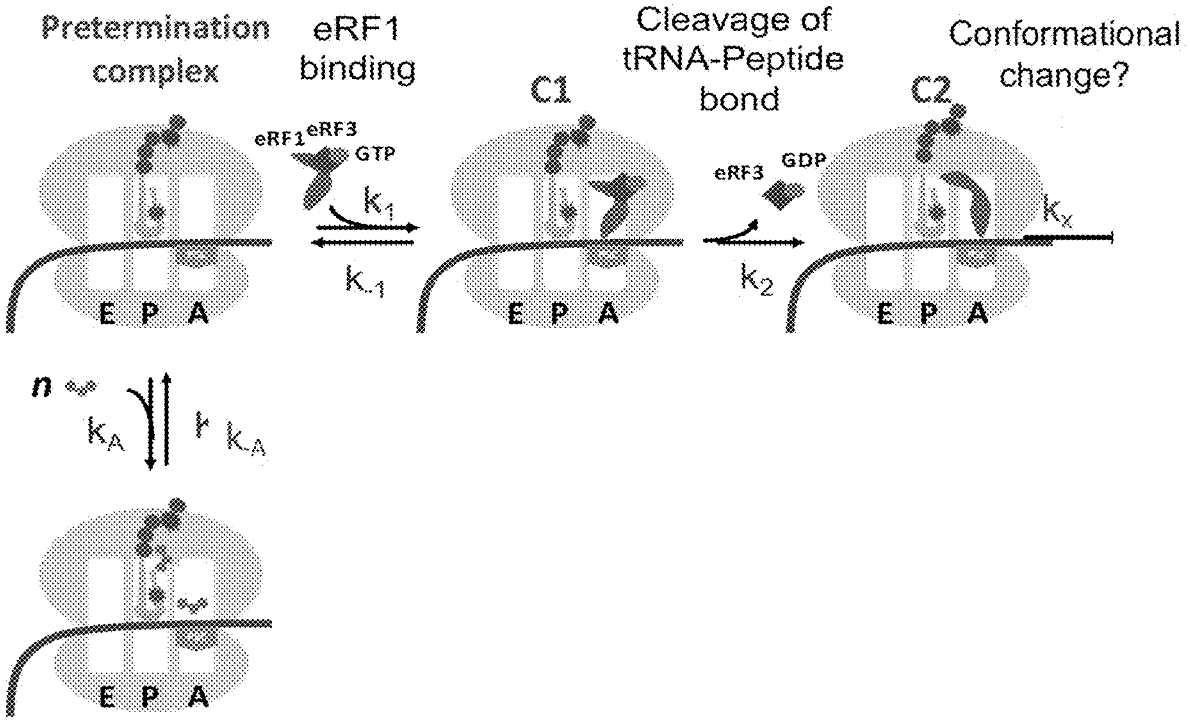
FIG. 14A and FIG. 14B are diagrams showing a simplified model for RFC catalysis of termination. This model shows that ataluren inhibition results from competition with RFC binding to the pretermination complex, and posits a complex C3 to account for the similarity in the rate constants of tRNA and peptide release. A more minimal model eliminates C3 and posits that the product release and reversible eRF1 release steps proceed directly from C2 as described herein.
Figure 14B:
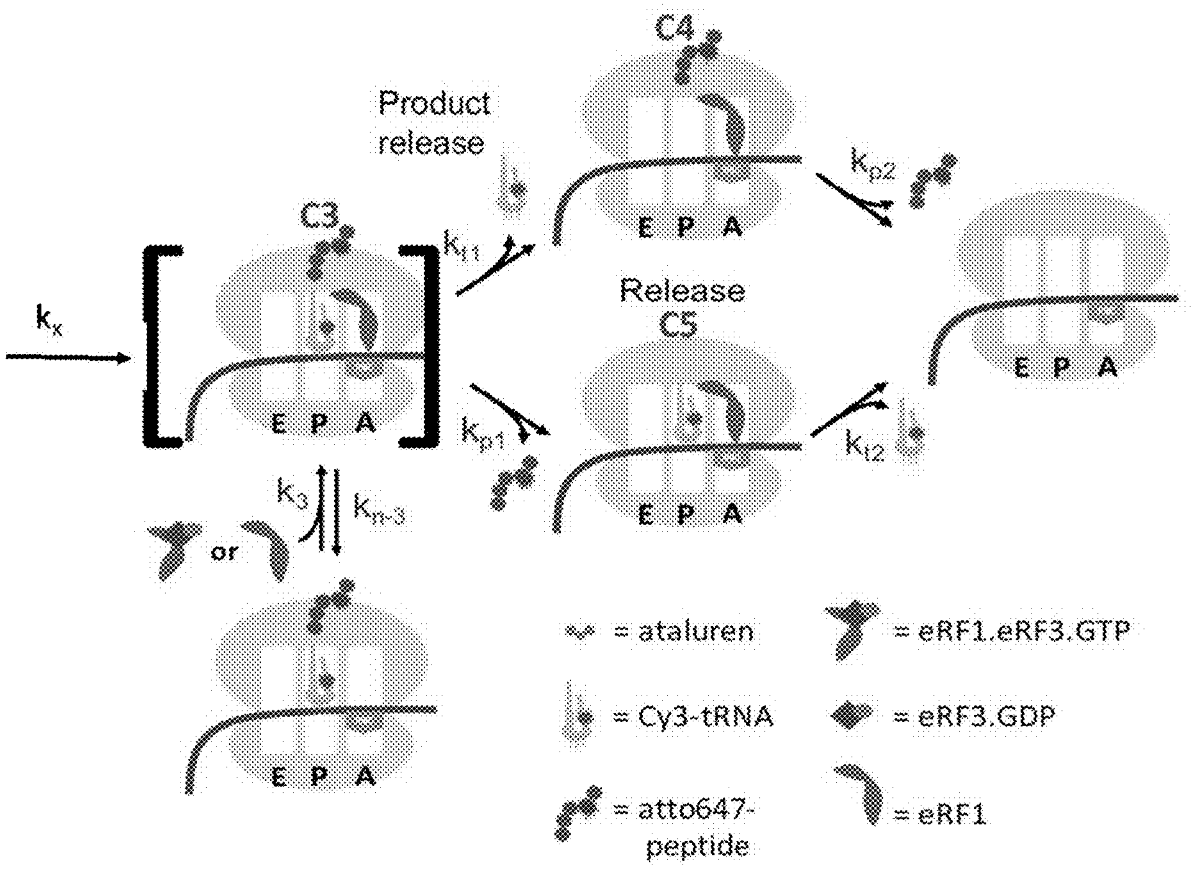

It is useful to present a highly simplified and only semi-quantitative kinetic scheme (FIGS. 14A and 14B) for termination of peptide synthesis and its inhibition by ataluren, consistent with the results presented above. In this scheme the relatively rapid cleavage step leading to complex C2 proceeds with a rate constant of 10 $min^{-1}$. The much slower tRNA and peptide release steps from complex C3 proceed with similar apparent constants of 0.2 to 0.3 $min^{-1}$ at saturating RFC concentration (Table 7). This similarity shows that they are each limited by a common, at least partially rate-determining step, by which C2 is converted to C3, which may correspond to a conformational change. It has a rate constant of $k_x$, and C3 is in heavy brackets. Recent results of others under conditions comparable to those tested here indicate that eRF1 dissociates in 20±10 s from a yeast ribosome following the cleavage reaction (Lawson et al., bioRxiv. (2021)). In the scheme such dissociation is characterized by the rate constant $k_3$. However, the dependence of the apparent release rate constants on RFC concentration long after the cleavage reaction has taken place (FIGS. 9A-9I and Table 7) show that eRF1 presence on the ribosome is required for release of tRNA and peptide, i.e., that eRF1 dissociation must be reversible. Accordingly, the rebinding of eRF1 is assigned, either alone or as part of the RFC, a rate constant of k-3. Similar reversible binding of eRF1 or RFC might also take place to complexes C4 and C5.

The results in FIGS. 9A-9I show that ataluren is an apparent competitive inhibitor of RFC catalysis of tRNA and peptide release but only acts on steps up to the cleavage reaction. This accounts for the placement of ataluren binding prior to formation of complex C1. For simplicity n molecules of ataluren are shown binding in a single step, and, in the diagram, indicate two of the binding sites identified by the photoaffinity labeling results as being in the 40S decoding center and the 60S PTC. The lack of ataluren effect on any step following cleavage clearly indicates that rebinding (rate constant $k_3$) differs from initial binding (rate constant $k_1$). Possible candidates would include conformational changes within the ribosome complex following hydrolysis of the peptidyl-tRNA bond and/or differences in eRF1 vs. RFC binding.

High Throughput Screening for TRIDs

The results show that the anisotropy assays are useful at screening molecules to identify TRIDs with greater potency than ataluren for combatting PSC diseases. The results here demonstrate that ataluren binding to both the decoding center and the PTC (FIGS. 2G, 2H FIG. 6A and FIG. 6C) competitively inhibits RFC-dependent termination at a stop codon. In contrast to its inhibition of RFC binding, ataluren has no effect on the productive binding of a near-cognate aa-tRNA.eEF1A.GTP complex (TC) at a stop codon (Ng et al., 2021), even though near-cognate ternary complex (TC) and RFC binding sites to pretermination complexes like Stop-POST5 have considerable overlap (Shao et al., Cell. November 17; 167 (5): 1229-1240.e15 (2016)). This difference provides that efforts to design more potent analogues of ataluren should focus on areas of the RFC binding site on the ribosome which do not overlap with the TC binding site.

Example 5. Diversity in Peptide Sequence within a StopPost Complex

The dye-labeled PURE-Lite IRES can be used with diverse peptide sequences to tune the assay in specific ways:

1. Simplifying messages to one or two amino acids and using shortened peptide sequence variants allow for more cost effective TRID screens, for example IRES-FK*FFF-Stop (SEQ ID NO: 27), IRES-FC*F-Stop. Star (*) indicates a labeled amino acid residue.

2. PTC peptide release efficiency depends on the individual sequence context before and after the stop codon and affects the potency of TRIDs (Cridge et al. *Nucleic Acids Research*, February 28; 46 (4): 1927-1944 (2018), Bonetti et al. *JMB* August 18; 251 (3): 334-345 (1995)). Any disease specific PTC (UGA, UAA & UAG) sequence of mRNA can be placed within a CrPV-IRES Post complex for TRID screening, and for precise mechanistic and structure activity relationship studies of TRID. One example is the commonly occurring cystic fibrosis PTC mutation CFTR (G542X) DNTVL-Stop-EG (SEQ ID NO: 28, Pranke et al *ERJ Open Res* 4:00080-2017 (2018)). CrPV-IRES Post complex for screening to find TRIDs effective in cystic fibrosis can include an mRNA sequence encoding DNTVL-Stop-EG.

Example 6. Exemplary Application of the High-Throughput Screening for TRIDs in Personalized Medicine Readthrough arises principally from functional near-cognate tRNA binding, in competition with eRF1-FX catalyzed termination and nonsense-mediated mRNA decay (NMD). The results of the cell-based assays support the major conclusions that readthrough is most favored by the UGA codon and that the context downstream from the stop codon is more important than the upstream context. For all three stop codons, readthrough is strongly influenced by the downstream nucleotide immediately following the termination codon (position+4, when the first nucleotide of the stop codon is designated as position+1) with most studies showing that C at +4 (C+4) gives maximum readthrough. The preference for C is clearest for UGA, although in some studies the preference for C is more marked (Cridge et al., *Nucleic Acids Res.* 2018 Feb. 28; 46 (4): 1927-1944; Manuvakhova et al., *RNA.* 2000 July; 6 (7): 1044-55; Martorell et al., *Haematologica.* 2020 Jan. 31; 105 (2): 508-518) than others (McCaughan et al., *Proc Natl Acad Sci USA.* 1995 Jun. 6; 92 (12): 5431-5; Floquet et al., *PLOS Genet.* 2012; 8 (3): e1002608; Beznosková et al., *Nucleic Acids Res.* 2015 May 26; 43 (10): 5099-111). A recent study (Anzalone et al., *Biochemistry.* 2019 Feb. 26; 58 (8): 1167-1178) also indicates a strong preference for C+4 downstream from a UAG codon. Further downstream, C+8 (Cridge et al., *Nucleic Acids Res.* 2018 Feb. 28; 46 (4): 1927-1944) or C/U+8 (Martorell et al., *Haematologica.* 2020 Jan. 31; 105 (2): 508-518) also strongly favor UGA readthrough. A major stimulant of readthrough is the presence of a downstream secondary structure (stem loop or pseudoknot) immediately adjacent to or separated by variable lengths of nucleotides from the stop codon (Firth et al., *Nucleic Acids Res.* 2011 August; 39 (15): 6679-91; Eswarappa et al., *Cell.* 2014 Jun. 19; 157 (7): 1605-18; Napthine et al., RNA. 2012 February; 18 (2): 241-52; Kuhlmann et al., *J Virol.* 2016 Sep. 12; 90 (19): 8575-91).

The PURE-LITE system can be used to predict the ability of termination-specific TRIDs to stimulate readthrough at stop codons in specific sequence contexts. Such predictive ability could aid in determining which PSC sequence contexts found in CF patients have the highest probability for being successfully treated by termination-specific TRIDs. Termination-specific TRIDs would be predicted to be most effective in inhibiting termination and stimulating readthrough at mRNA sequences having weak affinity for eRF1/eRF3. Experiments will be carried out to test how the PURE-LITE assays respond to the complete downstream sequences promoting readthrough of the UAG codon that have been identified by Anzalone et al., This work has identified the +4-+8 sequences CGCCA, CUAUC, CAGAC as being especially favorable for readthrough.

PURE-LITE assay applied for treatment of CF patients. Studies on sequence contexts found in CFTR2 variants will be carried out. The latest (Jul. 31, 2020) tabulation by the Cystic Fibrosis Foundation of CFTR2 variants lists 360 that cause CF. Among these, 77 are PSCs, with the three termination codons present in roughly similar amounts (UAG 18; UAA 30; UGA 26-three variants have a UAG/UGA ambiguity). Collectively these variants display a great variety of sequence contexts, some examples of which are shown in Table 9, with nucleotides favoring readthrough are underlined.

TABLE 9 variety of sequence contexts for mRNA sequences with premature stop codons (PSC).

Downstream Sequences of CFTR PSC mutations [a]

| CFTR Mutant | mRNA Sequences Peptide Sequence | SEQ ID NO |
|---|---|---|
| Q30X | UAG <u>CGC</u> <u>C</u>UG GAA UUG | 29 |
| | <u>Arg</u> <u>L</u>eu Glu Leu | 30 |
| E60X | UAG <u>C</u>UG G<u>C</u>U UCA AAG | 31 |
| | <u>L</u>eu A<u>l</u>a Ser Lys | 32 |
| G542X* | UGA GAA GGU GGA AUC | 33 |
| | Asp Gly Gly Ile | 34 |
| R553X* | UGA GCA AGA AUU UCU | 35 |
| | Ala Arg Ile Ser | 36 |
| Y1092X | UAR <u>C</u>UG U<u>C</u>A ACA CUG | 37 |
| | <u>L</u>eu S<u>e</u>r Thr Leu | 38 |
| R1162X* | UGA GUC U<u>U</u>U AAG UUC | 39 |
| | Val P<u>h</u>e Lys Phe | 40 |
| S1196X | UGA <u>C</u>AC G<u>U</u>G AAG AAA | 41 |
| | <u>H</u>is V<u>a</u>l Lys Lys | 42 |
| W1282X* | UGA AGG AAA GCC UUU | 43 |
| | Arg Lys Ala Phe | 44 |

[a] Starred mutants occur most frequently in CFTR patients.
Stop codons are indicated for the mRNA without a corresponding amino acid
There is ambiguity over whether the 3'-terminal base in the Y1092X mutant is an A or G.
Nucleotides favoring readthrough are underlined.

These sequences and those of other CFTR PSC mutants will be examined for the predicted presence or absence of downstream secondary structure using RNA-Fold (68). This analysis will result in a list of the 77 PSC variants approximately grouped by their predicted eRF1-FX binding affinities and their putative susceptibilities to increased readthrough by termination-specific TRIDs. The PURE-LITE assays can then be used experimentally to determine the effects of such TRIDs on termination and readthrough for sequence contexts having the highest, intermediate, and lowest predicted susceptibilities, to determine the validity of the predictions. If valid, they could lead to a targeted use of termination-specific TRIDs to CF patients having higher susceptibility sequence contexts.

Sequence Context Effects on Termination

RFC-catalyzed termination is directly competitive with functional near-cognate tRNA binding to a PTC. This study focused on downstream sequences of PTC and mutations in the CFTR mRNAs found in cystic fibrosis (CF) patients. The high throughput fluorescence anisotropy assay was used to determine termination rates as a function of RFC concentration, permitting estimation of $K_m^{RFC}$ and $k_{cat}$ values for the three studied mutations (Table 10). These results provided a clear demonstration of the major influence that both downstream context and the codon identity had on the catalytic efficiency of RFC, as measured by the $k_{cat}/K_m^{RFC}$ ratio. Lower values would be expected to correlate with less effective competition vs. near-cognate tRNA binding (FIG. 15D) and thus higher readthrough. By this measure, the three sequences sharing a common UGA stop codon were predicted to have readthrough efficiencies falling in the order RefSeq>S1196>W1282, with the major differences between the three coming from changes in $K_m^{RFC}$.

TABLE 10

Effect of termination codon and downstream sequence on RFC activity.

| Mutant | Sequence down-stream of PTC in Stop-POST5 | SEQ ID NO | $K_D$ (μM) | $V_{max}$ ($min^{-1}$) | $K_{cat}/K_D$ ($\mu M^{-1}min^{-1}$) |
|---|---|---|---|---|---|
| Reference | <u>UGA</u> CUA AUG ACA UUU | 45 | 0.06 ± 0.04 | 0.4 ± 0.1 | 7 |
| sequence | FK*VRQ-Stop-LMTF | 57, 46 | | | |
| CFTR- | <u>UGA</u> <u>C</u>AC GUG AAG AAA | 41 | 0.004 ± 0.001 | 0.21 ± 0.01 | 50 |
| S1196X | FK*VRQ-Stop-HVKK | 57, 47 | | | |
| CFTR- | <u>UGA</u> <u>CGC</u> <u>C</u>UG GAA UUG | 48 | ≤0.0005 | 0.07 ± 0.01 | ≥140 |
| Q30X | FK*VRQ-Stop-RLQL | 57, 49 | | | |
| CFTR- | <u>UGA</u> A<u>G</u>G AAA GCC UUU | 43 | 0.001 ± 0.0004 | 0.40 ± 0.03 | 400 |
| W1282X | FK*VRQ-Stop-RKAF $K_{fast}$ | 57, 50 | | | |
| CFTR- | <u>UGA</u> CUC UUU AAG UUC | 51 | 0.0009 ± 0.0001 | 0.15 ± 0.01 | 170 |
| R1162X | FK*VRQ-Stop-VFKF | 57, 52 | | | |
| FBN1- | <u>UGA</u> GGA AAC CCA GAG | 53 | 0.003 ± 0.001 | 0.21 ± 0.01 | 70 |
| R2694X | FK*VRQ-Stop-GNPE | 57, 54 | | | |

Reference sequence was selected because it was predicted to give maximal readthrough following a UGA PSC.

Stop codons are underlined. Few of the nucleotides predicted to favor readthrough are double underlined.

Example 7. Single Molecule FRET (smFRET) Experiments with Cy5-Labeled Human eRF1 and Cy5-Labeled Human eRF3

Figure 15A:
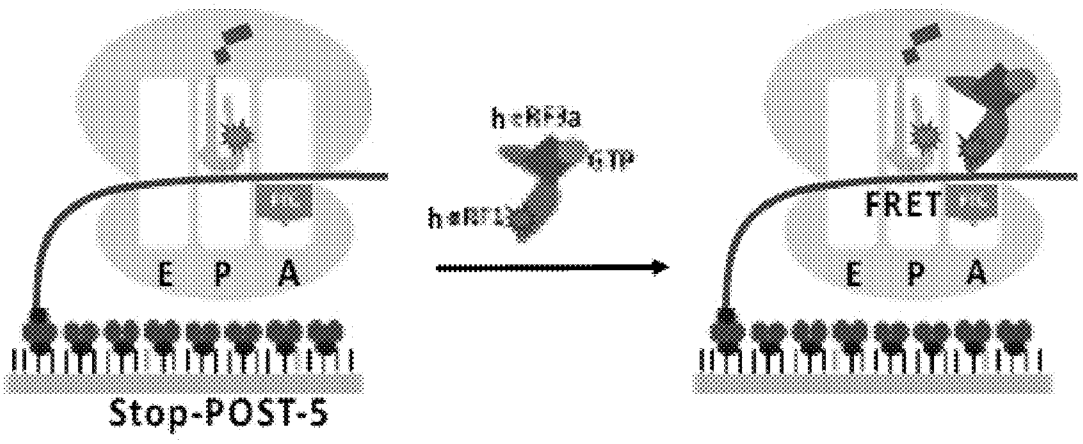
FIGS. 15A, 15B, 15C, and 15D are a diagram and graphs showing transient Cy5-hRF1.hRF3.GTP binding to Stop-POST5 FRET.
Figure 15B:
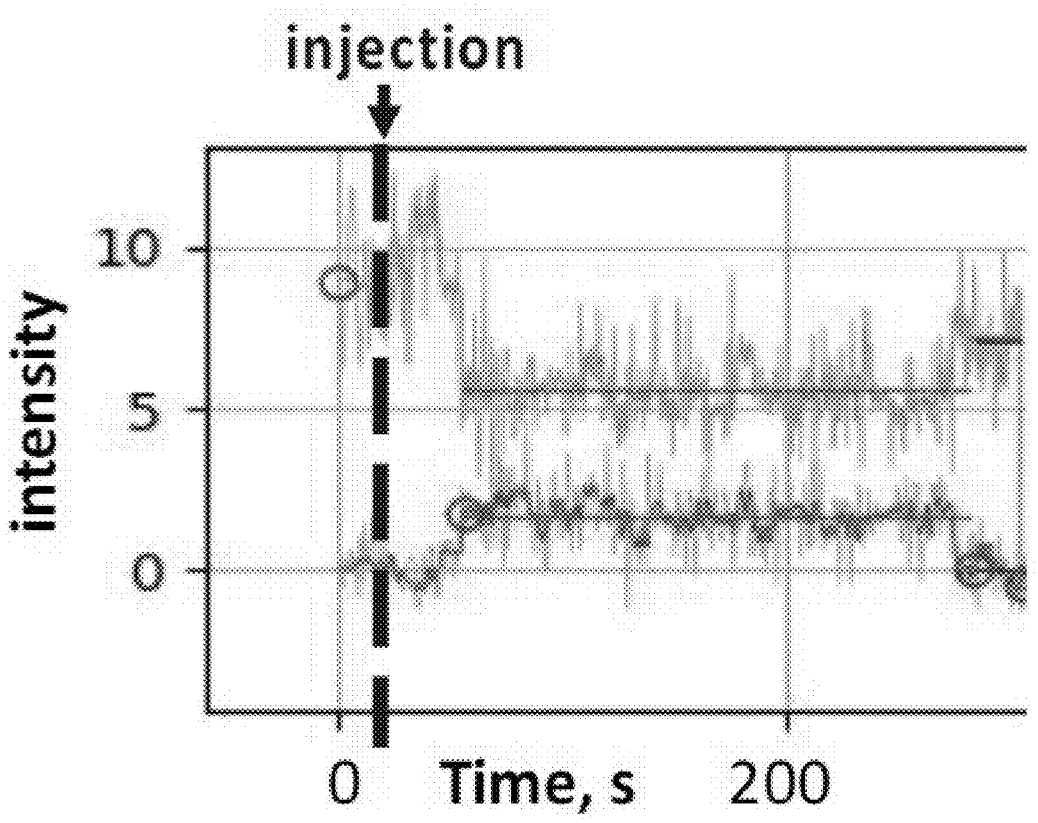
Figure 15C:
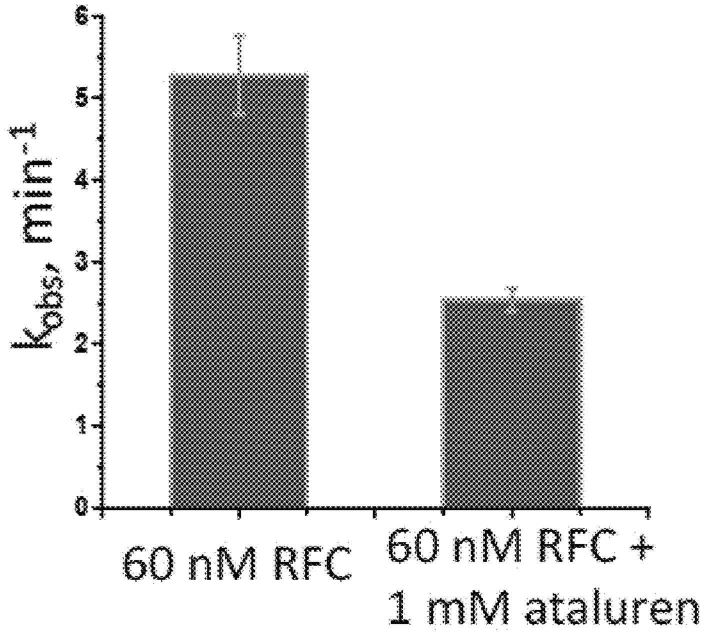
Figure 15D:
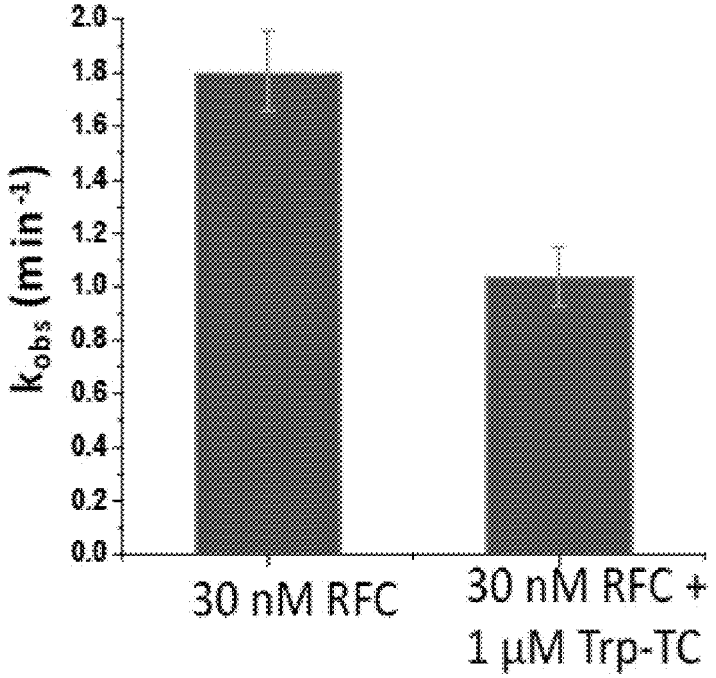

The Cy5-labeled human eRF1 (heRF1) and, more recently, Cy5-labeled human eRF3 (heRF3), using a ybbR labeling approach, paralleling the published preparation of fluorescently labeled *S. cerevisiae* eRF1 and eRF3, were used in this study. Several important results have been obtained with Cy5-heRF1 which further elucidate the mechanism of termination shown in FIGS. 14A and 14B. Cy5-heRF1 forms a catalytically active RFC with unlabeled heRF3, which, when added to the Stop-POST5 complex, generated a transient FRET signal with FKVRQ-tRNA$^{Gln}$ (Cy3) (SEQ ID NO: 22) bound in the P-site (FIGS. 15A and 15B). Added ataluren (1 mM) strongly inhibited the rate of Cy5-hRF1.hRF3.GTP binding to Stop-POST5 (FIG. 15C), demonstrating that the apparent competitive inhibition by ataluren of RFC corresponded to classical competitive inhibition of binding, albeit via ataluren binding to multiple sites. As expected, added near-cognate Trp-TC (1 μM) also inhibited Cy5-hRF1.hRF3.GTP binding (FIG. 15D). Furthermore, results showed that, following peptidyl-tRNA hydrolysis, the release of tRNA$^{Gln}$ (Cy3) and Cy5-hRF1 was strongly correlated (CC, ~0.3), an indication that they may proceed via rate-determining steps which are more closely related than the rate determining steps governing the rates of release of tRNA$^{Gln}$ (Cy3) and FKVRQ (SEQ ID NO: 57).

smFRET Experiments Comparing Cognate and Near-Cognate Elongation Cycles.

Conversion of Trp-POST5 and Stop-POST5 to Trp-PRE6 and Stop-PRE6, respectively.

Figure 16A:
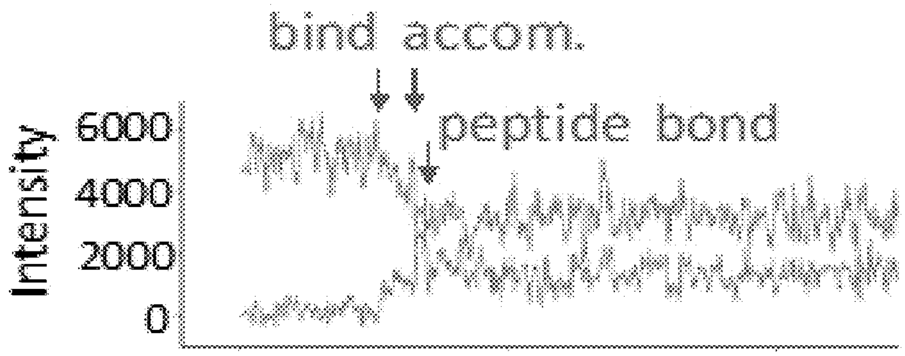
FIGS. 16A, 16B, 16C, 16D, 16E, 16F, 16G, 16H and 16I are diagrams and graphs showing smTIRF elongation cycle.
Figure 16B:
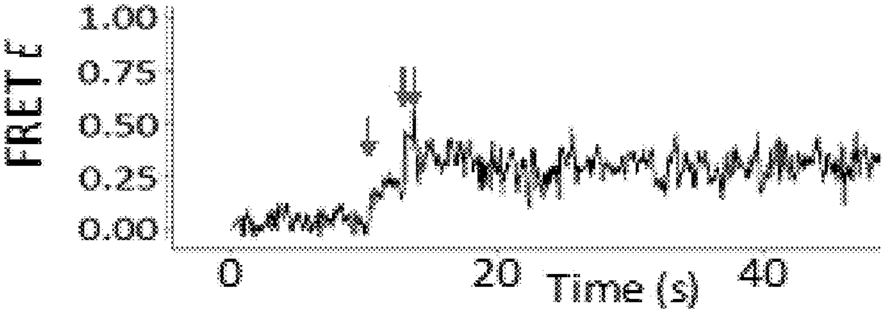
Figure 16C:
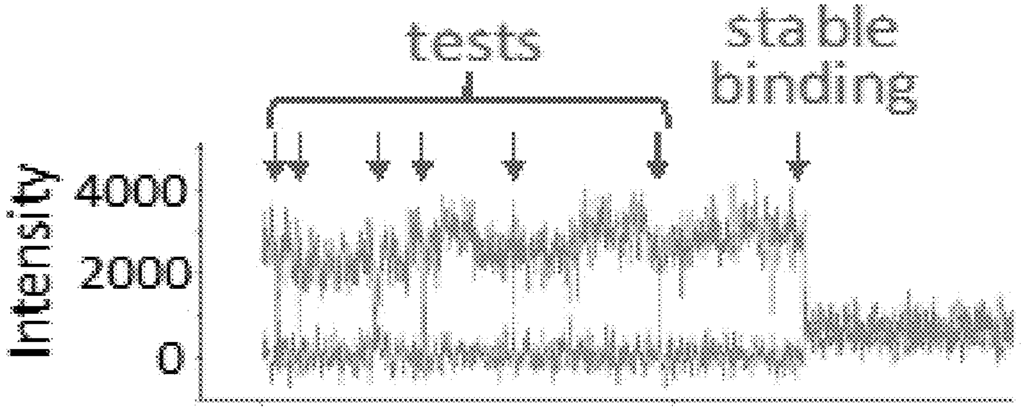
Figure 16D:
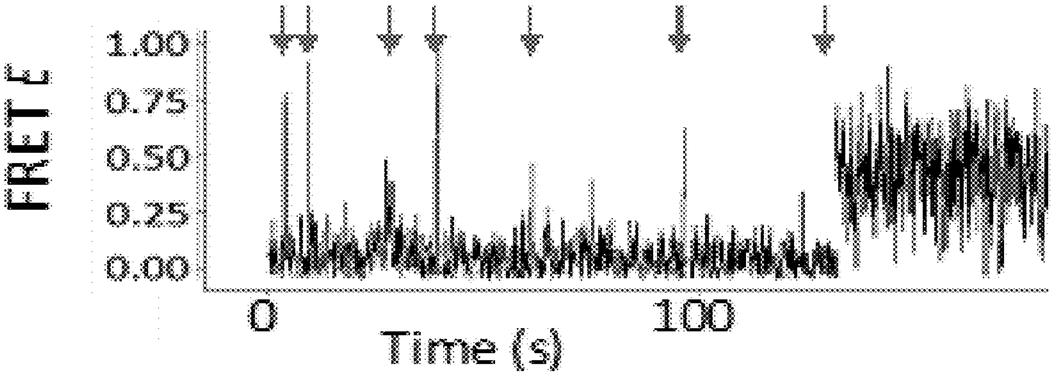

The dynamics of binding of Trp-TC to both POST5 complexes followed by accommodation into the A-site with peptide formation were quantified. Binding of Trp-TC to the cognate UGG codon in the ribosomal A-site of Trp-POST5 usually (80-90%) resulted in stable interaction and formation of PRE6 complex (FIGS. 16A and 16B). In contrast, binding to the near-cognate UGA codon in Stop-POST5 most often resulted in rapid dissociation, with several test bindings observed before stable binding and formation of Stop-PRE6 (FIGS. 16C and 16D).

Taking advantage of the feature of single molecule spectroscopy to detect trajectories of the individual ribosomes, two unexpected features of the kinetics of Trp-TC interaction with Stop-POST5 were found, which have not been reported in earlier studies of bacterial ribosomes. i. The first test binding of Trp-TC proceeded with a rate constant of $1\times10^6$ $M^{-1}s^{-1}$, whereas subsequent binding events occurred approximately 5 times faster. ii. The number of testing events per stable event increased proportionally four-fold when [Trp-TC] concentration increased from 10-40 nM, a clear indication that higher [Trp-TC] favors dissociation. These unexpected features could have strong influence on the competition of readthrough vs. successful termination by the RFC complex.

Translocation of Trp-PRE6 to Trp-POST6.

Figure 16E:
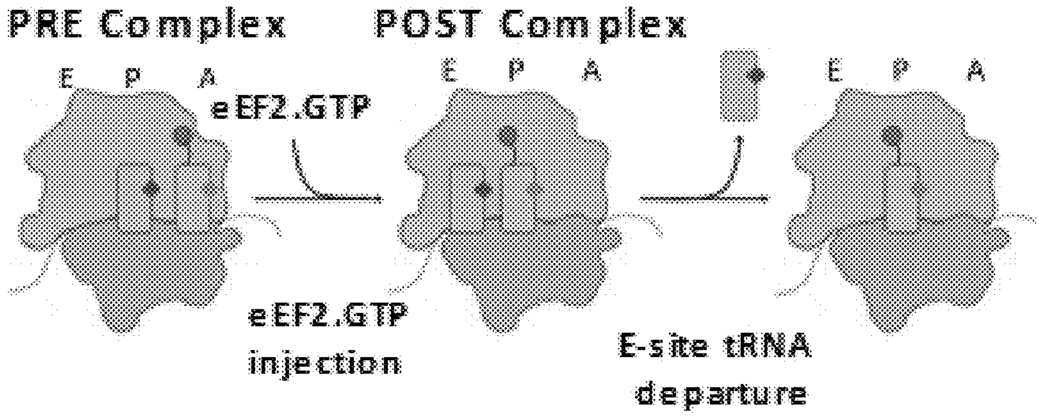
Figure 16F:
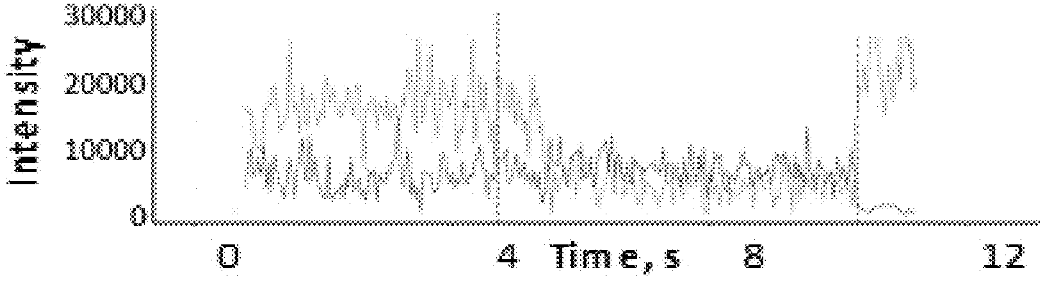
Figure 16G:
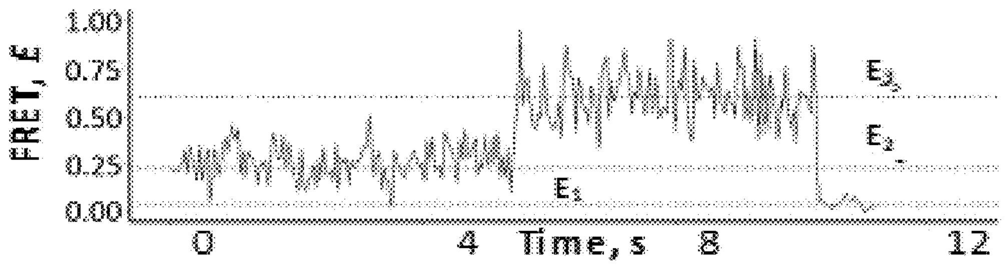
Figure 16H:
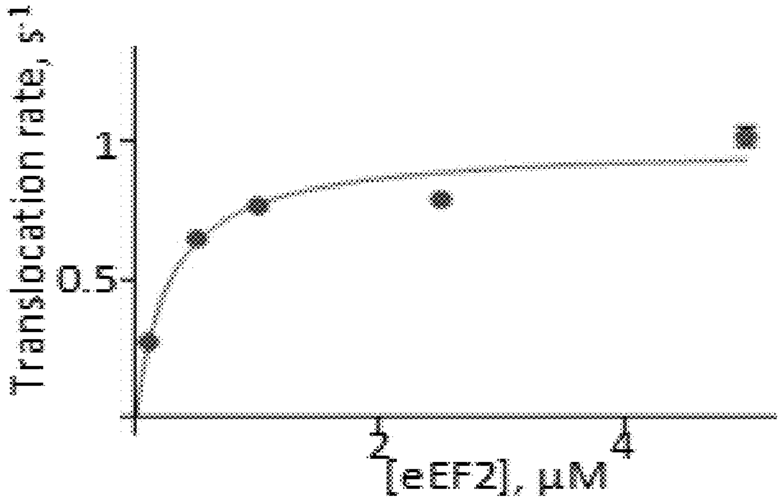
Figure 16I:
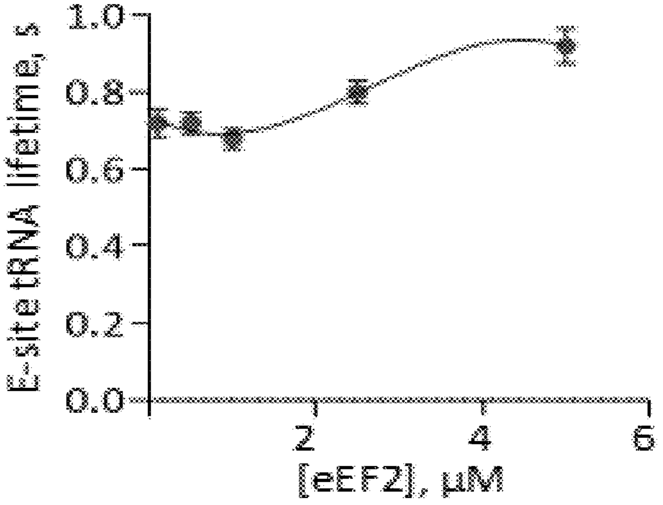

Changes in FRET (FIGS. 16E-16G) were used to determine the rate of translocation (FIG. 16H) and the residence time of deacylated tRNA dissociation from the E-site (FIG. 16I) as functions of [eEF2.GTP]. It was found that the rate of translocation saturates as a function of [eEF2], yielding values of $K_m^{eEF2}$ (0.28 μM) and $k_{cat}$ (1.0 $s^{-1}$) at 23° C., while the tRNA E-site residence time of 0.8 s was independent of [eEF2].

Figure 17A:
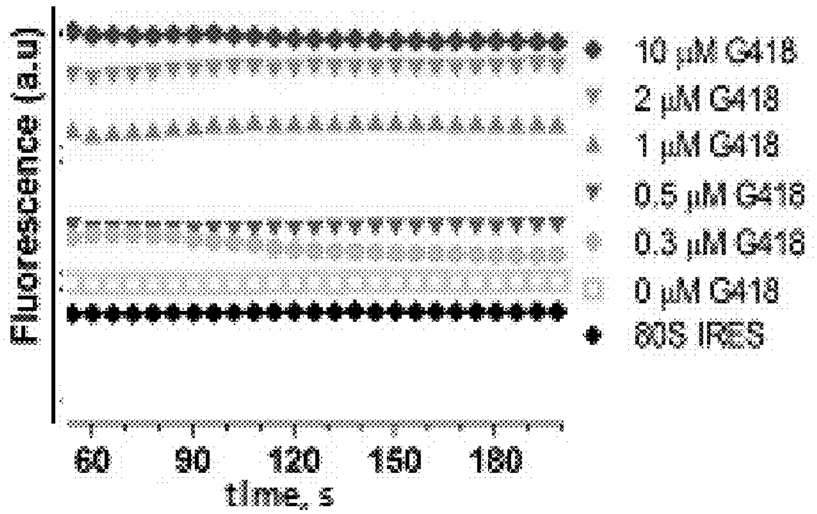
FIGS. 17A, 17B, 17C, and 17D are graphs showing data from the high throughput translocation assay.
Figure 17B:
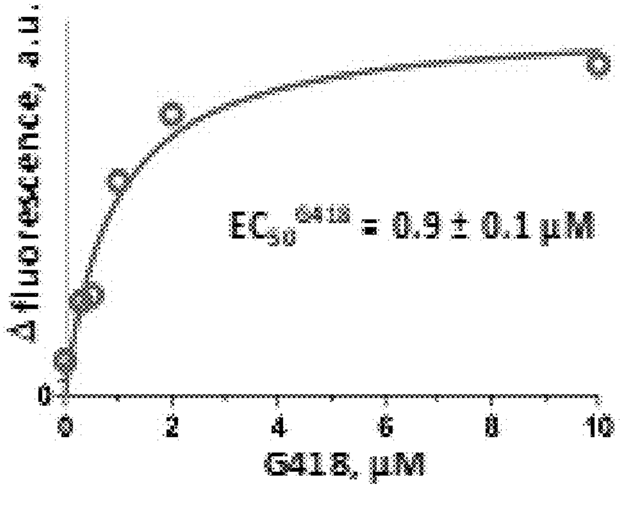
Figure 17C:
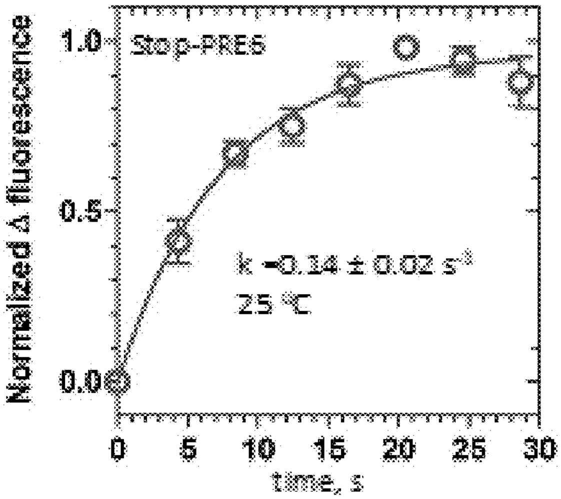
Figure 17D:
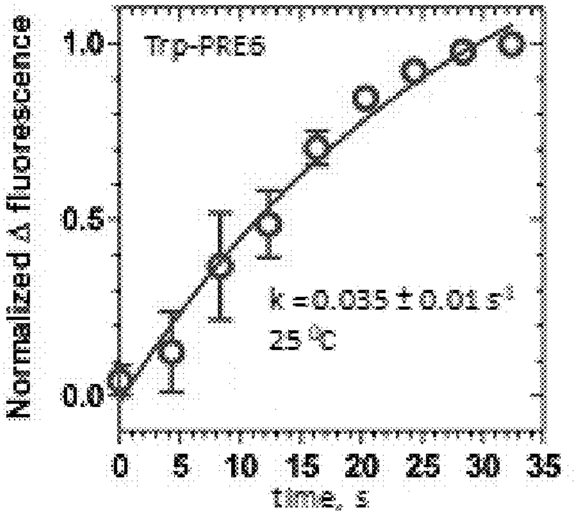

Example 8. New High Throughput Assays Measuring Translocation During Readthrough and Cognate Elongation Different proflavin-labeled aa-tRNAs, denoted aa-tRNA (prf) s, were used to monitor the elongation cycle changes by fluorescence change at 511 nm following excitation at 458 nm (Ng et al. PNAS, 118 (2) e2020599118, 1-10 (2021)). Binding of Trp-TC (prf) to a Trp-POST5 complex in the presence of eEF2 lead to a biphasic increase, with the first, more rapid phase corresponding to formation of Trp-PRE6, followed by a slower, eEF2-dependent phase corresponding to conversion of Trp-PRE6 into Trp-POST6. The translocation step was monitored using a plate-reader assay for both G418-stimulated readthrough of Stop-POST5 (FIGS. 17A-17C) and cognate elongation of Trp-POST5 (FIG. 17D) by adjustment of [eEF2]. The $EC_{50}$ value for G418 (FIG. 17B) and the rates of translocation (FIGS. 17C and 17D) are fully consistent with previous determination of these values using a stopped-flow spectrofluorometer.

SEQUENCE LISTING

```
Sequence total quantity: 57
SEQ ID NO: 1            moltype = DNA  length = 60
FEATURE                 Location/Qualifiers
source                  1..60
                        mol_type = other DNA
                        organism = synthetic construct
SEQUENCE: 1
agcctgcggc ttaatttgac tcaacacggg aaacctcacc cggcccggac acggacagga  60

SEQ ID NO: 2            moltype = DNA  length = 60
FEATURE                 Location/Qualifiers
source                  1..60
                        mol_type = other DNA
                        organism = synthetic construct
SEQUENCE: 2
agcctgcggc ttaatttgac tcaacacggg aaacctcacc cggcccggac acggacagga  60

SEQ ID NO: 3            moltype = DNA  length = 60
FEATURE                 Location/Qualifiers
source                  1..60
```

```
                        mol_type = other DNA
                        organism = synthetic construct
SEQUENCE: 3
agcctgcggc ttaatttgac tcaacacggg aaacctcacc aggcccggac actggaagga  60

SEQ ID NO: 4            moltype = DNA  length = 60
FEATURE                 Location/Qualifiers
source                  1..60
                        mol_type = other DNA
                        organism = synthetic construct
SEQUENCE: 4
agcctgcggc ttaatttgac tcaacacggg gaaactcacc aggtccagac acaataagga  60

SEQ ID NO: 5            moltype = DNA  length = 60
FEATURE                 Location/Qualifiers
source                  1..60
                        mol_type = other DNA
                        organism = synthetic construct
SEQUENCE: 5
aaccacagcc aagggaacgg gcttggcaga atcagcgggg aaagaagacc ctgttgagct  60

SEQ ID NO: 6            moltype = DNA  length = 60
FEATURE                 Location/Qualifiers
source                  1..60
                        mol_type = other DNA
                        organism = synthetic construct
SEQUENCE: 6
acccactgcc aggggaacgg gcctggtaac gtctgcgggg aaagaagacc ctgttgagct  60

SEQ ID NO: 7            moltype = DNA  length = 60
FEATURE                 Location/Qualifiers
source                  1..60
                        mol_type = other DNA
                        organism = synthetic construct
SEQUENCE: 7
aaccacagcc aagggaacgg gcttggcgga atcagcgggg aaagaagacc ctgttgagct  60

SEQ ID NO: 8            moltype = DNA  length = 60
FEATURE                 Location/Qualifiers
source                  1..60
                        mol_type = other DNA
                        organism = synthetic construct
SEQUENCE: 8
cctttagtcc ctcggaattt gaggctagag gtgccagaaa agttaccaca gggataactg  60

SEQ ID NO: 9            moltype = DNA  length = 60
FEATURE                 Location/Qualifiers
source                  1..60
                        mol_type = other DNA
                        organism = synthetic construct
SEQUENCE: 9
ccttttggct ttaagagttt taagcaagag gtgtcagaaa agttaccaca gggataactg  60

SEQ ID NO: 10           moltype = DNA  length = 60
FEATURE                 Location/Qualifiers
source                  1..60
                        mol_type = other DNA
                        organism = synthetic construct
SEQUENCE: 10
ccttctgacc ttttgggttt taagcaggag gtgtcagaaa agttaccaca gggataactg  60

SEQ ID NO: 11           moltype = DNA  length = 17
FEATURE                 Location/Qualifiers
source                  1..17
                        mol_type = other DNA
                        organism = synthetic construct
SEQUENCE: 11
cactcgggca ccaagga                                                 17

SEQ ID NO: 12           moltype = DNA  length = 13
FEATURE                 Location/Qualifiers
source                  1..13
                        mol_type = other DNA
                        organism = synthetic construct
SEQUENCE: 12
tcaattcctt taa                                                     13

SEQ ID NO: 13           moltype = DNA  length = 16
FEATURE                 Location/Qualifiers
```

```
source                1..16
                      mol_type = other DNA
                      organism = synthetic construct
SEQUENCE: 13
gaggtttccc gtgttg                                                         16

SEQ ID NO: 14         moltype = DNA  length = 15
FEATURE               Location/Qualifiers
source                1..15
                      mol_type = other DNA
                      organism = synthetic construct
SEQUENCE: 14
ctcttgctta aaact                                                          15

SEQ ID NO: 15         moltype = DNA  length = 12
FEATURE               Location/Qualifiers
source                1..12
                      mol_type = other DNA
                      organism = synthetic construct
SEQUENCE: 15
cttggccgcc ac                                                             12

SEQ ID NO: 16         moltype = DNA  length = 12
FEATURE               Location/Qualifiers
source                1..12
                      mol_type = other DNA
                      organism = synthetic construct
SEQUENCE: 16
ggcccgttcc cc                                                             12

SEQ ID NO: 17         moltype = DNA  length = 13
FEATURE               Location/Qualifiers
source                1..13
                      mol_type = other DNA
                      organism = synthetic construct
SEQUENCE: 17
ctccacaata ccg                                                            13

SEQ ID NO: 18         moltype = DNA  length = 13
FEATURE               Location/Qualifiers
source                1..13
                      mol_type = other DNA
                      organism = synthetic construct
SEQUENCE: 18
ccgacctcca tgg                                                            13

SEQ ID NO: 19         moltype = DNA  length = 13
FEATURE               Location/Qualifiers
source                1..13
                      mol_type = other DNA
                      organism = synthetic construct
SEQUENCE: 19
gcctcccatt tta                                                            13

SEQ ID NO: 20         moltype = AA  length = 5
FEATURE               Location/Qualifiers
source                1..5
                      mol_type = protein
                      organism = synthetic construct
SEQUENCE: 20
FKVRQ                                                                     5

SEQ ID NO: 21         moltype = AA  length = 5
FEATURE               Location/Qualifiers
source                1..5
                      mol_type = protein
                      organism = synthetic construct
SEQUENCE: 21
FCFFQ                                                                     5

SEQ ID NO: 22         moltype = AA  length = 5
FEATURE               Location/Qualifiers
source                1..5
                      mol_type = protein
                      organism = synthetic construct
SITE                  5
                      note = tRNA loaded with Glutamine and labeled with Cy3
                       fluorescent dye
SEQUENCE: 22
```

```
FKVRQ                                                         5

SEQ ID NO: 23          moltype = AA  length = 6
FEATURE                Location/Qualifiers
source                 1..6
                       mol_type = protein
                       organism = synthetic construct
SITE                   6
                       note = tRNA loaded with Tryptophan and labeled with Cy5
                        fluorescent dye
SEQUENCE: 23
FKVRQW                                                        6

SEQ ID NO: 24          moltype = AA  length = 5
FEATURE                Location/Qualifiers
source                 1..5
                       mol_type = protein
                       organism = synthetic construct
SITE                   5
                       note = tRNA loaded with Glutamine and labeled with Cy3
                        fluorescent dye
SITE                   2
                       note = Labeled with Atto647
SEQUENCE: 24
FKVRQ                                                         5

SEQ ID NO: 25          moltype = AA  length = 5
FEATURE                Location/Qualifiers
source                 1..5
                       mol_type = protein
                       organism = synthetic construct
SITE                   5
                       note = tRNA loaded with Glutamine
SEQUENCE: 25
FKVRQ                                                         5

SEQ ID NO: 26          moltype =   length =
SEQUENCE: 26
000

SEQ ID NO: 27          moltype = AA  length = 5
FEATURE                Location/Qualifiers
source                 1..5
                       mol_type = protein
                       organism = synthetic construct
SITE                   2
                       note = Labeled amino acid residue
SEQUENCE: 27
FKFFF                                                         5

SEQ ID NO: 28          moltype = AA  length = 5
FEATURE                Location/Qualifiers
source                 1..5
                       mol_type = protein
                       organism = synthetic construct
SEQUENCE: 28
DNTVL                                                         5

SEQ ID NO: 29          moltype = RNA  length = 15
FEATURE                Location/Qualifiers
source                 1..15
                       mol_type = other RNA
                       organism = synthetic construct
modified_base          1
                       mod_base = OTHER
                       note = uracil
modified_base          8
                       mod_base = OTHER
                       note = uracil
modified_base          13..14
                       mod_base = OTHER
                       note = uracil
SEQUENCE: 29
tagcgcctgg aattg                                              15

SEQ ID NO: 30          moltype = AA  length = 4
FEATURE                Location/Qualifiers
source                 1..4
                       mol_type = protein
```

```
                         organism = synthetic construct
SEQUENCE: 30
RLEL                                                                  4

SEQ ID NO: 31            moltype = RNA  length = 15
FEATURE                  Location/Qualifiers
source                   1..15
                         mol_type = other RNA
                         organism = synthetic construct
modified_base            1
                         mod_base = OTHER
                         note = uracil
modified_base            5
                         mod_base = OTHER
                         note = uracil
modified_base            9..10
                         mod_base = OTHER
                         note = uracil
SEQUENCE: 31
tagctggctt caaag                                                      15

SEQ ID NO: 32            moltype = AA  length = 4
FEATURE                  Location/Qualifiers
source                   1..4
                         mol_type = protein
                         organism = synthetic construct
SEQUENCE: 32
LASK                                                                  4

SEQ ID NO: 33            moltype = RNA  length = 15
FEATURE                  Location/Qualifiers
source                   1..15
                         mol_type = other RNA
                         organism = synthetic construct
modified_base            1
                         mod_base = OTHER
                         note = uracil
modified_base            9
                         mod_base = OTHER
                         note = uracil
modified_base            14
                         mod_base = OTHER
                         note = uracil
SEQUENCE: 33
tgagaaggtg gaatc                                                      15

SEQ ID NO: 34            moltype = AA  length = 4
FEATURE                  Location/Qualifiers
source                   1..4
                         mol_type = protein
                         organism = synthetic construct
SEQUENCE: 34
DGGI                                                                  4

SEQ ID NO: 35            moltype = RNA  length = 15
FEATURE                  Location/Qualifiers
source                   1..15
                         mol_type = other RNA
                         organism = synthetic construct
modified_base            1
                         mod_base = OTHER
                         note = uracil
modified_base            11..13
                         mod_base = OTHER
                         note = uracil
modified_base            15
                         mod_base = OTHER
                         note = uracil
SEQUENCE: 35
tgagcaagaa tttct                                                      15

SEQ ID NO: 36            moltype = AA  length = 4
FEATURE                  Location/Qualifiers
source                   1..4
                         mol_type = protein
                         organism = synthetic construct
SEQUENCE: 36
ARIS                                                                  4
```

```
SEQ ID NO: 37           moltype = RNA  length = 15
FEATURE                 Location/Qualifiers
source                  1..15
                        mol_type = other RNA
                        organism = synthetic construct
modified_base           1
                        mod_base = OTHER
                        note = uracil
modified_base           5
                        mod_base = OTHER
                        note = uracil
modified_base           7
                        mod_base = OTHER
                        note = uracil
modified_base           14
                        mod_base = OTHER
                        note = uracil
SEQUENCE: 37
tarctgtcaa cactg                                                   15

SEQ ID NO: 38           moltype = AA  length = 4
FEATURE                 Location/Qualifiers
source                  1..4
                        mol_type = protein
                        organism = synthetic construct
SEQUENCE: 38
LSTL                                                               4

SEQ ID NO: 39           moltype = RNA  length = 15
FEATURE                 Location/Qualifiers
source                  1..15
                        mol_type = other RNA
                        organism = synthetic construct
modified_base           1
                        mod_base = OTHER
                        note = uracil
modified_base           5
                        mod_base = OTHER
                        note = uracil
modified_base           7..9
                        mod_base = OTHER
                        note = uracil
modified_base           13..14
                        mod_base = OTHER
                        note = uracil
SEQUENCE: 39
tgagtcttta agttc                                                   15

SEQ ID NO: 40           moltype = AA  length = 4
FEATURE                 Location/Qualifiers
source                  1..4
                        mol_type = protein
                        organism = synthetic construct
SEQUENCE: 40
VFKF                                                               4

SEQ ID NO: 41           moltype = RNA  length = 15
FEATURE                 Location/Qualifiers
source                  1..15
                        mol_type = other RNA
                        organism = synthetic construct
modified_base           1
                        mod_base = OTHER
                        note = uracil
modified_base           8
                        mod_base = OTHER
                        note = uracil
SEQUENCE: 41
tgacacgtga agaaa                                                   15

SEQ ID NO: 42           moltype = AA  length = 4
FEATURE                 Location/Qualifiers
source                  1..4
                        mol_type = protein
                        organism = synthetic construct
SEQUENCE: 42
HVKK                                                               4

SEQ ID NO: 43           moltype = RNA  length = 15
```

```
FEATURE                Location/Qualifiers
source                 1..15
                       mol_type = other RNA
                       organism = synthetic construct
modified_base          1
                       mod_base = OTHER
                       note = uracil
modified_base          13..15
                       mod_base = OTHER
                       note = uracil
SEQUENCE: 43
tgaaggaaag ccttt                                                    15

SEQ ID NO: 44          moltype = AA  length = 4
FEATURE                Location/Qualifiers
source                 1..4
                       mol_type = protein
                       organism = synthetic construct
SEQUENCE: 44
RKAF                                                                4

SEQ ID NO: 45          moltype = RNA  length = 15
FEATURE                Location/Qualifiers
source                 1..15
                       mol_type = other RNA
                       organism = synthetic construct
modified_base          1
                       mod_base = OTHER
                       note = uracil
modified_base          5
                       mod_base = OTHER
                       note = uracil
modified_base          8
                       mod_base = OTHER
                       note = uracil
modified_base          13..15
                       mod_base = OTHER
                       note = uracil
SEQUENCE: 45
tgactaatga cattt                                                    15

SEQ ID NO: 46          moltype = AA  length = 4
FEATURE                Location/Qualifiers
source                 1..4
                       mol_type = protein
                       organism = synthetic construct
SEQUENCE: 46
LMTF                                                                4

SEQ ID NO: 47          moltype = AA  length = 4
FEATURE                Location/Qualifiers
source                 1..4
                       mol_type = protein
                       organism = synthetic construct
SEQUENCE: 47
HVKK                                                                4

SEQ ID NO: 48          moltype = RNA  length = 15
FEATURE                Location/Qualifiers
source                 1..15
                       mol_type = other RNA
                       organism = synthetic construct
modified_base          1
                       mod_base = OTHER
                       note = uracil
modified_base          8
                       mod_base = OTHER
                       note = uracil
modified_base          13..14
                       mod_base = OTHER
                       note = uracil
SEQUENCE: 48
tgacgcctgg aattg                                                    15

SEQ ID NO: 49          moltype = AA  length = 4
FEATURE                Location/Qualifiers
source                 1..4
                       mol_type = protein
                       organism = synthetic construct
```

```
SEQUENCE: 49
RLQL                                                            4

SEQ ID NO: 50          moltype = AA  length = 4
FEATURE                Location/Qualifiers
source                 1..4
                       mol_type = protein
                       organism = synthetic construct
SEQUENCE: 50
RKAF                                                            4

SEQ ID NO: 51          moltype = RNA  length = 15
FEATURE                Location/Qualifiers
source                 1..15
                       mol_type = other RNA
                       organism = synthetic construct
modified_base          1
                       mod_base = OTHER
                       note = uracil
modified_base          5
                       mod_base = OTHER
                       note = uracil
modified_base          7..9
                       mod_base = OTHER
                       note = uracil
modified_base          13..14
                       mod_base = OTHER
                       note = uracil
SEQUENCE: 51
tgactcttta agttc                                                15

SEQ ID NO: 52          moltype = AA  length = 4
FEATURE                Location/Qualifiers
source                 1..4
                       mol_type = protein
                       organism = synthetic construct
SEQUENCE: 52
VFKF                                                            4

SEQ ID NO: 53          moltype = RNA  length = 15
FEATURE                Location/Qualifiers
source                 1..15
                       mol_type = other RNA
                       organism = synthetic construct
modified_base          1
                       mod_base = OTHER
                       note = uracil
SEQUENCE: 53
tgaggaaacc cagag                                                15

SEQ ID NO: 54          moltype = AA  length = 4
FEATURE                Location/Qualifiers
source                 1..4
                       mol_type = protein
                       organism = synthetic construct
SEQUENCE: 54
GNPE                                                            4

SEQ ID NO: 55          moltype = RNA  length = 24
FEATURE                Location/Qualifiers
source                 1..24
                       mol_type = other RNA
                       organism = synthetic construct
modified_base          1..2
                       mod_base = OTHER
                       note = uracil
modified_base          8
                       mod_base = OTHER
                       note = uracil
modified_base          16
                       mod_base = OTHER
                       note = uracil
modified_base          20
                       mod_base = OTHER
                       note = uracil
modified_base          23
                       mod_base = OTHER
                       note = uracil
SEQUENCE: 55
```

-continued

```
ttcaaagtga gacaatgact aatg                                            24

SEQ ID NO: 56           moltype = RNA  length = 24
FEATURE                 Location/Qualifiers
source                  1..24
                        mol_type = other RNA
                        organism = synthetic construct
modified_base           1..2
                        mod_base = OTHER
                        note = uracil
modified_base           4
                        mod_base = OTHER
                        note = uracil
modified_base           7..8
                        mod_base = OTHER
                        note = uracil
modified_base           10..11
                        mod_base = OTHER
                        note = uracil
modified_base           16
                        mod_base = OTHER
                        note = uracil
modified_base           20
                        mod_base = OTHER
                        note = uracil
modified_base           23
                        mod_base = OTHER
                        note = uracil
SEQUENCE: 56
ttctgcttct tccaatgact aatg                                            24

SEQ ID NO: 57           moltype = AA  length = 5
FEATURE                 Location/Qualifiers
source                  1..5
                        mol_type = protein
                        organism = synthetic construct
SITE                    2
                        note = Labeled amino acid residue
SEQUENCE: 57
FKVRQ                                                                 5
```

What is claimed:

1. A system comprising a substrate and a plurality of regions on the substrate, each region comprising a cell-free ribosome-dependent protein synthesis reporter complex, wherein the cell-free ribosome-dependent protein synthesis reporter complex comprises:

a) transfer-ribonucleic acid linked to a peptide (peptidyl-tRNA), wherein one or more amino acids of the peptide are labeled with a first fluorophore or a chromophore, b) a transfer-ribonucleic acid;

c) a modified ribonucleic acid (RNA) molecule comprising an internal ribosome entry site (IRES) linked to a coding region encoding the peptide of the peptidyl-tRNA and a termination codon (Stop-IRES mRNA); and d) a ribosome, wherein the transfer-ribonucleic acid or the ribosome is linked to a second fluorophore or a second chromophore to form a labeled-tRNA or a labeled ribosome, respectively.

2. The system of claim 1, wherein the peptidyl-tRNA comprises between one and 15 amino acids.

3. The system of claim 1, wherein the peptidyl-tRNA comprises at least one canonical or non-canonical amino acid labeled with the first fluorophore or the chromophore.

4. The system of claim 1, wherein the first and the second fluorophore or the chromophore absorbs light at wavelengths between about 340 nm and 780 nm.

5. The system of claim 1, wherein the first and the second fluorophore or the chromophore emits light at wavelengths between about 440 nm and 810 nm.

6. The system of claim 1, wherein the IRES is from cricket paralysis virus internal ribosome entry site (CrPV-IRES).

7. The system of claim 1, wherein the cell-free ribosome-dependent protein synthesis reporter complex comprises a eukaryotic ribosome, eukaryotic elongation factors (eEF)1A and eEF2, and aminoacyl-tRNAs.

8. The system of claim 1, wherein the peptidyl-tRNA is located at peptidyl-site (P-site) of the ribosome, forming Stop-POST complex.

9. The system of claim 1, wherein the region comprises an isolated area selected from the group consisting of a matrix, a well, a vessel, and a chamber.

10. A high throughput assay for detecting translation readthrough induced drug (TRID), the assay comprising:

a) combining, in the region of the system of claim 1;

i) a drug; and ii) a release factor complex; and b) measuring fluorescence anisotropy or measuring change in fluorescence or absorption by measuring fluorescence from the cell-free ribosome-dependent protein synthesis reporter complex.

11. The assay of claim 10, wherein the peptidyl-tRNA comprises between one and 15 amino acids.

12. The assay of claim 10, wherein the peptidyl-tRNA comprises at least one canonical or non-canonical amino acid labeled with the first fluorophore or the first chromophore.

13. The assay of claim 10, wherein the first fluorophore, the first chromophore, the second fluorophore, or the second chromophore absorbs light at wavelengths between about 340 nm and 780 nm.

14. The assay of claim 10, wherein the first fluorophore, the first chromophore, the second fluorophore, or the second chromophore emits light at wavelengths between about 440 nm and 810 nm.

15. The assay of claim 10, wherein the IRES is from cricket paralysis virus internal ribosome entry site (CrPV-IRES).

16. The assay of claim 10, wherein the cell-free ribosome-dependent protein synthesis reporter complex comprises a eukaryotic ribosome, eukaryotic elongation factors (eEF)1A and eEF2, guanosine-5'-triphosphate (GTP), and optionally, aminoacyl-tRNAs.

17. The assay of claim 10, wherein the drug is from a library of drugs.

18. The assay of claim 10, wherein the release factor complex comprises a release factor selected from the group consisting of eukaryotic peptide release factor (eRF)1, eRF3, and Rli1/ABCE1.

19. The assay of claim 10, wherein the drug is translation readthrough induced drug when the fluorescence anisotropy is substantially reduced during a measuring period, or wherein the drug is not a translation readthrough induced drug when the fluorescence anisotropy is substantially unchanged during a measuring period.

20. A high throughput assay for detecting translation readthrough induced drug (TRID) effective in a disease defined by a premature stop codon (PSC) mutation, the assay comprising:

a) combining, in the region of the system of claim 1, wherein
  the modified ribonucleic acid (RNA) molecule comprises a portion of an mRNA comprising the premature stop codon (PSC) mutation,
  i) a drug; and
  ii) a release factor complex; and b) measuring fluorescence anisotropy or measuring change in fluorescence or absorption, wherein the portion of the mRNA comprising the premature stop codon (PSC) mutation is a portion of mRNA encoding a truncated protein associated with a premature termination codon (PTC) disorder selected from the group consisting of cystic fibrosis, Duchenne muscular dystrophy, β-thalassemia, and cancer.

* * * * *